United States Patent
Jung et al.

(10) Patent No.: US 12,275,736 B2
(45) Date of Patent: Apr. 15, 2025

(54) COMPOUND AND ORGANIC LIGHT EMITTING DEVICE COMPRISING THE SAME

(71) Applicant: LG CHEM, LTD., Seoul (KR)

(72) Inventors: Min Woo Jung, Daejeon (KR); Dong Hoon Lee, Daejeon (KR); Boon Jae Jang, Daejeon (KR); Wanpyo Hong, Daejeon (KR); Sang Duk Suh, Daejeon (KR); Jungha Lee, Daejeon (KR); Su Jin Han, Daejeon (KR); Seulchan Park, Daejeon (KR); Sunghyun Hwang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 769 days.

(21) Appl. No.: 17/282,071

(22) PCT Filed: Nov. 12, 2019

(86) PCT No.: PCT/KR2019/015360
§ 371 (c)(1),
(2) Date: Apr. 1, 2021

(87) PCT Pub. No.: WO2020/111584
PCT Pub. Date: Jun. 4, 2020

(65) Prior Publication Data
US 2021/0355128 A1    Nov. 18, 2021

(30) Foreign Application Priority Data

Nov. 27, 2018 (KR) .......... 10-2018-0148563
Nov. 8, 2019 (KR) .......... 10-2019-0142728

(51) Int. Cl.
*C07D 487/04*    (2006.01)
*C07D 403/14*    (2006.01)
(Continued)

(52) U.S. Cl.
CPC ......... *C07D 487/04* (2013.01); *C07D 403/14* (2013.01); *C07D 405/14* (2013.01);
(Continued)

(58) Field of Classification Search
CPC .. C07D 487/04; C07D 403/14; C07D 405/14; C07D 409/14; C07D 487/14;
(Continued)

(56) References Cited

U.S. PATENT DOCUMENTS 9,577,199 B2   2/2017   Lecloux et al.
2004/0251816 A1  12/2004   Leo et al.
(Continued)

FOREIGN PATENT DOCUMENTS

CN    101087776 A    12/2007
CN    100366703      2/2008
(Continued)

OTHER PUBLICATIONS

Kang, Hosuk, et al. "High-efficiency blue organic light-emitting Diodes using emissive carbazole-triazine-based donor-acceptor molecules with high reverse intersystem crossing rates." Organic Electronics 75 (2019): 105399. (Year: 2019).*

(Continued)

*Primary Examiner* — Dawn L Garrett
(74) *Attorney, Agent, or Firm* — Bryan Cave Leighton Paisner LLP

(57) ABSTRACT

Provided is a compound of Chemical Formula 1:

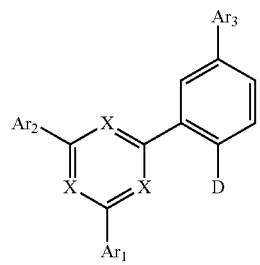

wherein:
each X is independently N or CH, provided that at least one X is N;
$Ar_1$ and $Ar_2$ are each independently a substituted or unsubstituted $C_{6-60}$ aryl or a substituted or unsubstituted $C_{5-60}$ heteroaryl containing one or more of N, O and S;
$Ar_3$ is a substituted or unsubstituted $C_{5-60}$ heteroaryl containing at least one N;

(Continued)

D is a substituent of any one of the following Chemical Formulas 2-1 to 2-3:

Chemical Formula 2-1

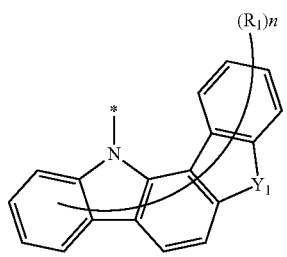

Chemical Formula 2-2

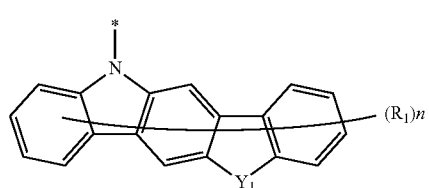

Chemical Formula 2-3

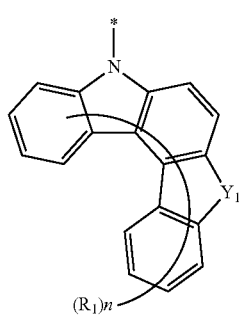

wherein:

$Y_1$ is O, S, $NR_2$, or $CR_3R_4$;

n is an integer of 0 to 10;

each $R_1$ is independently hydrogen, deuterium, or a substituted or unsubstituted: $C_{1-60}$ alkyl, $C_{3-60}$ cycloalkyl, $C_{6-60}$ aryl, or $C_{5-60}$ heteroaryl containing one or more of N, O and S; and $R_2$ to $R_4$ are each independently a substituted or unsubstituted $C_{1-60}$ alkyl or a substituted or unsubstituted $C_{6-60}$ aryl, and an organic light emitting device comprising the same.

7 Claims, 2 Drawing Sheets

(51) Int. Cl.

| | | |
|---|---|---|
| *C07D 405/14* | (2006.01) | |
| *C07D 409/14* | (2006.01) | |
| *C07D 487/14* | (2006.01) | |
| *C07D 491/048* | (2006.01) | |
| *C07D 493/22* | (2006.01) | |
| *C07D 495/04* | (2006.01) | |
| *C07D 495/22* | (2006.01) | |
| *C07D 519/00* | (2006.01) | |
| *C09K 11/06* | (2006.01) | |
| *H10K 50/11* | (2023.01) | |
| *H10K 85/60* | (2023.01) | |
| *H10K 101/00* | (2023.01) | |
| *H10K 101/10* | (2023.01) | |
| *H10K 101/40* | (2023.01) | |

(52) U.S. Cl.
CPC ......... *C07D 409/14* (2013.01); *C07D 487/14* (2013.01); *C07D 491/048* (2013.01); *C07D 493/22* (2013.01); *C07D 495/04* (2013.01); *C07D 495/22* (2013.01); *C07D 519/00* (2013.01); *C09K 11/06* (2013.01); *H10K 85/615* (2023.02); *H10K 85/622* (2023.02); *H10K 85/626* (2023.02); *H10K 85/654* (2023.02); *H10K 85/656* (2023.02); *H10K 85/6572* (2023.02); *H10K 85/6574* (2023.02); *H10K 85/6576* (2023.02); *C09K 2211/1018* (2013.01); *H10K 50/11* (2023.02); *H10K 2101/10* (2023.02); *H10K 2101/40* (2023.02); *H10K 2101/90* (2023.02)

(58) Field of Classification Search
CPC  C07D 491/048; C07D 493/22; C07D 495/04; C07D 495/22; C07D 519/00; C07D 401/14; C07D 407/14; C07D 413/14; C07D 417/14; C07D 498/04; C07D 513/04; C09K 11/06; C09K 2211/1018; H10K 85/615; H10K 85/622; H10K 85/626; H10K 85/654; H10K 85/656; H10K 85/6572; H10K 85/6574; H10K 85/6576; H10K 50/11; H10K 2101/10; H10K 2101/40; H10K 2101/90; H10K 85/342; H10K 85/657

See application file for complete search history.

(56) References Cited

U.S. PATENT DOCUMENTS

| | | |
|---|---|---|
| 2009/0191426 A2 | 7/2009 | Yabe et al. |
| 2010/0187505 A1* | 7/2010 | Stoessel ............ C07C 39/12 |
| | | 568/14 |
| 2012/0126221 A1 | 5/2012 | Kitamura et al. |
| 2012/0126692 A1 | 5/2012 | Ise et al. |
| 2012/0205640 A1 | 8/2012 | Kai et al. |
| 2013/0240796 A1* | 9/2013 | Parham ............ C07D 491/02 |
| | | 544/333 |
| 2013/0292654 A1 | 11/2013 | Matsunaga et al. |
| 2014/0114069 A1 | 4/2014 | Kim et al. |
| 2015/0218191 A1 | 8/2015 | Sannomiya et al. |
| 2015/0380662 A1 | 12/2015 | Kim et al. |
| 2016/0329502 A1 | 11/2016 | Dyatkin et al. |
| 2017/0047522 A1 | 2/2017 | Noda et al. |
| 2017/0117488 A1 | 4/2017 | Ahn et al. |
| 2017/0244043 A1 | 8/2017 | Kim et al. |
| 2018/0123049 A1 | 5/2018 | Lee et al. |
| 2018/0145262 A1 | 5/2018 | Zeng et al. |
| 2018/0170914 A1 | 6/2018 | Miyata et al. |
| 2018/0248127 A1 | 8/2018 | Lee et al. |
| 2019/0019960 A1 | 1/2019 | Zink et al. |
| 2019/0237680 A1 | 8/2019 | Kim et al. |
| 2019/0288222 A1 | 9/2019 | Moon et al. |
| 2020/0044163 A1 | 2/2020 | Hung et al. |
| 2020/0115364 A1 | 4/2020 | Aguilera-Iparraguirre et al. |
| 2020/0331898 A1 | 10/2020 | Seifermann |
| 2022/0271233 A1 | 8/2022 | Yoon et al. |

FOREIGN PATENT DOCUMENTS

| | | |
|---|---|---|
| CN | 103764786 | 4/2014 |
| CN | 107667102 | 2/2018 |
| CN | 107880028 | 4/2018 |
| CN | 107935914 | 4/2018 |
| CN | 107954922 | 4/2018 |
| CN | 107987009 | 5/2018 |
| CN | 109251199 A | 1/2019 |
| CN | 112533900 A | 3/2021 |

(56) References Cited

FOREIGN PATENT DOCUMENTS

| | | |
|---|---|---|
| DE | 102016112377 | 1/2018 |
| JP | 2009-155300 A | 7/2009 |
| JP | 2009-158848 A | 7/2009 |
| JP | 2010-030937 | 2/2010 |
| JP | 4474493 | 6/2010 |
| JP | 4590020 | 12/2010 |
| JP | 4729642 | 7/2011 |
| JP | 2014-141571 | 8/2014 |
| JP | 2018-035129 | 3/2018 |
| KR | 10-2000-0051826 | 8/2000 |
| KR | 10-2010-0131939 | 12/2010 |
| KR | 10-2012-0018231 | 2/2012 |
| KR | 10-2012-0033711 | 4/2012 |
| KR | 10-2012-0098694 | 9/2012 |
| KR | 10-2012-0109744 | 10/2012 |
| KR | 10-2013-0020398 | 2/2013 |
| KR | 10-2013-0130236 | 12/2013 |
| KR | 10-2014-0014959 | 2/2014 |
| KR | 10-2014-0015240 | 2/2014 |
| KR | 10-1396171 | 5/2014 |
| KR | 10-2014-0139307 | 12/2014 |
| KR | 10-2015-0061174 | 6/2015 |
| KR | 10-2015-0063462 | 6/2015 |
| KR | 10-2015-0105201 | 9/2015 |
| KR | 10-2015-0129282 A | 11/2015 |
| KR | 10-2015-0139459 | 12/2015 |
| KR | 10-2016-0003362 | 1/2016 |
| KR | 10-2016-0041768 | 4/2016 |
| KR | 10-2016-0066339 | 6/2016 |
| KR | 10-2016-0129190 | 11/2016 |
| KR | 10-2017-0049291 | 5/2017 |
| KR | 10-2017-0060836 | 6/2017 |
| KR | 10-2017-0076292 A | 7/2017 |
| KR | 10-2017-0079348 | 7/2017 |
| KR | 10-2017-0097820 | 8/2017 |
| KR | 10-2017-0113808 | 10/2017 |
| KR | 10-2017-0116993 | 10/2017 |
| KR | 10-2018-0027468 | 3/2018 |
| KR | 10-2018-0047306 | 5/2018 |
| KR | 10-2018-0065276 | 6/2018 |
| KR | 10-2018-09963708 | 6/2018 |
| KR | 10-2018-0092035 | 8/2018 |
| KR | 10-2018-0098809 | 9/2018 |
| KR | 10-2018-0109747 | 10/2018 |
| KR | 10-1926771 | 12/2018 |
| KR | 10-2019-0008129 | 1/2019 |
| KR | 10-2019-0108094 | 9/2019 |
| KR | 10-2020-0047418 | 5/2020 |
| KR | 10-2020-0063053 | 6/2020 |
| TW | 2019-12640 | 4/2019 |
| WO | 2003-012890 A2 | 2/2003 |
| WO | 2003-012890 A3 | 8/2003 |
| WO | 2012-005362 | 1/2012 |
| WO | 2013-027906 | 2/2013 |
| WO | 2016-089080 | 6/2016 |
| WO | 2016-181846 | 11/2016 |
| WO | 2017-190885 | 11/2017 |
| WO | 2018/147638 A1 | 8/2018 |
| WO | 2018/237385 A1 | 12/2018 |
| WO | 2019-076844 | 4/2019 |
| WO | 2019/086297 A1 | 5/2019 |
| WO | 2019121112 | 6/2019 |

OTHER PUBLICATIONS

Braveenth, Ramanaskanda, and Kyu Yun Chai. "Triazine-acceptor-based green thermally activated delayed fluorescence materials for organic light-emitting diodes." Materials 12.16 (2019): 2646. (Year: 2019).*
Machine translation of KR 10-2010-0131939 A (publication date Dec. 2010). (Year: 2010).*
Lee, D. R. et al., "Bis(diphenyltriazine) as a new acceptor of efficient thermally activated delayed flourescent emitters," Dyes and Pigments (2018), doi: 10.1016/j.dyepig.2017.12.048, 32 pages.
Chan Seok Oh et al., "Dihedral Angle Control of Blue Thermally Activated Delayed Fluorescent Emitters through Donor Substitution Position for Efficient Reverse Intersystem Crossing", ACS Appl. Mater. Interfaces 10: 35420-35429 (2018).
Park, H. et al., "A directly coupled dual emitting core based molecular design of thermally activated delayed fluorescent emitters," J. Mater. Chem. C., 5:12143-12150 (2017).
U.S. Appl. No. 17/281,335.

* cited by examiner

[FIG. 1]
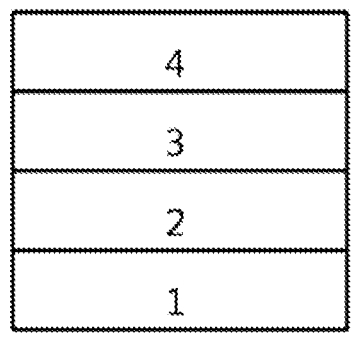
[FIG. 2]
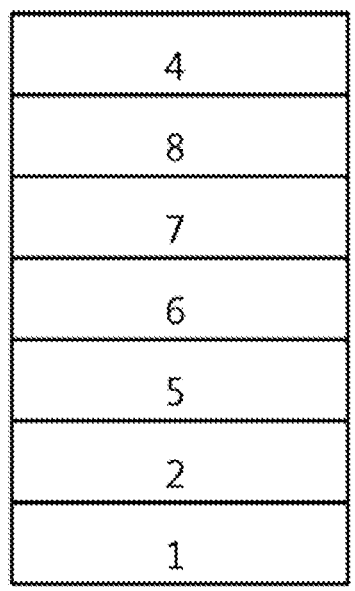

[FIG. 3]

| |
|---|
| 4 |
| 11 |
| 8 |
| 10 |
| 7 |
| 9 |
| 6 |
| 5 |
| 2 |
| 1 |

COMPOUND AND ORGANIC LIGHT EMITTING DEVICE COMPRISING THE SAME

CROSS-REFERENCE TO RELATED APPLICATION(S)

This application is a National Stage Application of International Application No. PCT/KR2019/015360 filed on Nov. 12, 2019, which claims priority to and the benefit of Korean Patent Application No. 10-2018-0148563 filed on Nov. 27, 2018 and Korean Patent Application No. 10-2019-0142728 filed on Nov. 8, 2019 in the Korean Intellectual Property Office, each of which is incorporated herein by reference in its entirety.

TECHNICAL FIELD

The present disclosure relates to a novel compound and to an organic light emitting device including the same.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer can be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in these organic light emitting devices.

PRIOR ART LITERATURE

Patent Literature (Patent Literature 0001) Korean Unexamined Patent Publication No. 10-2000-0051826

BRIEF DESCRIPTION

Technical Problem

It is an object of the present disclosure to provide a novel compound and an organic light emitting device including the same.

Technical Solution

Provided herein is a compound of Chemical Formula 1:

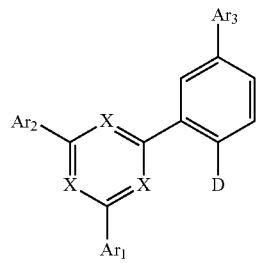

Chemical Formula 1 wherein, in Chemical Formula 1:
each X is independently N or CH, provided that at least one of X is N;
$Ar_1$ and $Ar_2$ are each independently a substituted or unsubstituted $C_{6-60}$ aryl or a substituted or unsubstituted $C_{5-60}$ heteroaryl containing any one or more heteroatoms selected from the group consisting of N, O and S;
$Ar_3$ is a substituted or unsubstituted $C_{5-60}$ heteroaryl containing at least one N;
D is a substituent group of any one of the following Chemical Formulas 2-1 to 2-3:

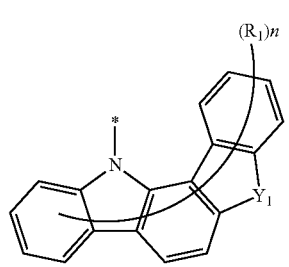

Chemical Formula 2-1

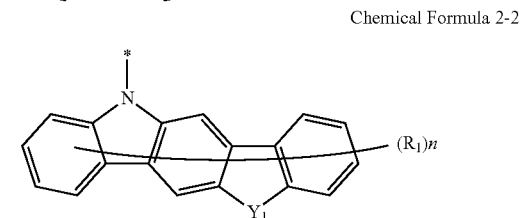

Chemical Formula 2-2

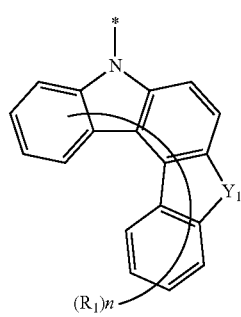

Chemical Formula 2-3 wherein, in Chemical Formulas 2-1 to 2-3:
$Y_1$ is O, S, $NR_2$, or $CR_3R_4$,
each n is independently an integer of 0 to 10;

each $R_1$ is independently hydrogen, deuterium, a substituted or unsubstituted $C_{1-60}$ alkyl, a substituted or unsubstituted $C_{3-60}$ cycloalkyl, a substituted or unsubstituted $C_{6-60}$ aryl, or a substituted or unsubstituted $C_{5-60}$ heteroaryl containing one or more heteroatoms selected from the group consisting of N, O and S; and $R_2$ to $R_4$ are each independently a substituted or unsubstituted $C_{1-60}$ alkyl or a substituted or unsubstituted $C_{6-60}$ aryl.

Also provided herein is an organic light emitting device including: a first electrode; a second electrode that is provided opposite to the first electrode; and one or more organic material layers that are provided between the first electrode and the second electrode, wherein one or more layers of the organic material layers include the compound of Chemical Formula 1.

Advantageous Effects

The above-mentioned compound of Chemical Formula 1 can be used as a material of an organic material layer of an organic light emitting device and can improve the efficiency, achieve low driving voltage and/or improve lifetime characteristics in the organic light emitting device. In particular, the compound of Chemical Formula 1 can be used as a hole injection material, a hole transport material, a hole injection and transport material, a light emitting material, an electron transport material, or an electron injection material.

BRIEF DESCRIPTION OF THE DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, a light emitting layer 7, an electron transport layer 8, and a cathode 4.

FIG. 3 shows an example of an organic light emitting device comprising a substrate 1, an anode 2, a hole injection layer 5, a hole transport layer 6, an electron blocking layer 9, a light emitting layer 7, a hole blocking layer 10, an electron transport layer 8, an electron injection layer 11, and a cathode 4.

DETAILED DESCRIPTION OF THE EMBODIMENTS

Hereinafter, embodiments of the present disclosure will be described in more detail to facilitate understanding of the invention.

One embodiment of the invention provides the compound of Chemical Formula 1.

As used herein, the notations,

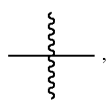

┆ or ┆ mean a bond linked to another substituent group.

As used herein, the term "substituted or unsubstituted" means being unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, or a heterocyclic group containing at least one of N, O and S atoms, or being unsubstituted or substituted with a substituent group to which two or more substituents are linked among the substituents exemplified above. For example, "the substituent to which two or more substituents are linked" can be a biphenyl group. That is, the biphenyl group can also be an aryl group and can be interpreted as a substituent group to which two phenyl groups are linked.

In the present specification, the number of carbon atoms of a carbonyl group is not particularly limited, but is preferably 1 to 40. Specifically, the carbonyl group can be a compound having the following structural formulae but is not limited thereto:

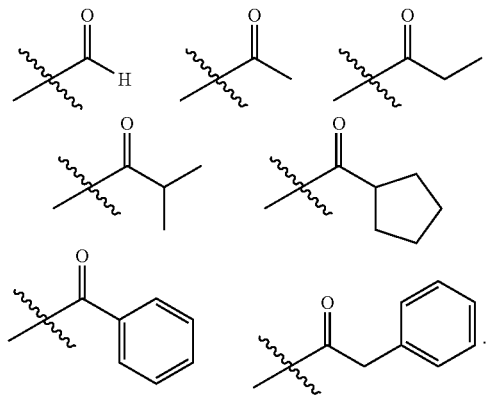

In the present specification, an ester group can have a structure in which oxygen of the ester group can be substituted with a straight-chain, branched-chain, or cyclic alkyl group having 1 to 25 carbon atoms, or an aryl group having 6 to 25 carbon atoms. Specifically, the ester group can be a compound having the following structural formulae, but is not limited thereto:

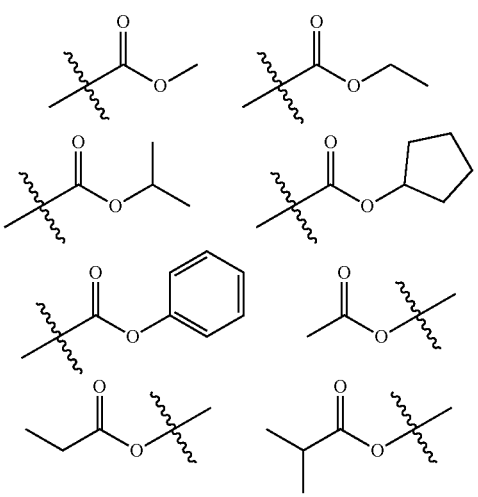

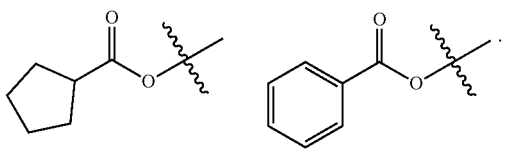

In the present specification, the number of carbon atoms of an imide group is not particularly limited, but is preferably 1 to 25. Specifically, the imide group can be a compound having the following structural formulae, but is not limited thereto:

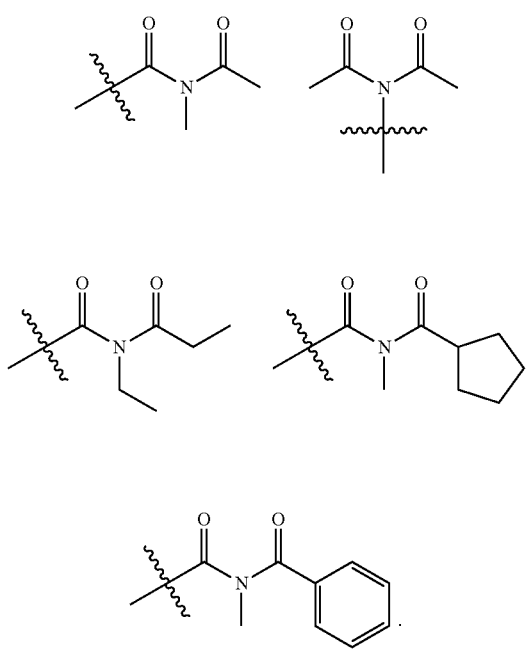

In the present specification, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present specification, a boron group specifically includes a trimethylboron group, a triethylboron group, a t-butyldimethylboron group, a triphenylboron group, and a phenylboron group, but is not limited thereto.

In the present specification, examples of a halogen group include fluorine, chlorine, bromine, or iodine.

In the present specification, the alkyl group can be a straight-chain or branched chain, and the number of carbon atoms thereof is not particularly limited, but is preferably 1 to 40. According to one embodiment, the number of carbon atoms of the alkyl group is 1 to 20. According to another embodiment, the number of carbon atoms of the alkyl group is 1 to 10. According to another embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the alkenyl group can be a straight chain or branched chain, and the number of carbon atoms thereof is not particularly limited, but is preferably 2 to 40. According to one embodiment, the number of carbon atoms of the alkenyl group is 2 to 20. According to another embodiment, the number of carbon atoms of the alkenyl group is 2 to 10. According to still another embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the number of carbon atoms of the cycloalkyl group is 3 to 30. According to another embodiment, the number of carbon atoms of the cycloalkyl group is 3 to 20. According to still another embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an aryl group is not particularly limited, but preferably has 6 to 60 carbon atoms, and can be a monocyclic aryl group or a polycyclic aryl group. According to one embodiment, the number of carbon atoms of the aryl group is 6 to 30. According to one embodiment, the number of carbon atoms of the aryl group is 6 to 20. The aryl group can be a phenyl group, a biphenyl group, a terphenyl group or the like as the monocyclic aryl group, but is not limited thereto. Examples of the polycyclic aryl group include a naphthyl group, an anthracenyl group, a phenanthryl group, a pyrenyl group, a perylenyl group, a chrysenyl group, a fluorenyl group or the like, but is not limited thereto.

In the present specification, a fluorenyl group can be substituted, and two substituent groups can be connected with each other to form a spiro structure. In the case where the fluorenyl group is substituted,

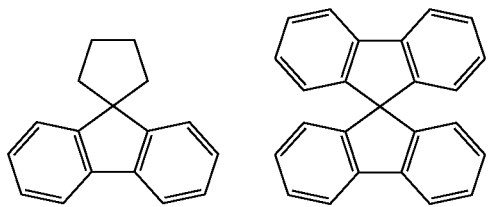

-continued

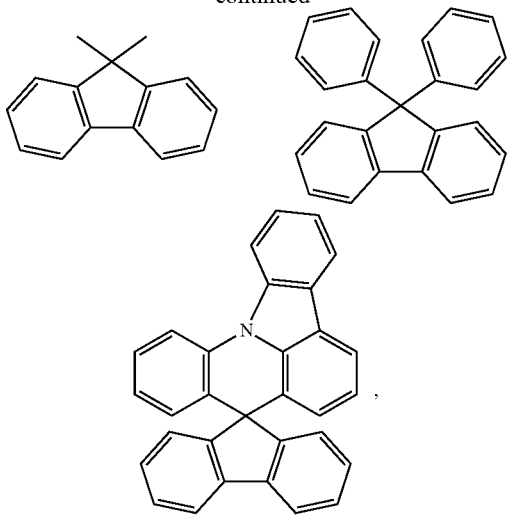

and the like can be formed. However, the structure is not limited thereto.

In the present specification, a heterocyclic group is a heterocyclic group including one or more of O, N, Si, and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazol group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group and the alkylamine group is the same as the aforementioned examples of the alkyl group. In the present specification, the heteroaryl in the heteroarylamine can be applied to the aforementioned description of the heteroaryl. In the present specification, the alkenyl group in the aralkenyl group is the same as the aforementioned examples of the alkenyl group. In the present specification, the aforementioned description of the aryl group can be applied except that the arylene is a divalent group. In the present specification, the aforementioned description of the heteroaryl can be applied except that the heteroarylene is a divalent group. In the present specification, the aforementioned description of the aryl group or cycloalkyl group can be applied except that the hydrocarbon ring is not a monovalent group but formed by combining two substituent groups. In the present specification, the aforementioned description of the heterocyclic group can be applied, except that the heterocycle is not a monovalent group but formed by combining two substituent groups.

Preferably, the Chemical Formula 1 can be any one of the following Chemical Formulae 1-1 to 1-3:

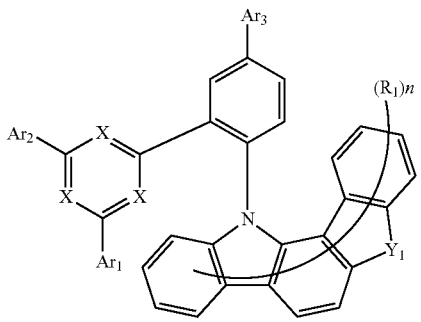

Chemical Formula 1-1

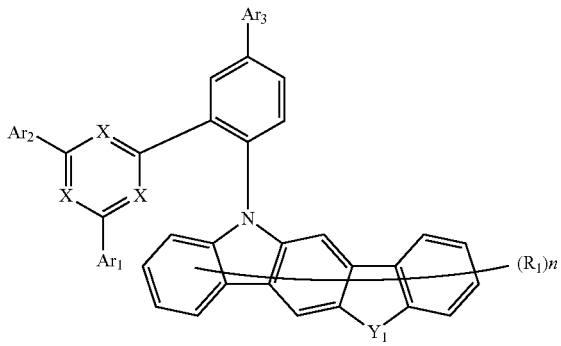

Chemical Formula 1-2

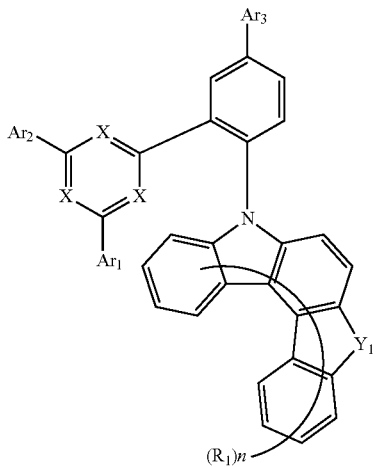

Chemical Formula 1-3 wherein, in Chemical Formulas 1-1 to 1-3:
X, $Ar_1$ to $Ar_3$, $Y_1$, $R_1$ and n are as defined above.
Preferably, each n can be independently 0, 1 or 2.
Preferably, $Y_1$ is O; S; $NR_2$, or $CR_3R_4$, where the $R_2$ to $R_4$ are each independently a substituted or unsubstituted $C_{1-10}$ alkyl or a substituted or unsubstituted $C_{6-20}$ aryl, and more preferably, $Y_1$ can be O, S, $N(C_6H_5)$, $N(C_6D_5)$, or $C(CH_3)_2$.
Preferably, $Ar_1$ and $Ar_2$ can be each independently a substituted or unsubstituted $C_{6-20}$ aryl, and more preferably, $Ar_1$ and $Ar_2$ can be each independently phenyl, biphenyl, naphthyl, or a phenyl group substituted with 1 to 5 deuterium.
Preferably, $Ar_3$ can be a substituted or unsubstituted $C_{5-30}$ heteroaryl containing at least one N, and more preferably, $Ar_3$ can be a substituent group of any one of the following Chemical Formulas 3-1 to 3-5:

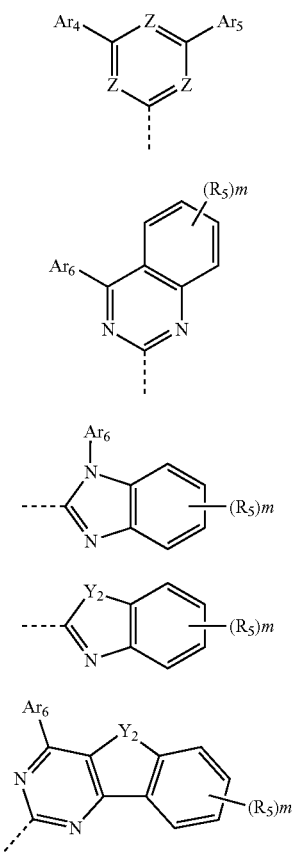

Chemical Formula 3-1

Chemical Formula 3-2

Chemical Formula 3-3

Chemical Formula 3-4

Chemical Formula 3-5 wherein, in Chemical Formulas 3-1 to 3-5:

each Z is independently N or CH, provided that at least one of Z is N;

$Ar_4$ and $Ar_5$ are each independently a substituted or unsubstituted $C_{6-60}$ aryl or a substituted or unsubstituted $C_{5-60}$ heteroaryl containing any one or more heteroatoms selected from the group consisting of N, O and S;

$Ar_6$ is a substituted or unsubstituted $C_{6-60}$ aryl;

$Y_2$ is O or S, each m is independently an integer of 0 to 4; and each $R_5$ is independently hydrogen, deuterium, a substituted or unsubstituted $C_{1-60}$ alkyl, a substituted or unsubstituted $C_{3-60}$ cycloalkyl, a substituted or unsubstituted $C_{6-60}$ aryl, or a substituted or unsubstituted $C_{5-60}$ heteroaryl containing one or more heteroatoms selected from the group consisting of N, O and S.

Preferably, the Chemical Formula 3-1 can be any one substituent selected from the group consisting of the following substituents:

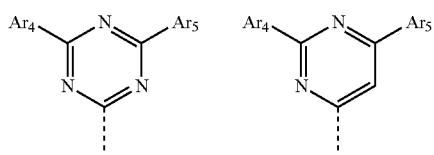

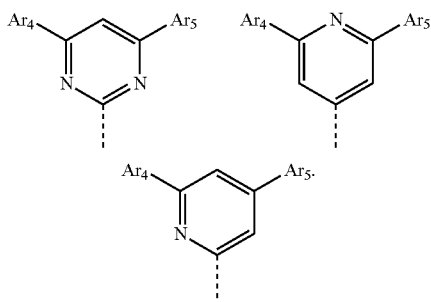

-continued

Preferably, $Ar_4$ and $Ar_5$ are each independently a substituted or unsubstituted $C_{6-20}$ aryl or a substituted or unsubstituted $C_{5-30}$ heteroaryl containing any one or more heteroatoms selected from the group consisting of N, O and S, and more preferably, $Ar_4$ and $Ar_5$ can be each independently any one substituent selected from the group consisting of the following substituents:

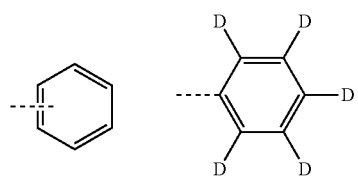

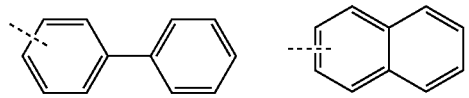

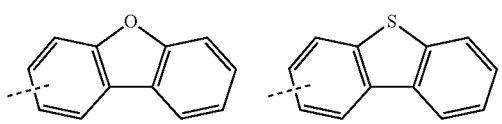

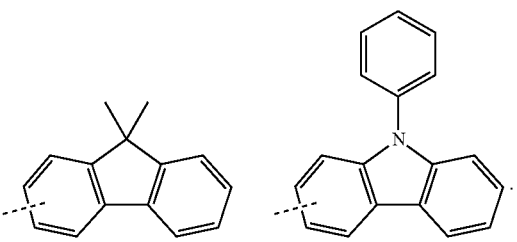

Preferably, $Ar_6$ can be a substituted or unsubstituted $C_{6-20}$ aryl, and more preferably, $Ar_6$ can be phenyl; biphenyl; or a phenyl group substituted with 1 to 5 deuterium.

Preferably, each m can be independently 0, 1 or 2.

For example, the compound can be selected from the group consisting of the following compounds:
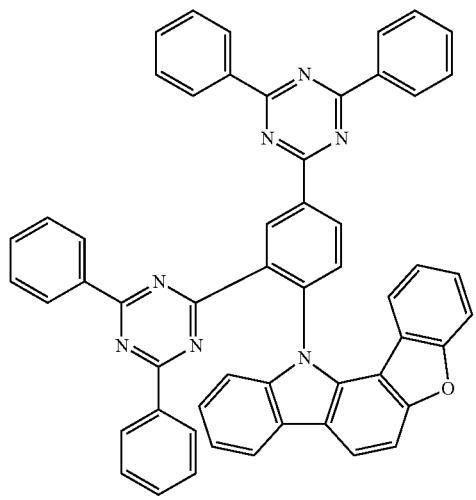
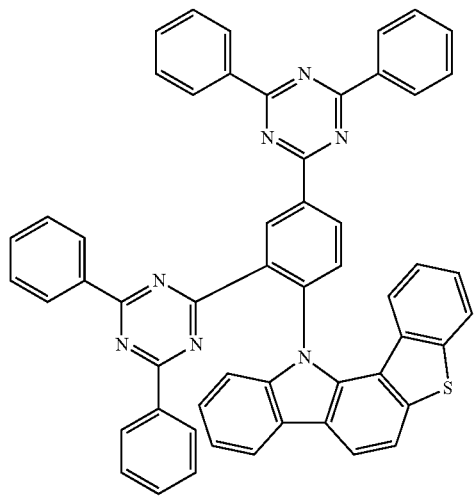
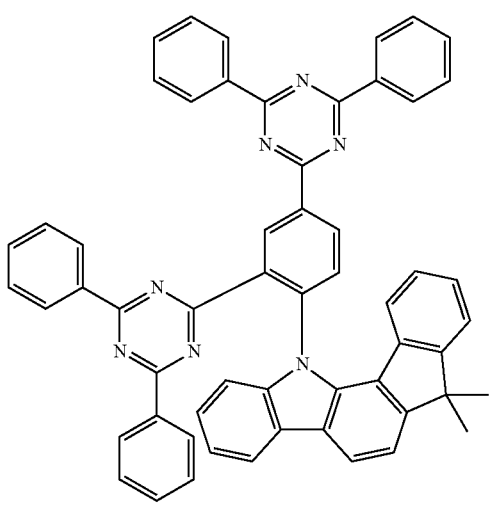
-continued
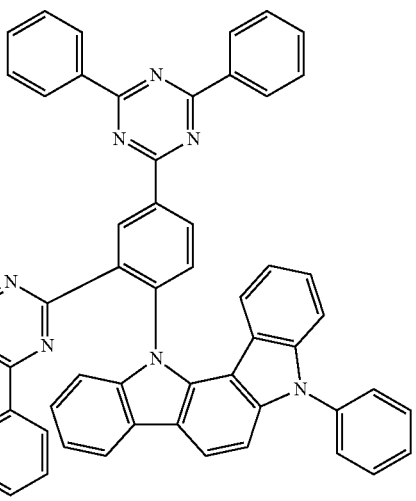
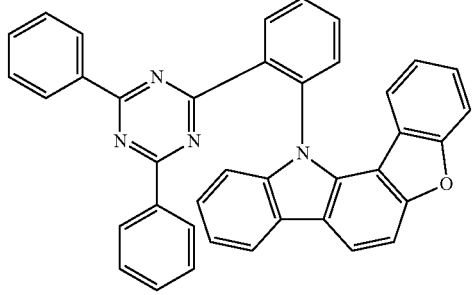
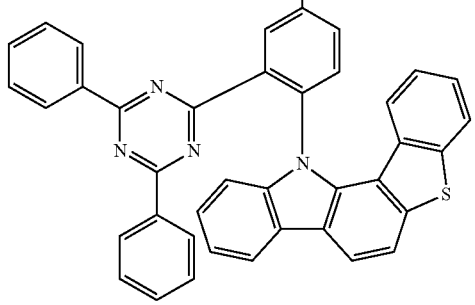

-continued
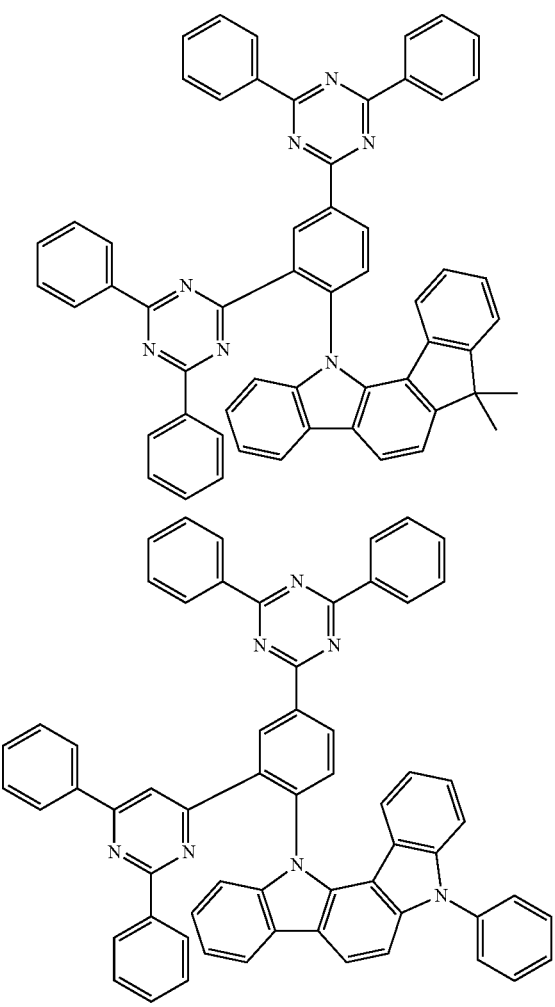
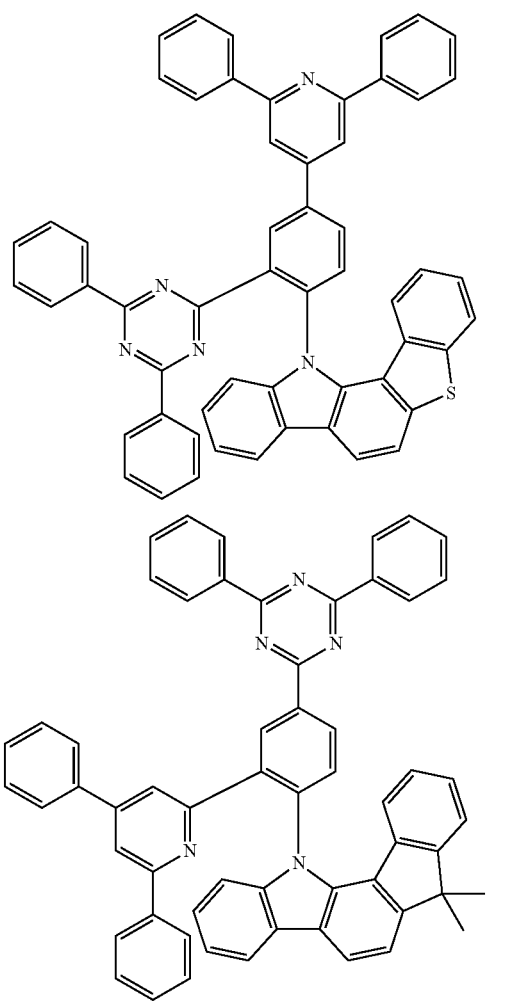
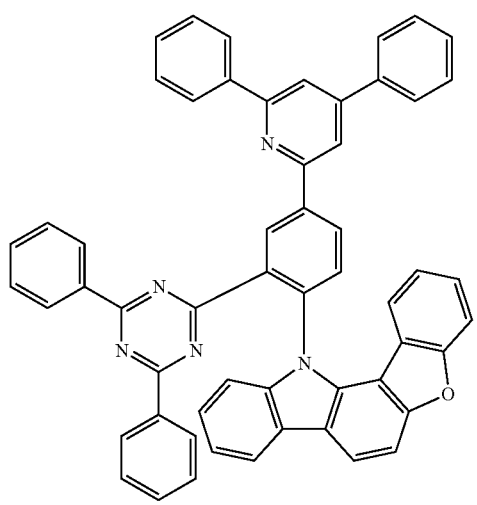

15
-continued
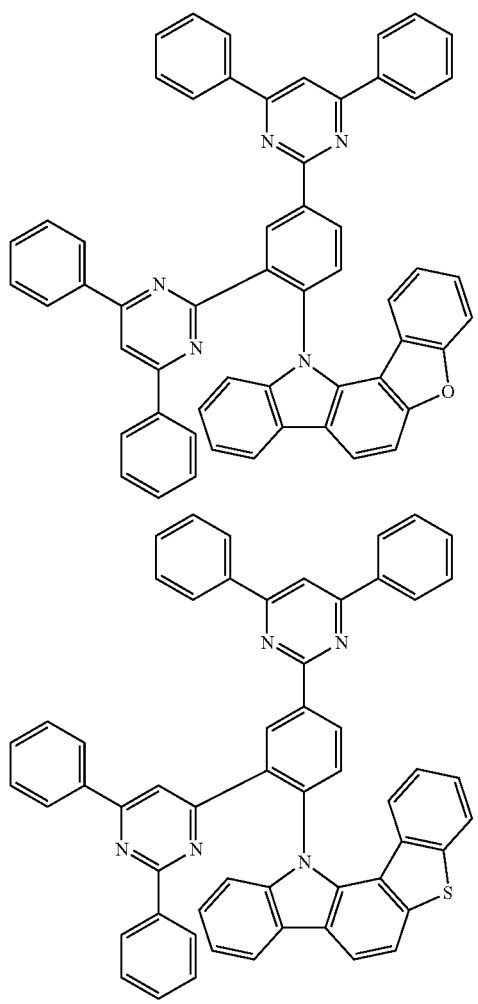
16
-continued
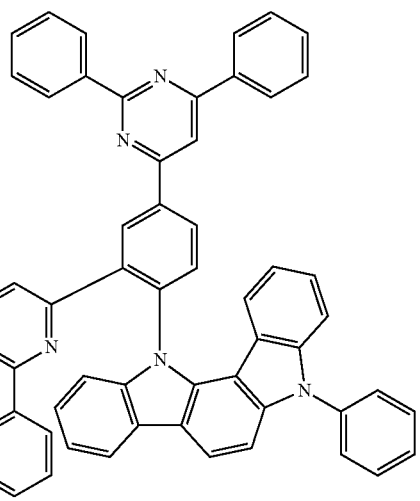
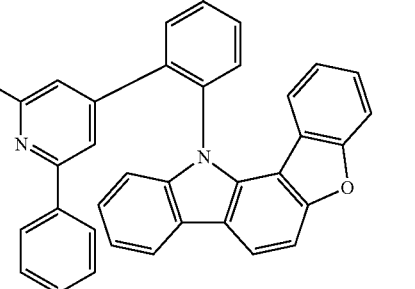
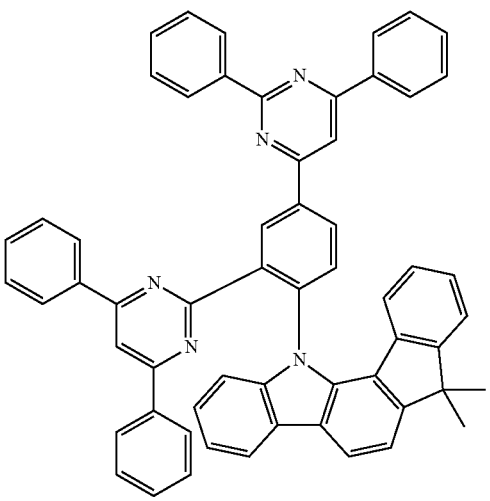
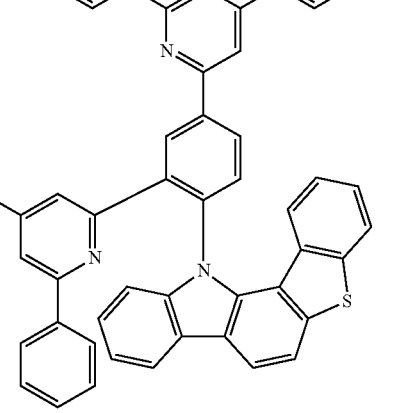

17
-continued
18
-continued
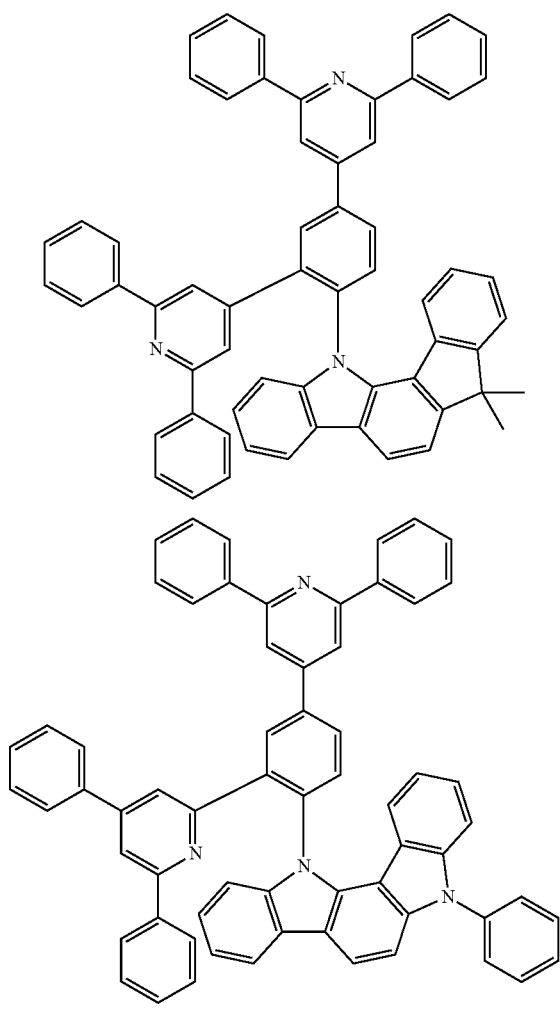
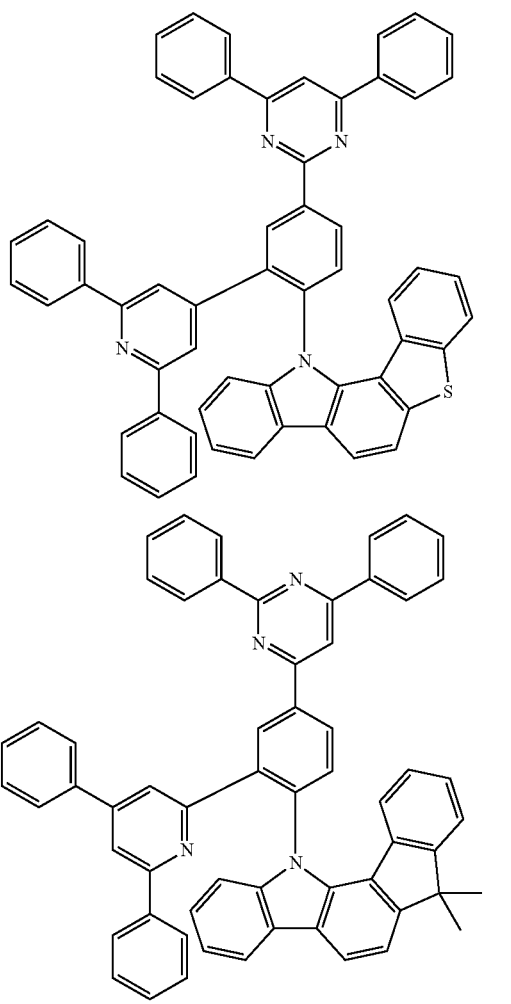
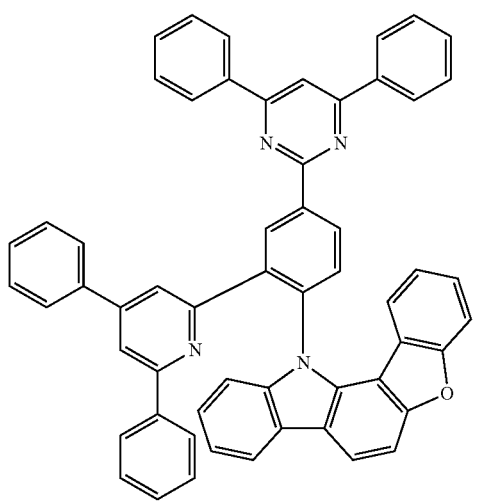

-continued
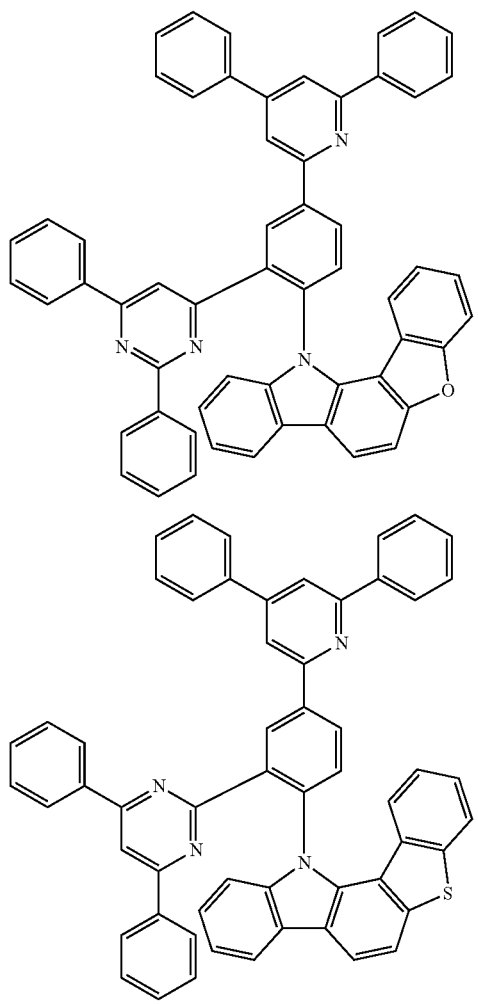
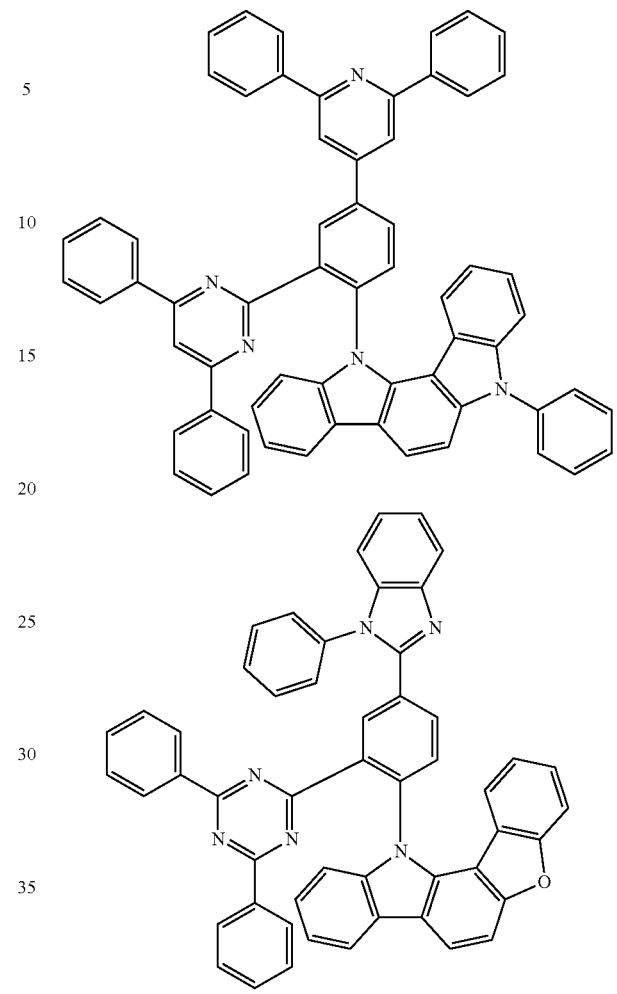
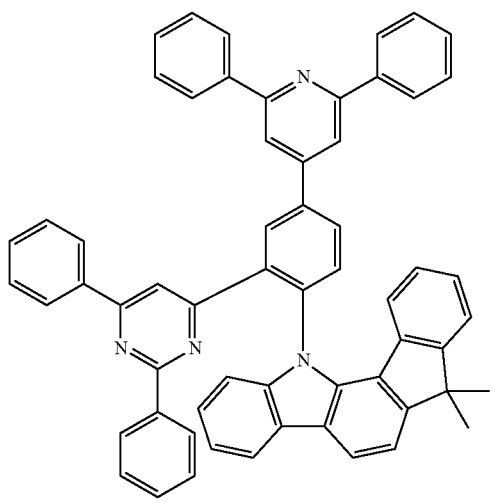
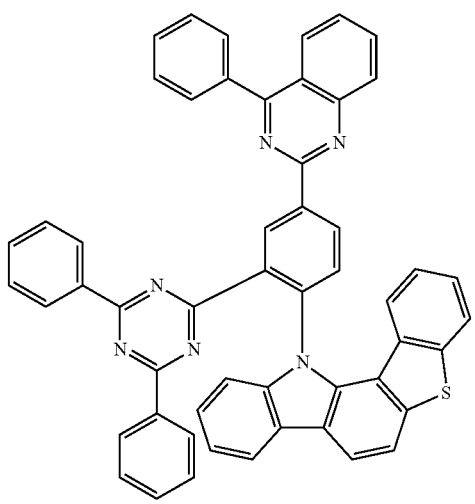

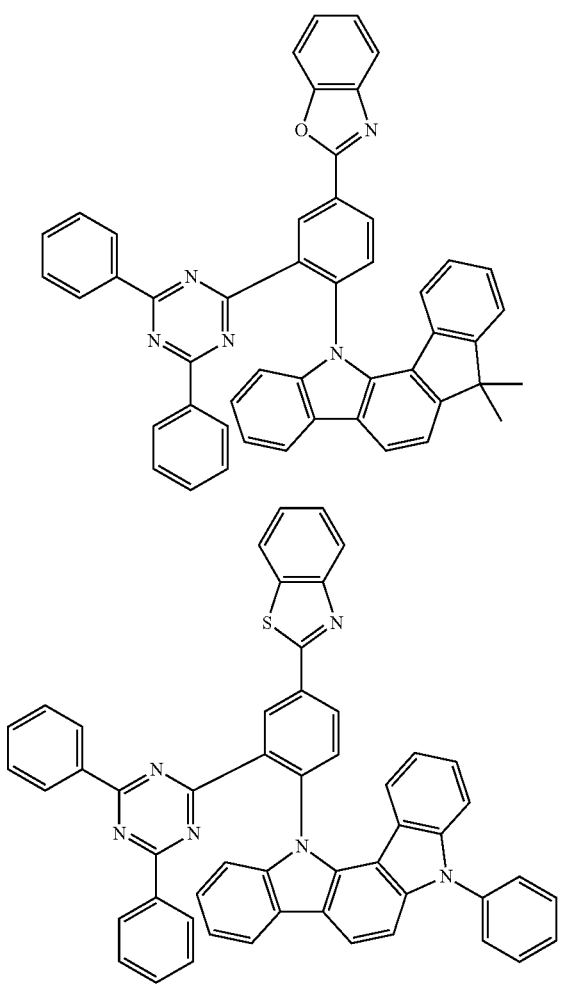
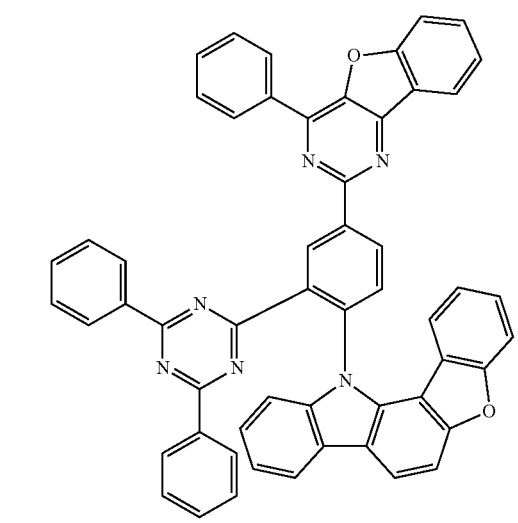
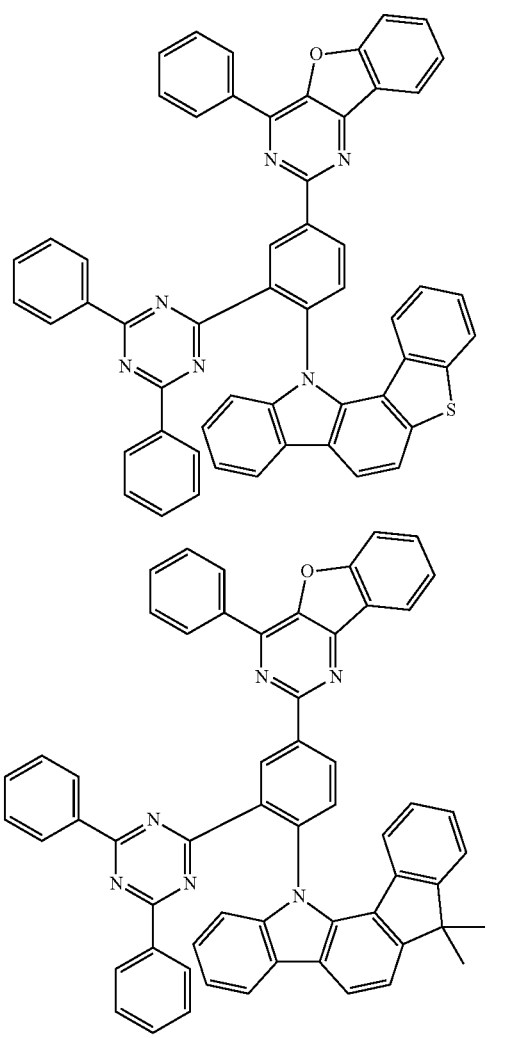
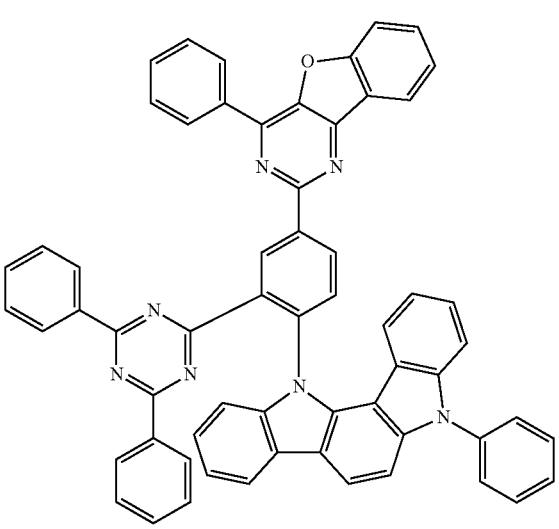

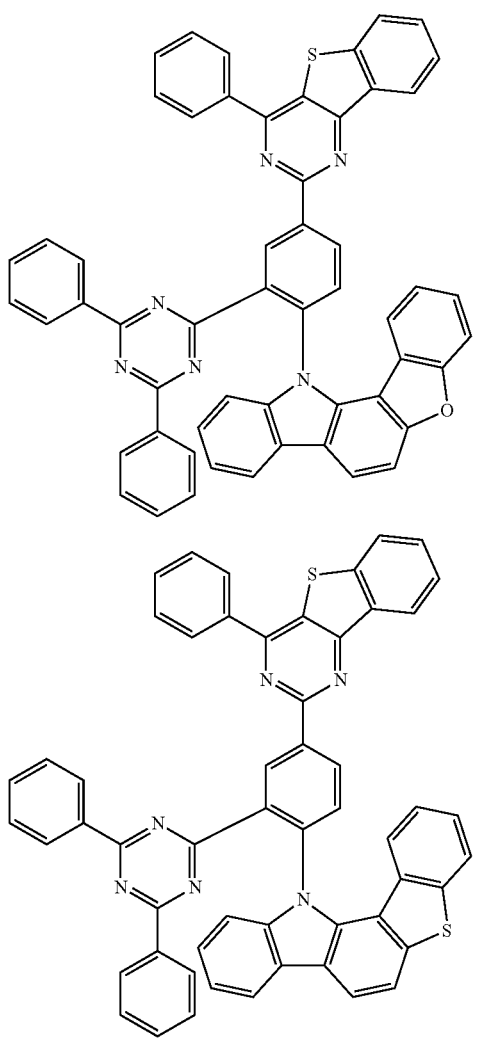
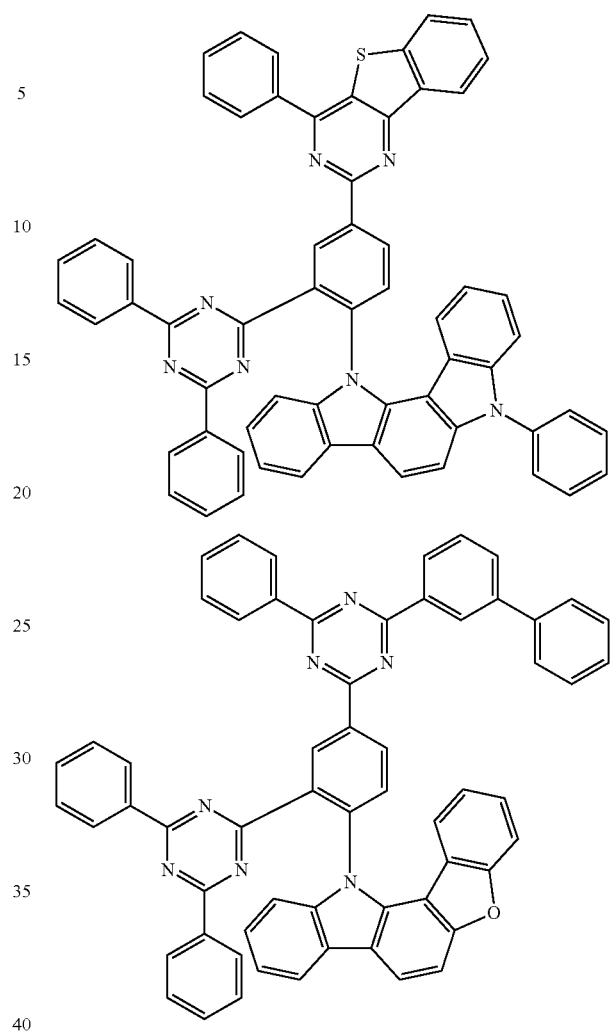
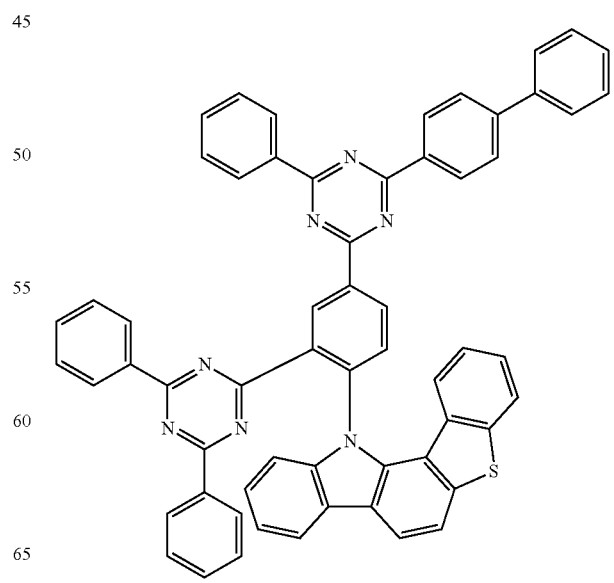

-continued
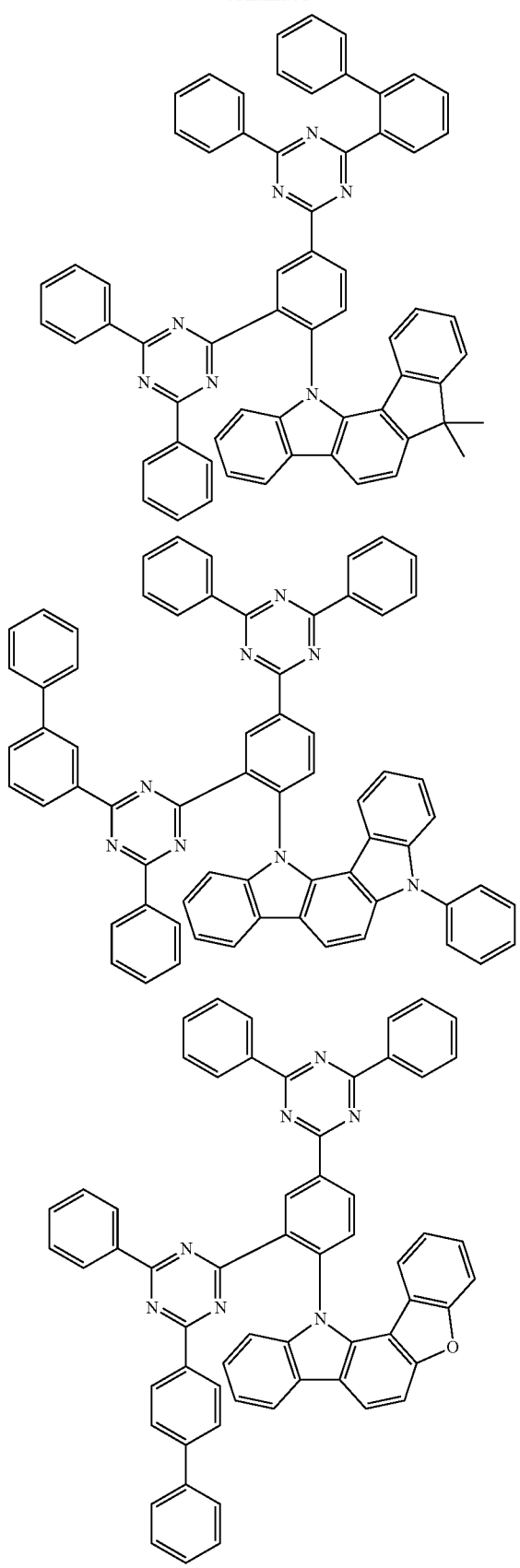
-continued
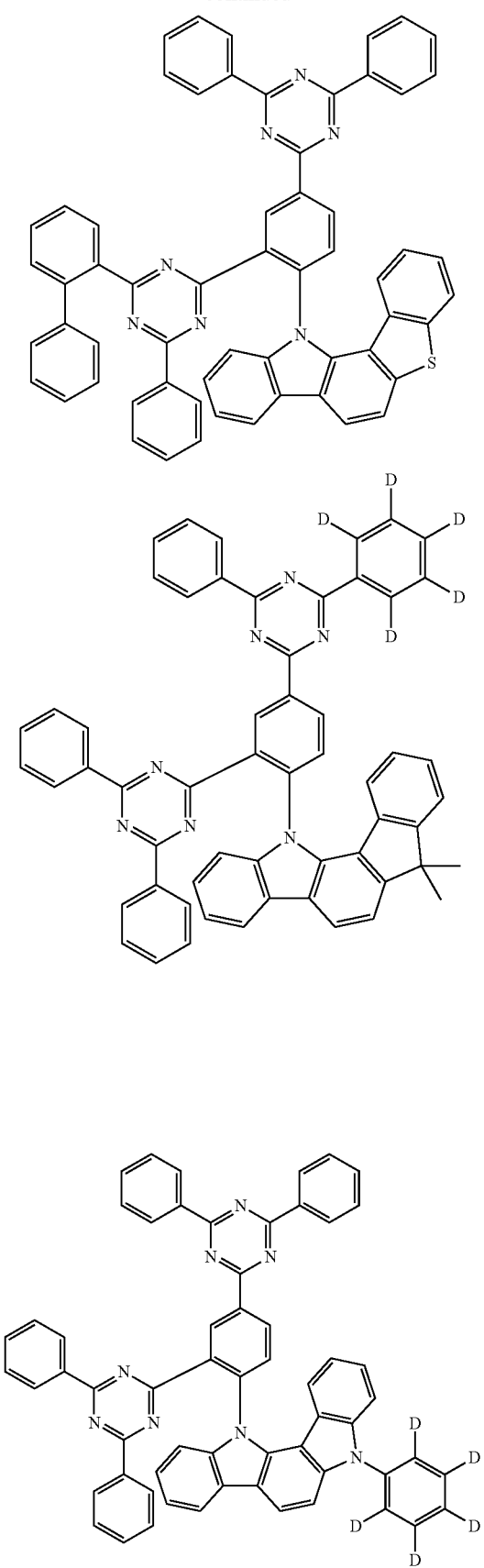

-continued
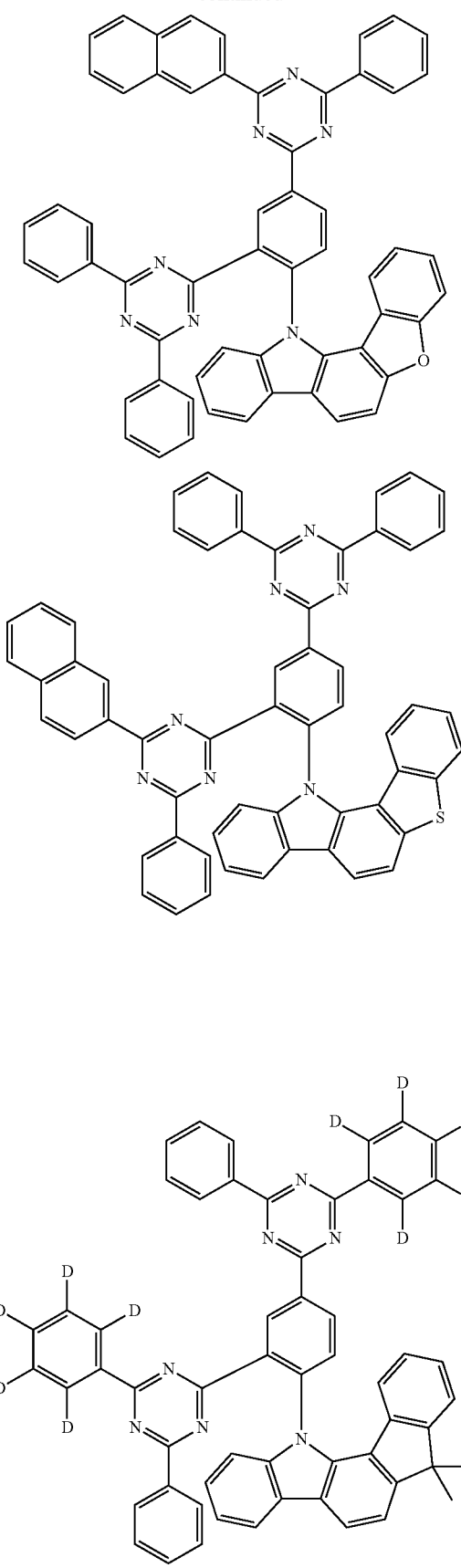
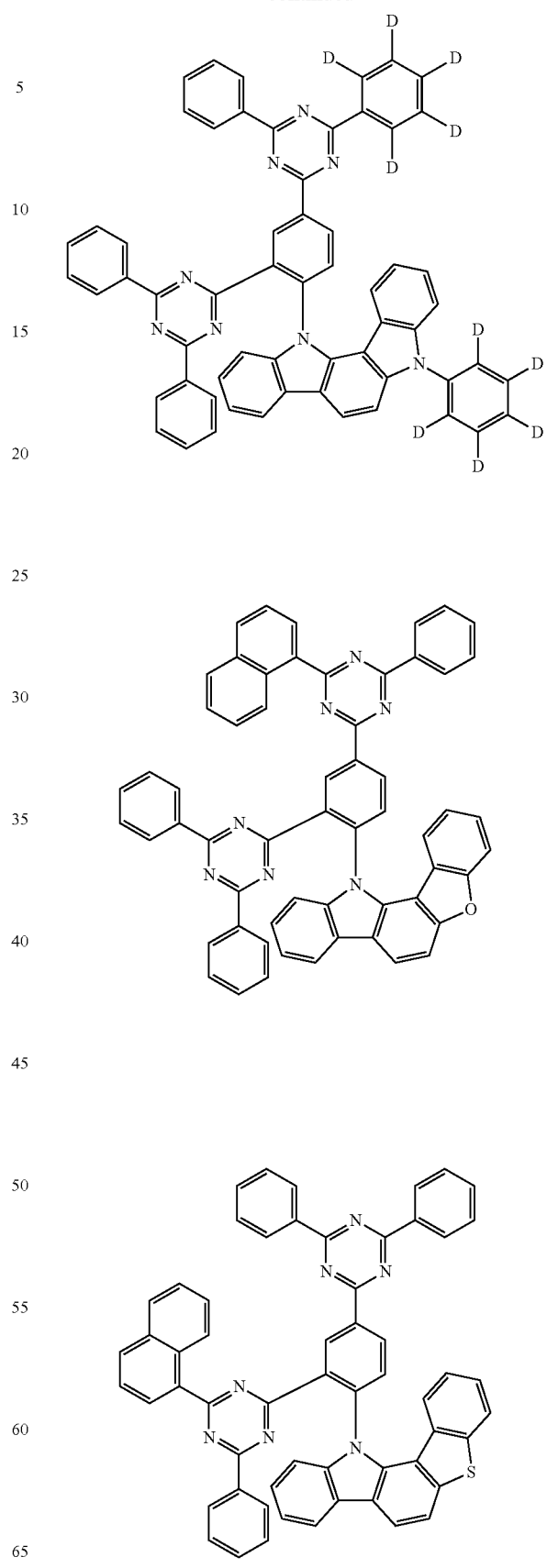

29
-continued
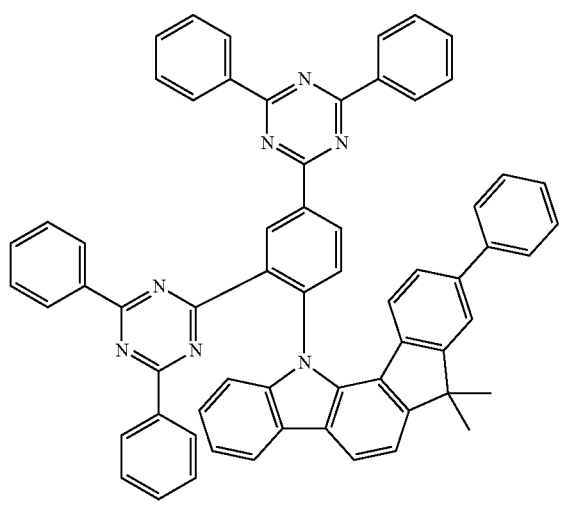
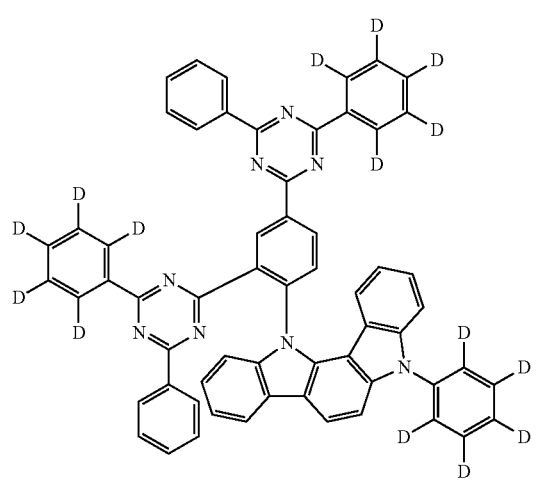
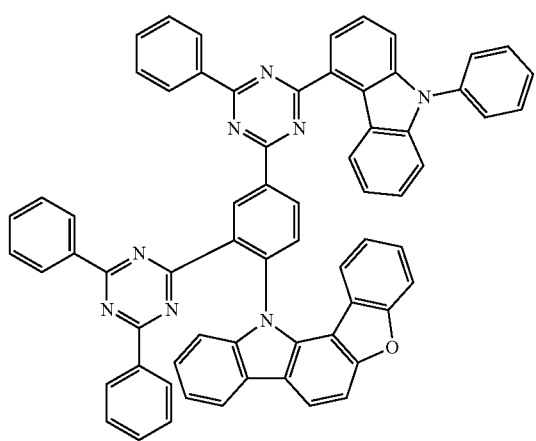
30
-continued
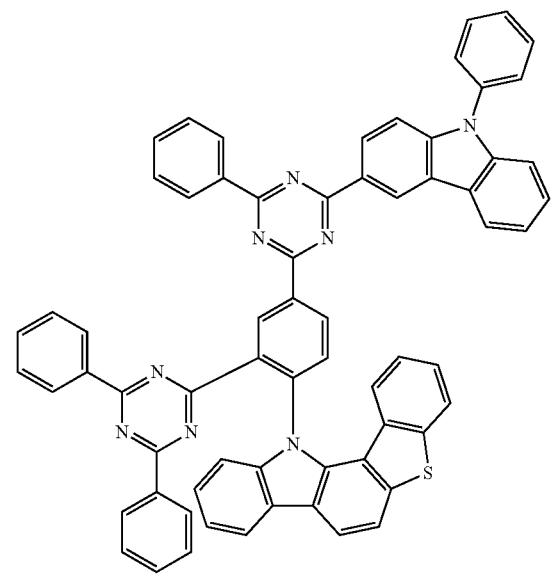
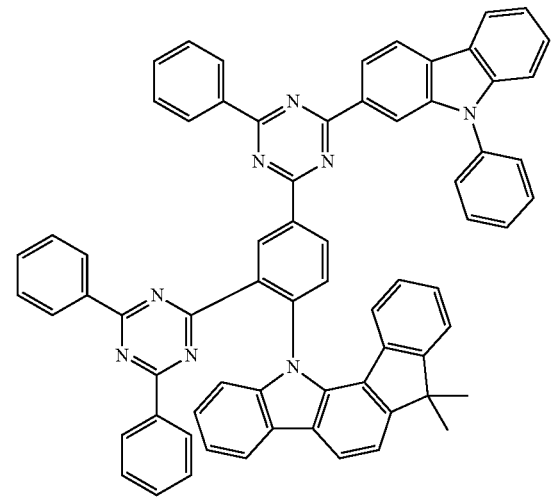
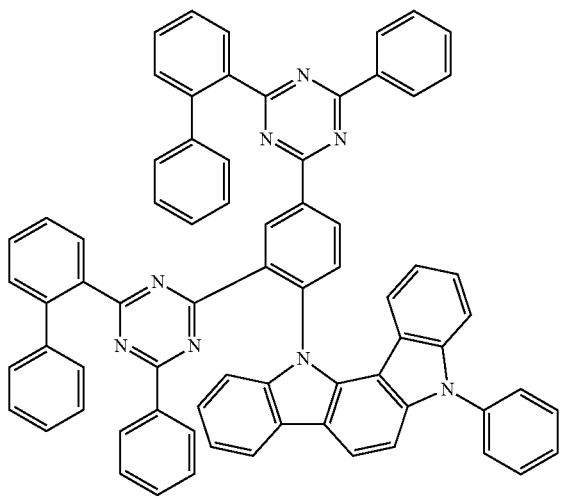

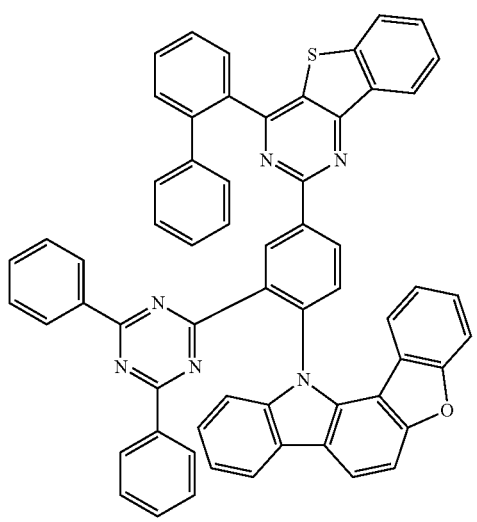
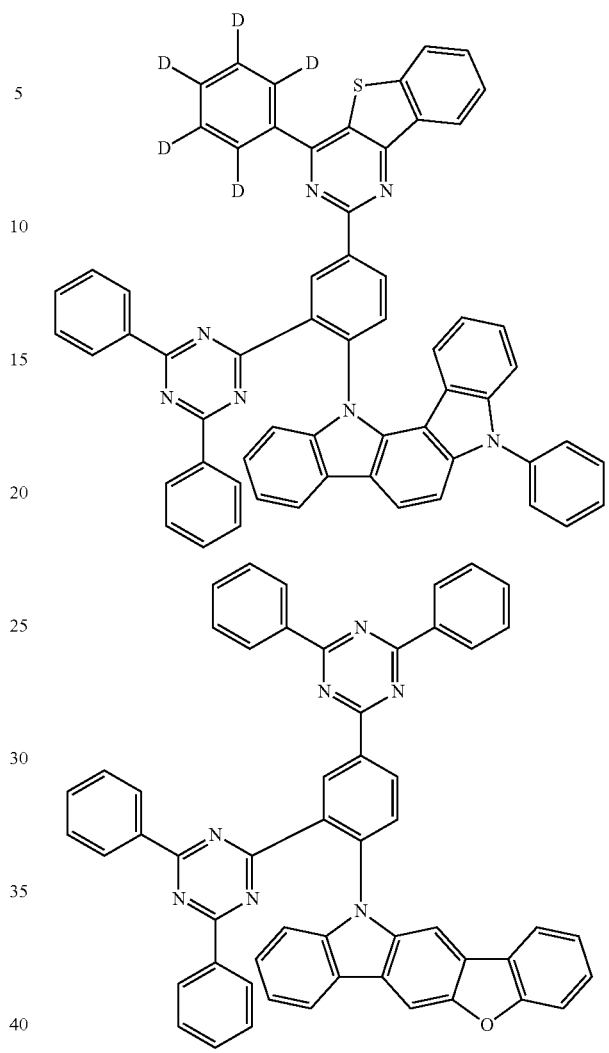
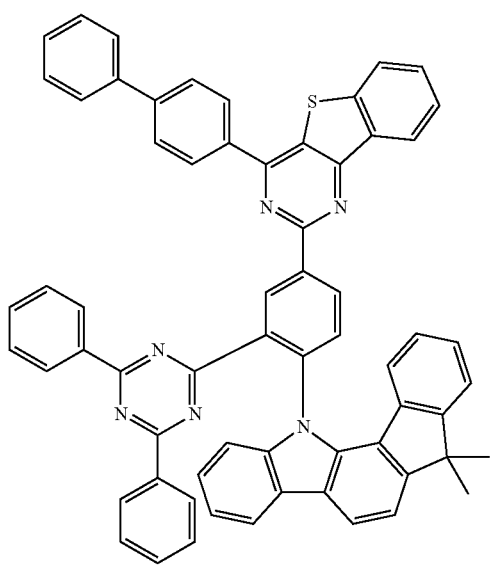

33
-continued
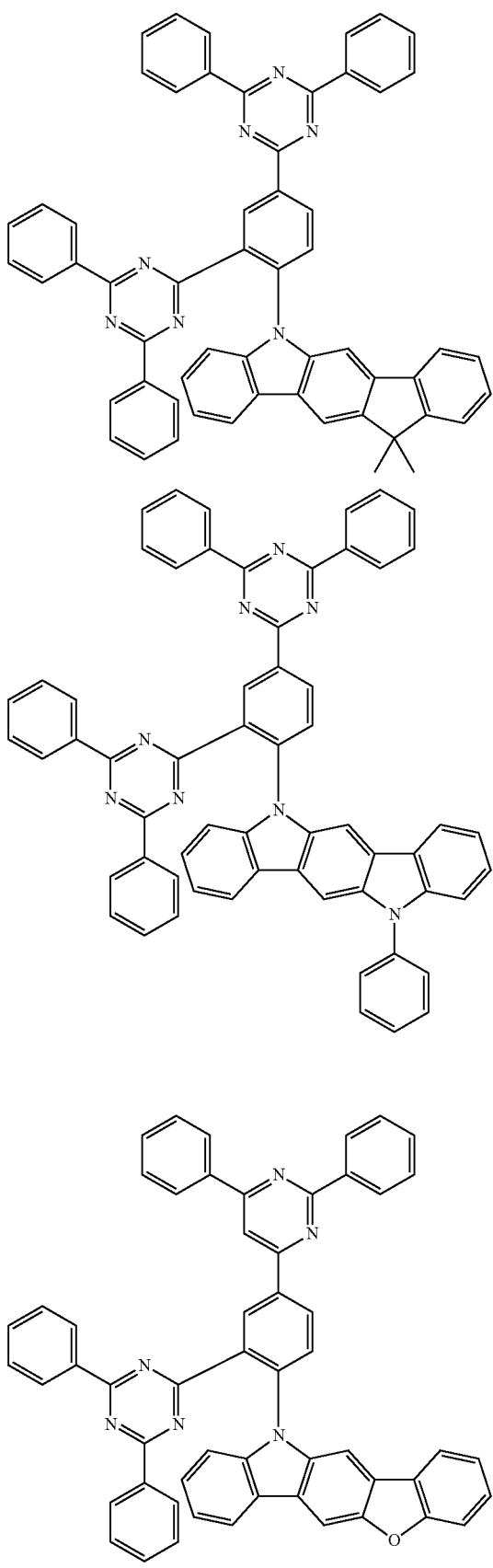
34
-continued
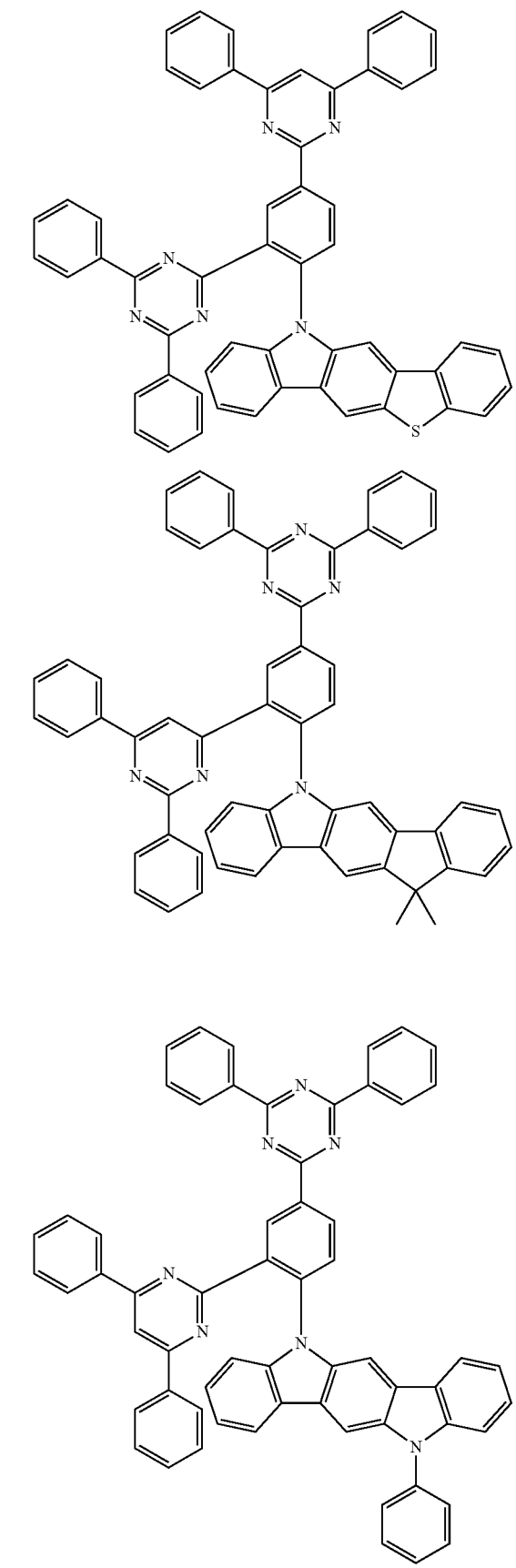

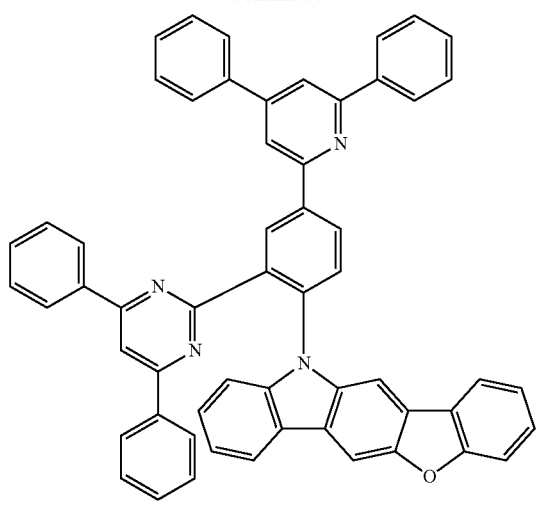
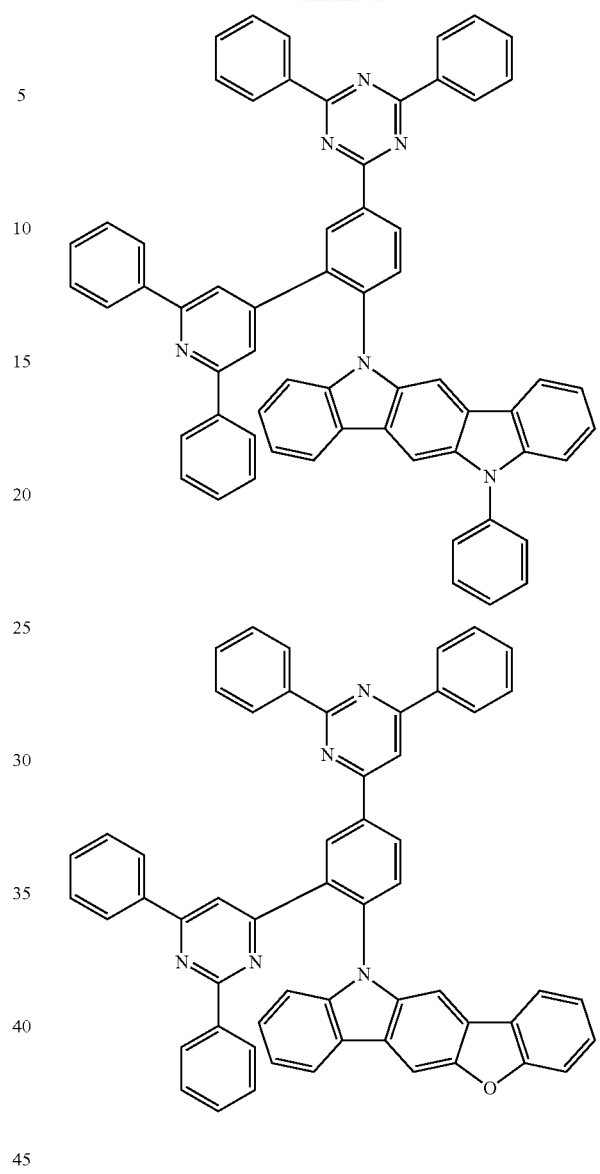
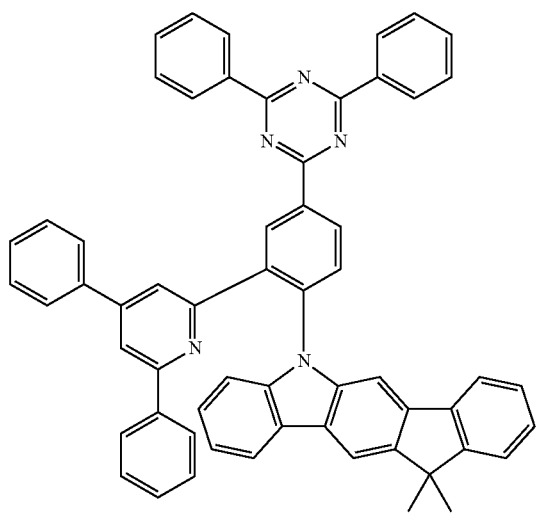 [SMILES: CC1(C)c2ccccc2-c2cc3c(cc21)c1ccccc1n3-c1ccc(-c2nc(-c3ccccc3)nc(-c3ccccc3)n2)cc1-c1nc(-c2ccccc2)nc(-c2ccccc2)n1]
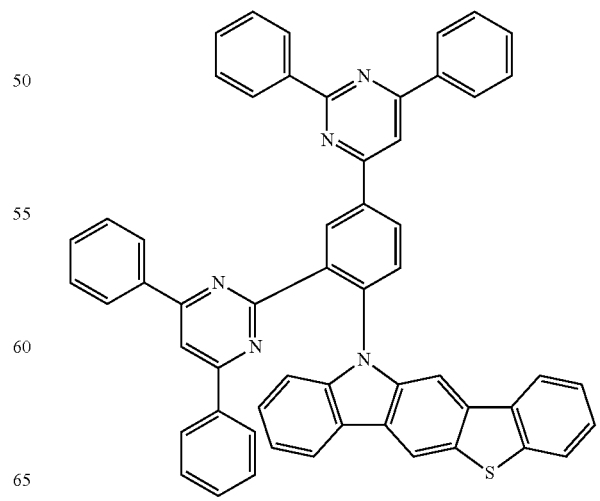

37
-continued
38
-continued
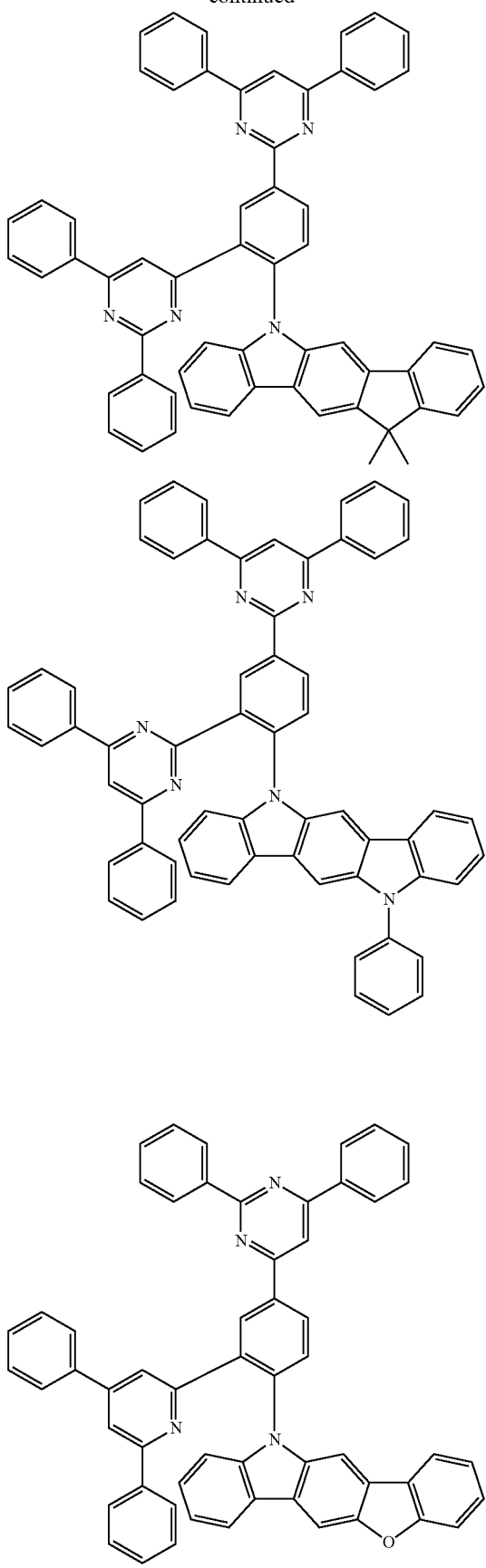
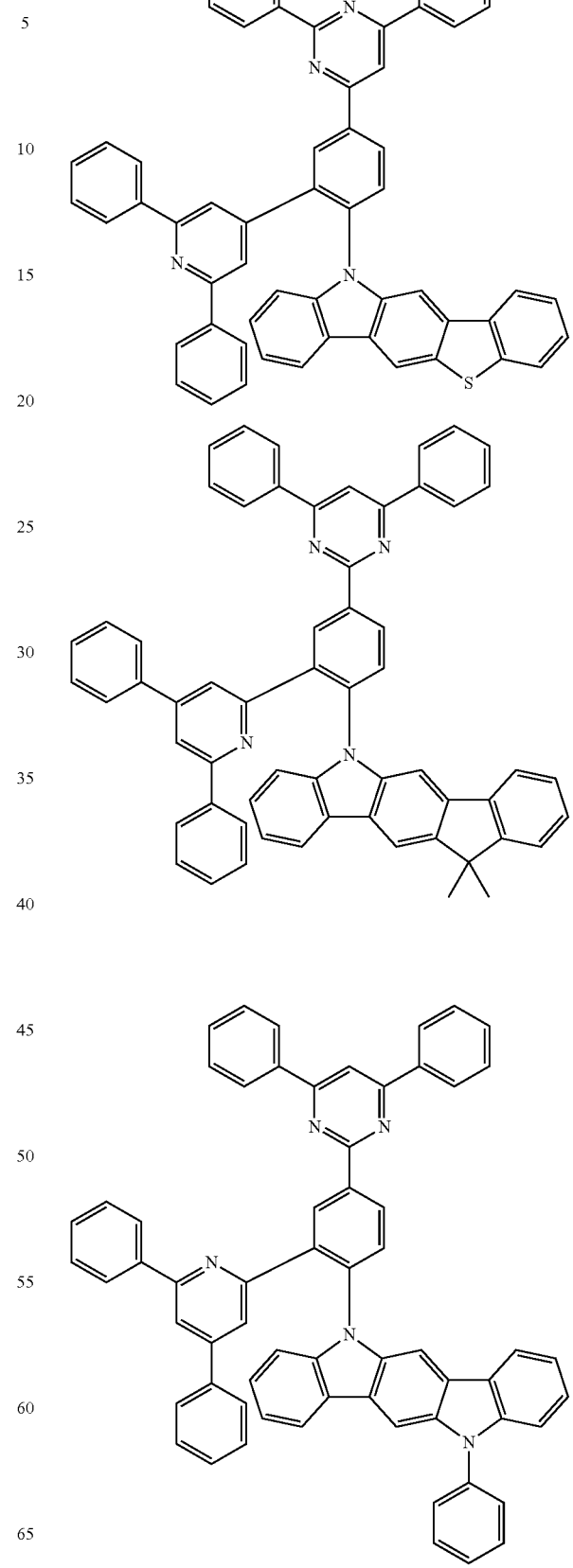

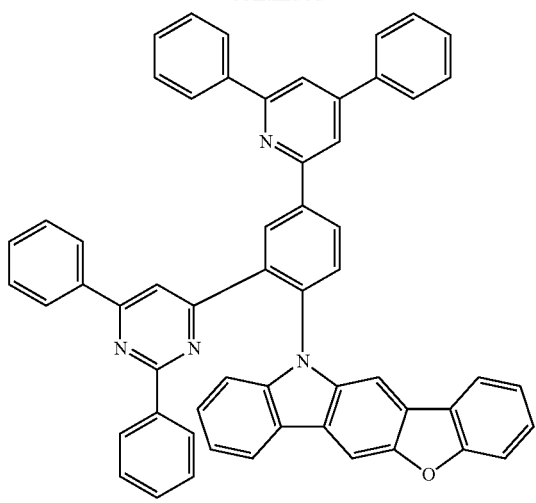
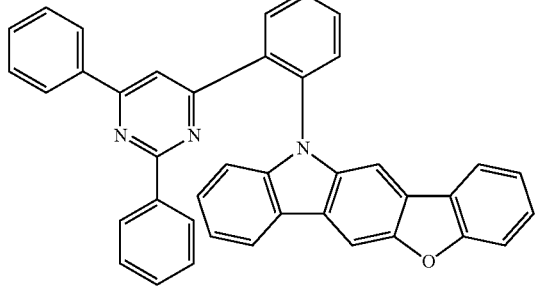
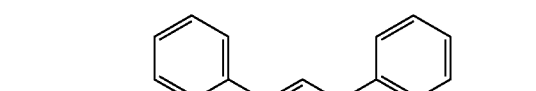
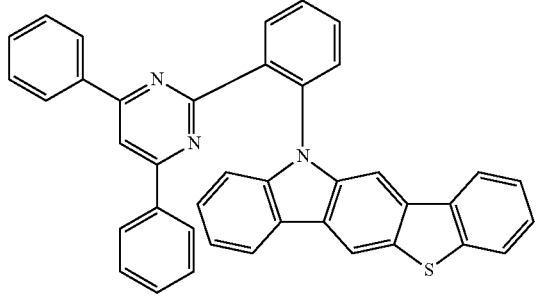
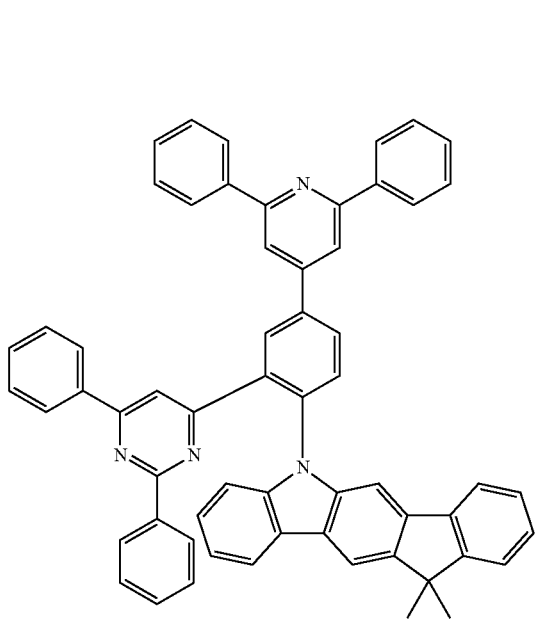
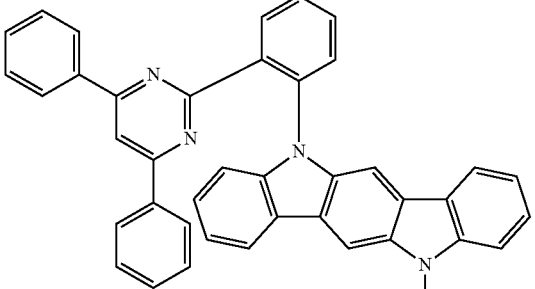
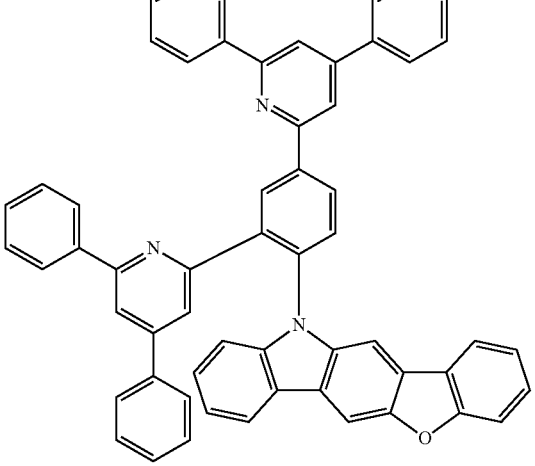
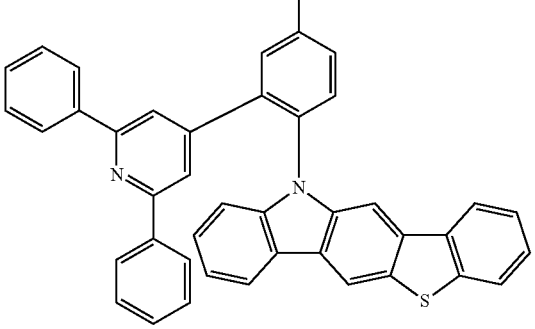

41
-continued
42
-continued
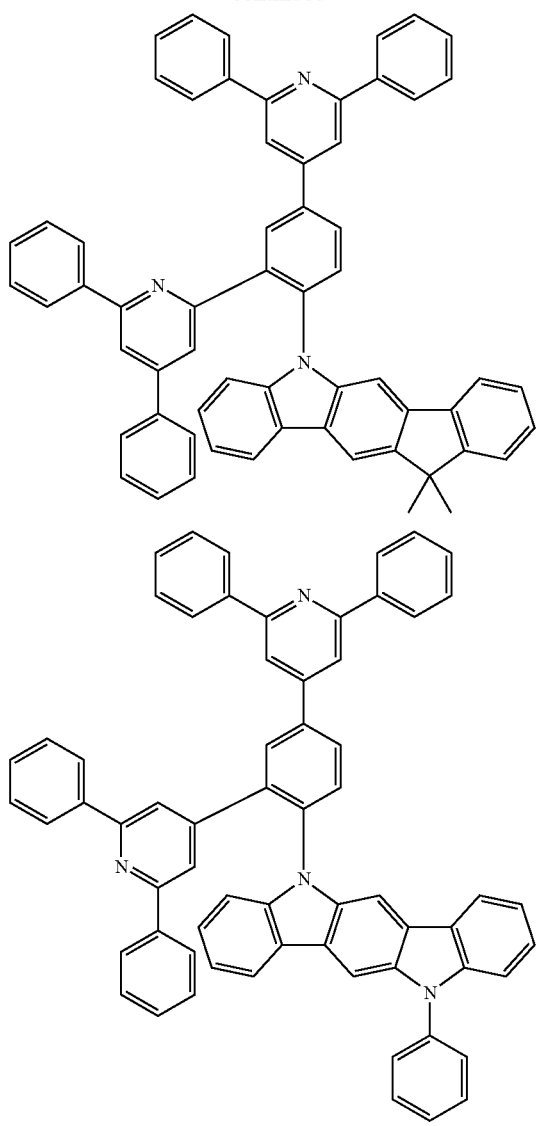
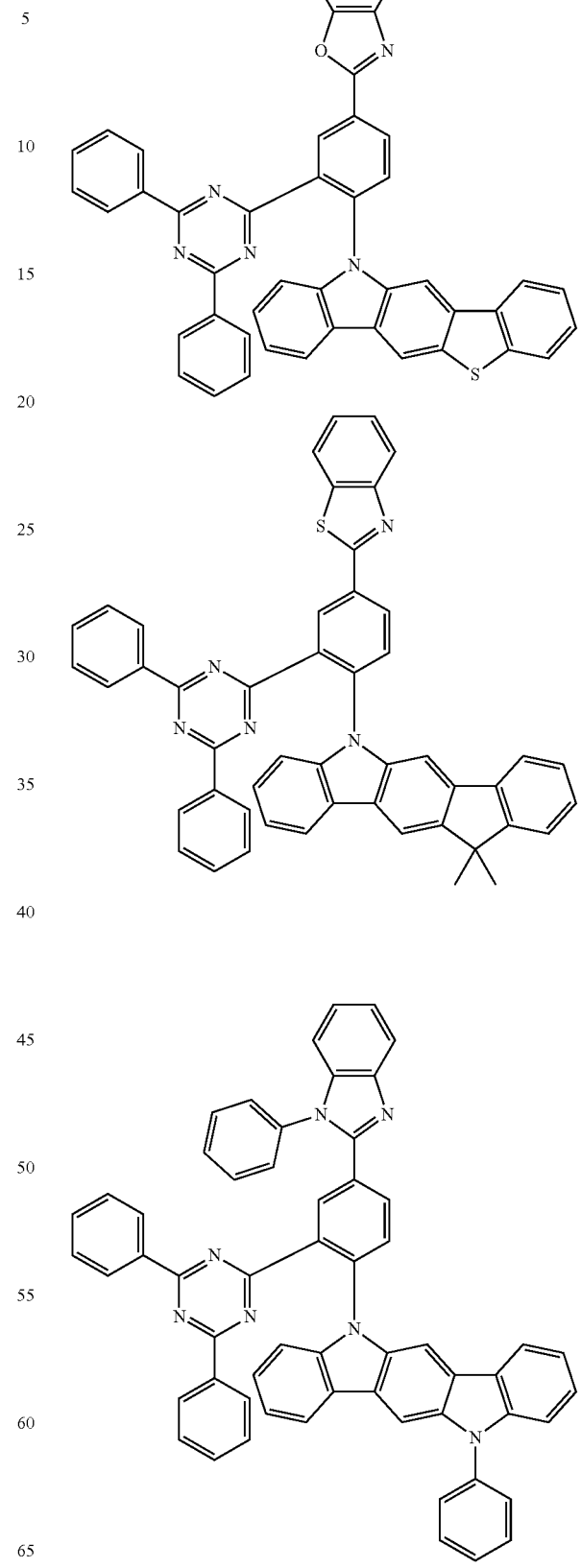

43
-continued
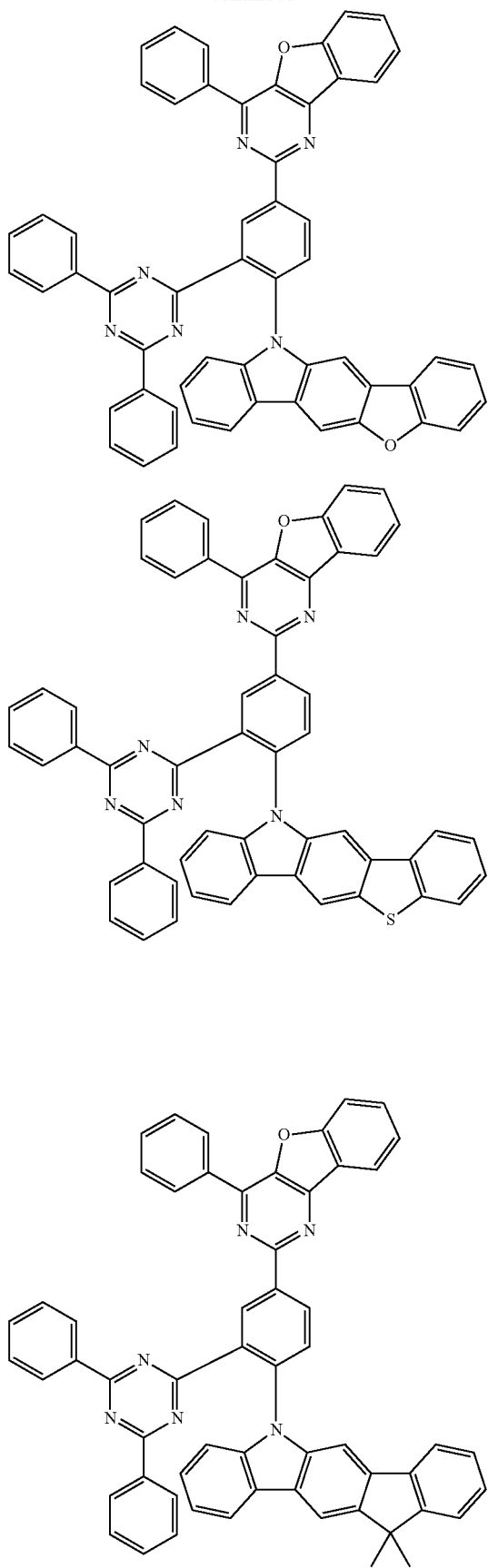
44
-continued
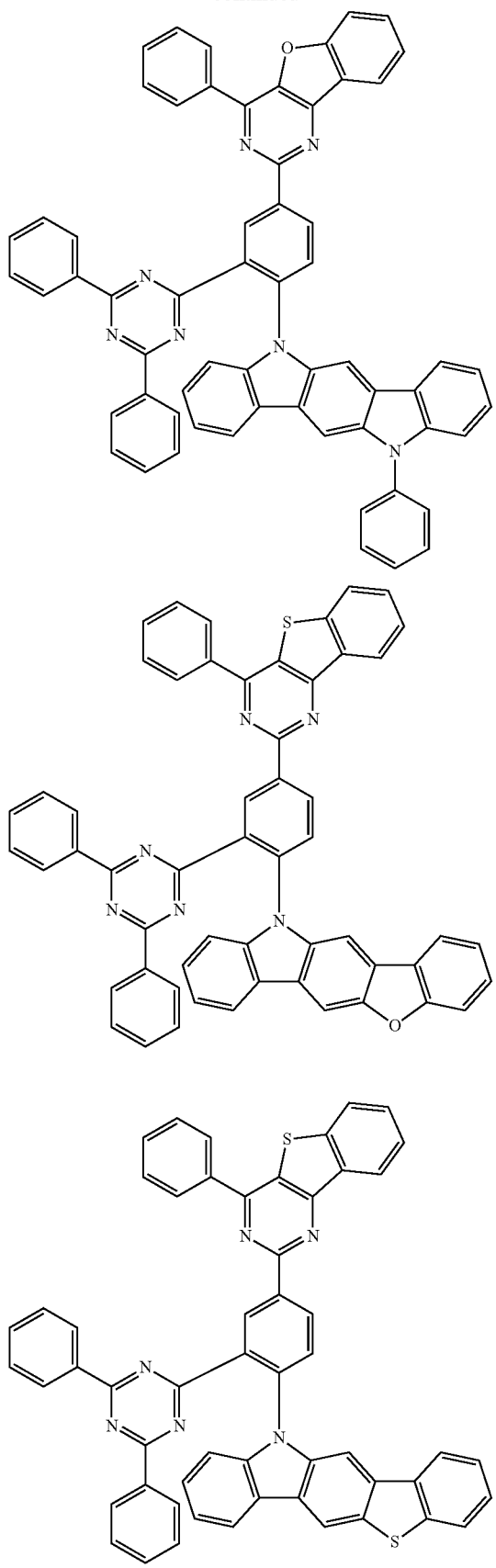

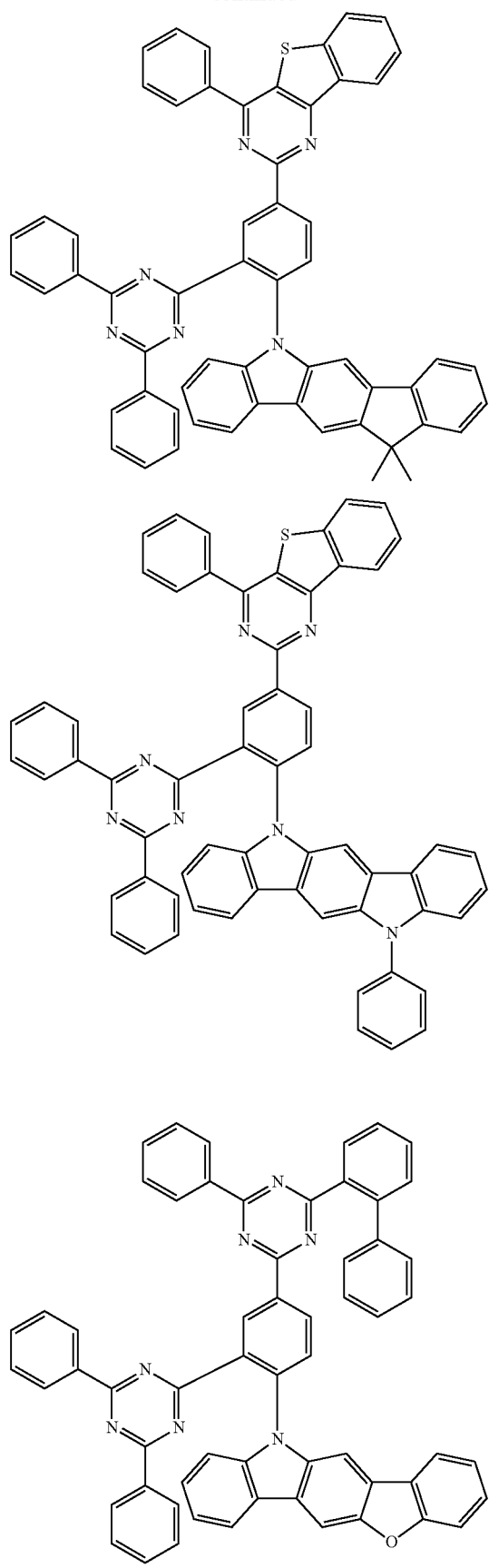

47
-continued
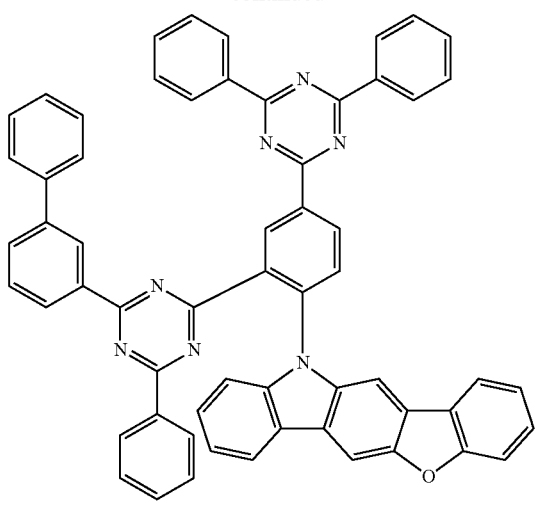
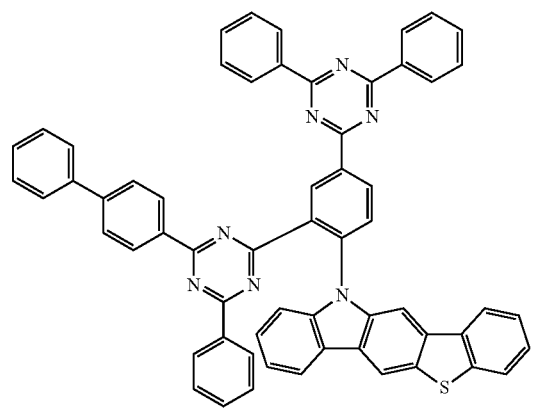
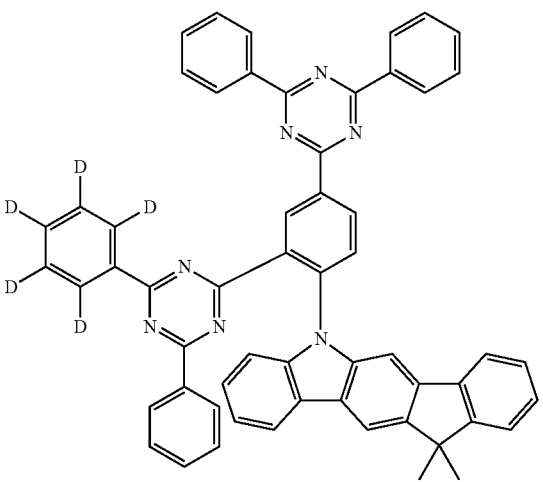
48
-continued
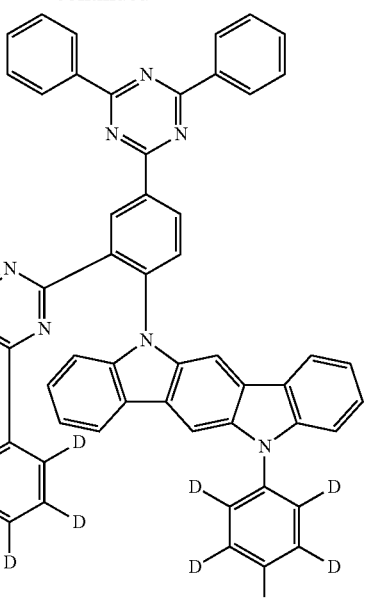
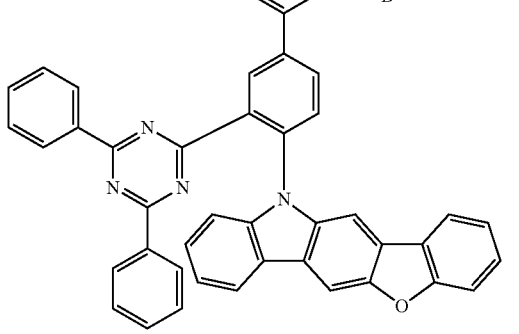
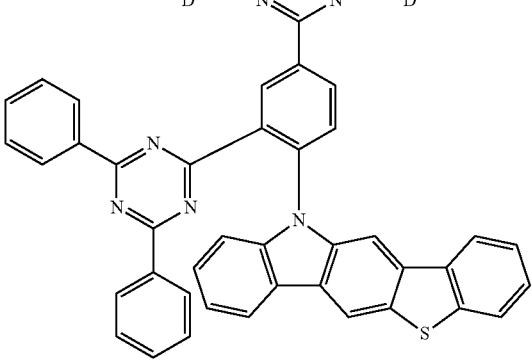

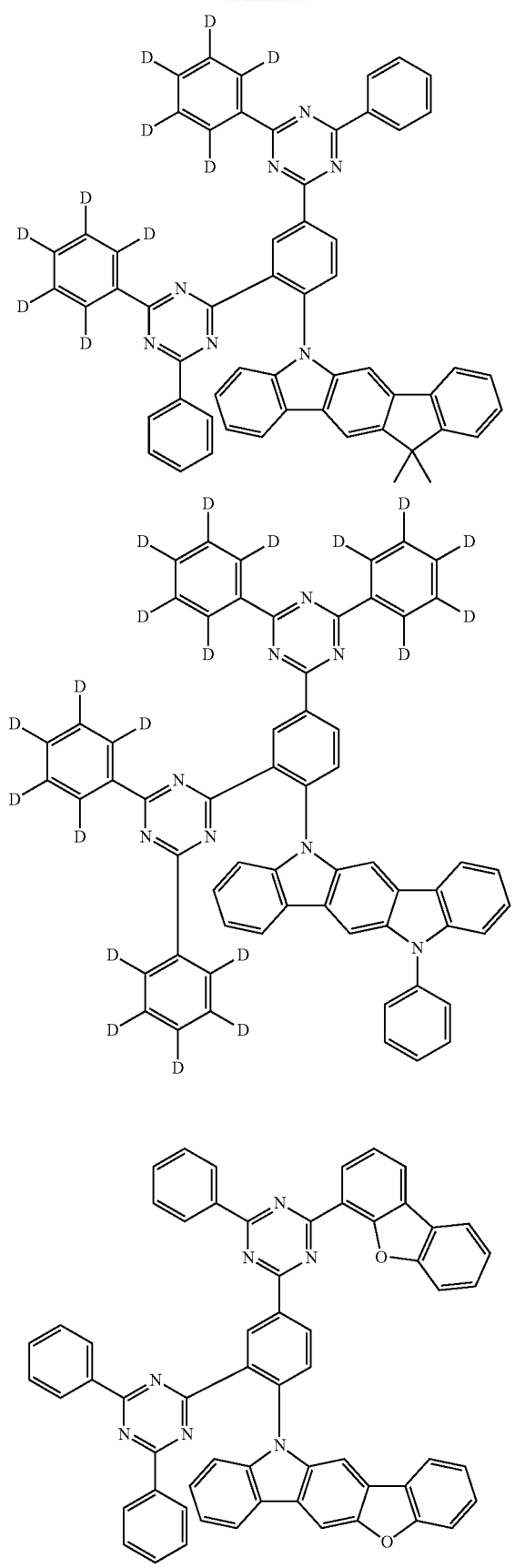
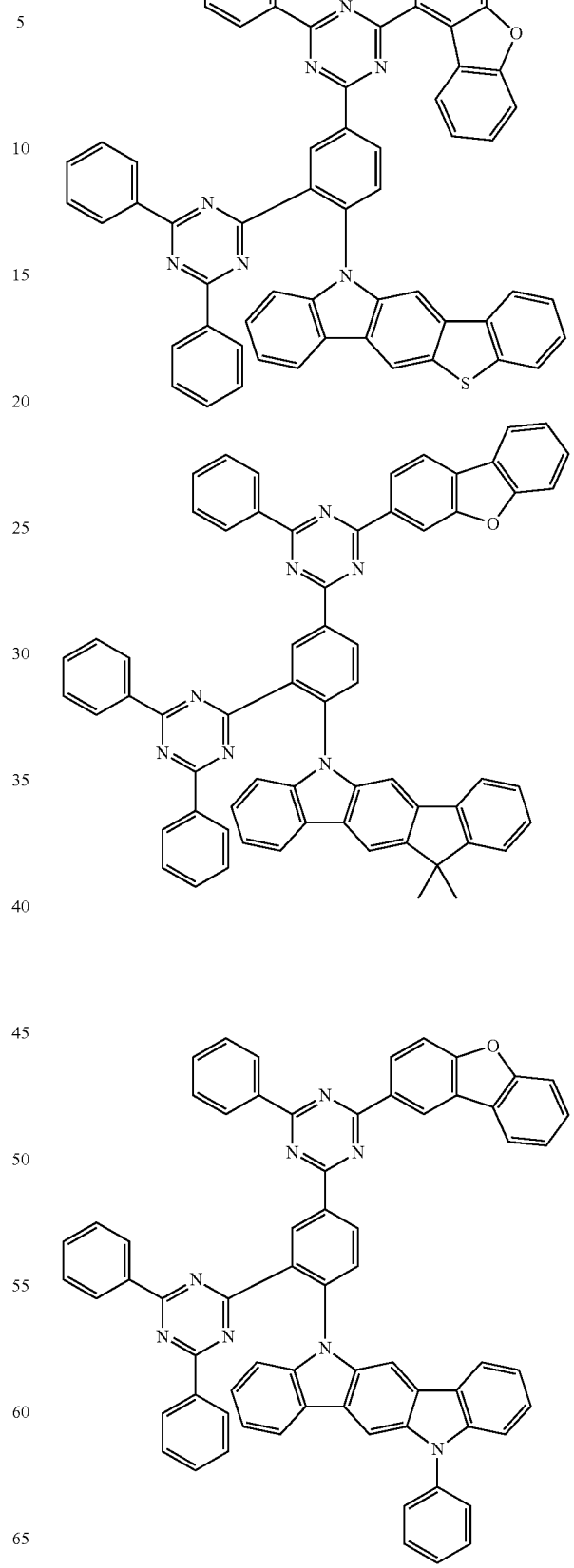

-continued
51
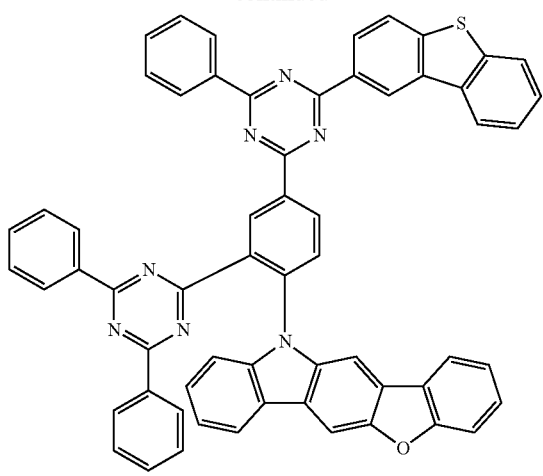
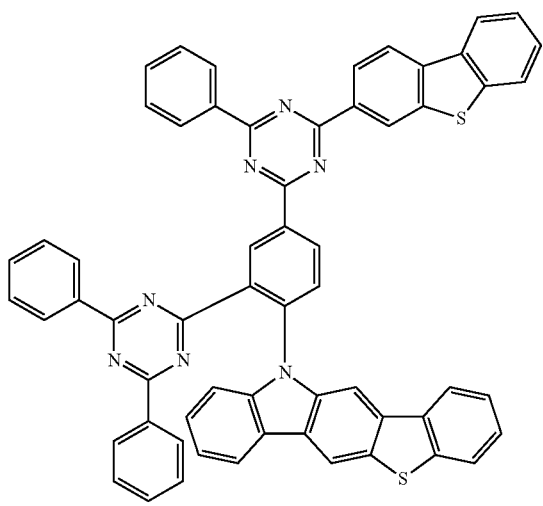
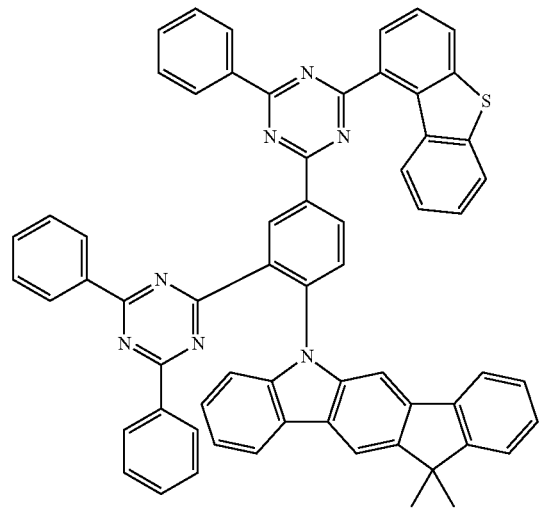
52
-continued
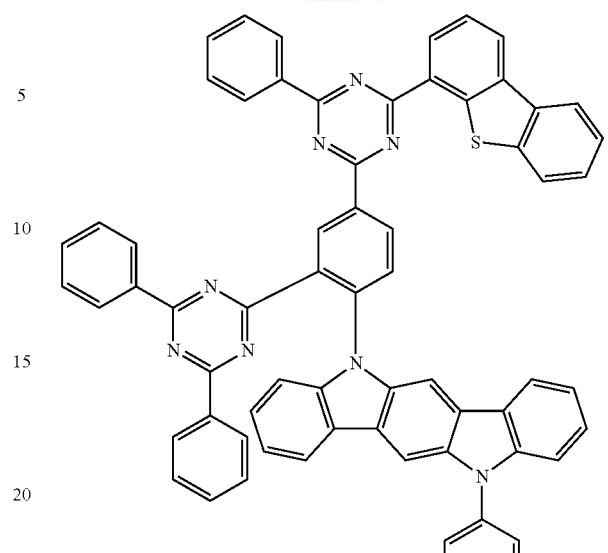
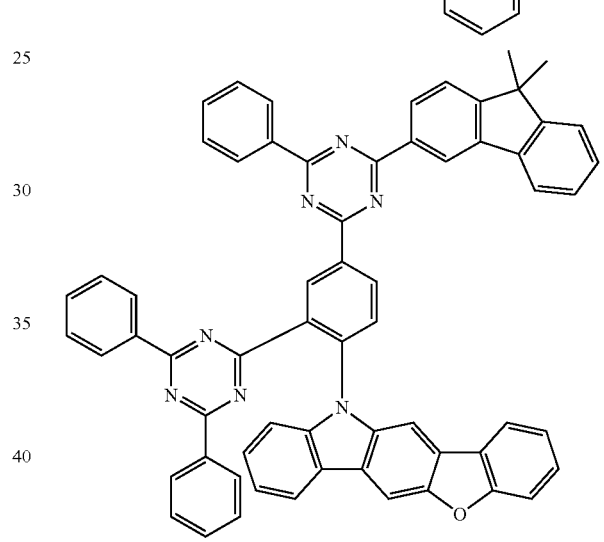
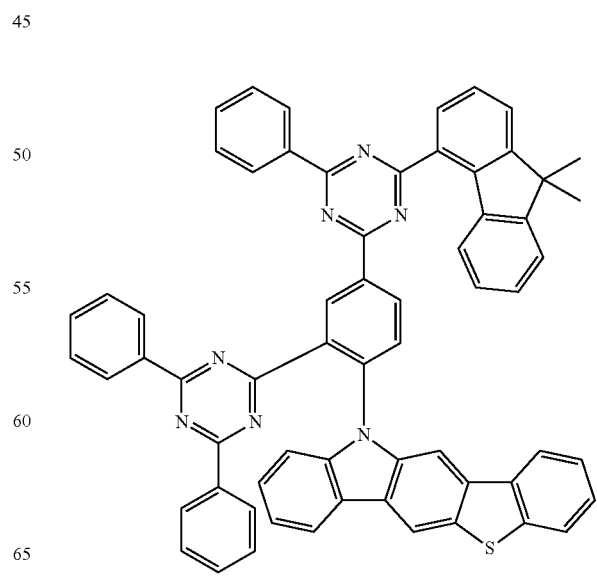

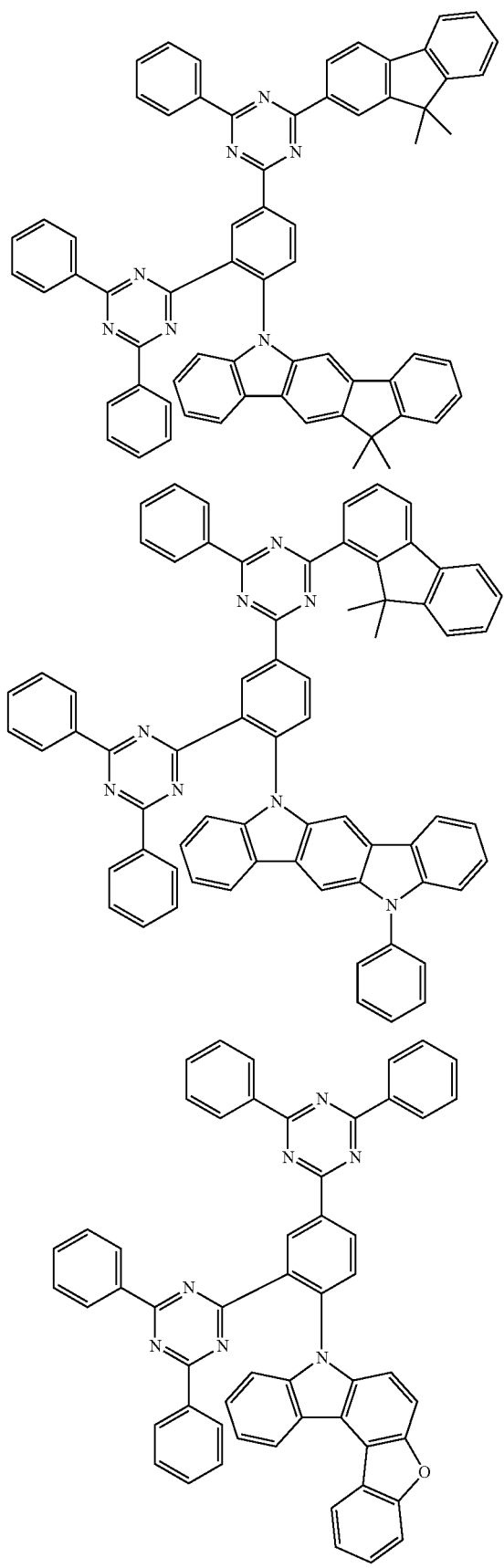

55
-continued
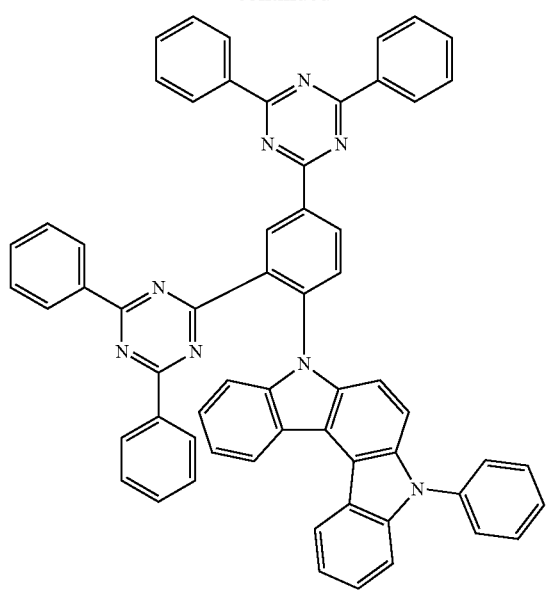
56
-continued
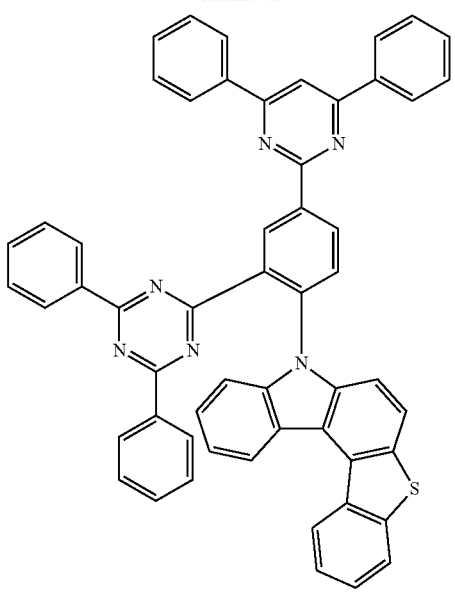
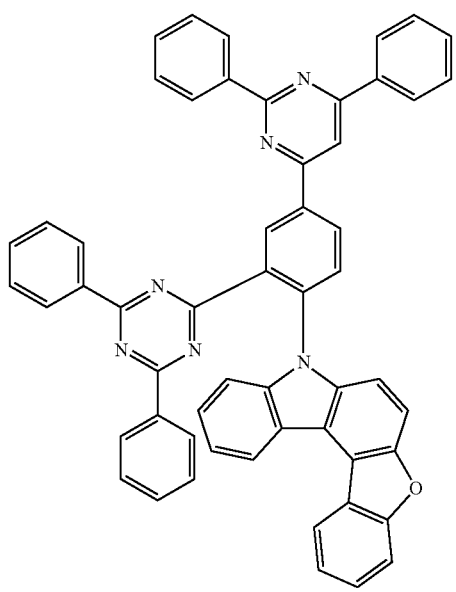
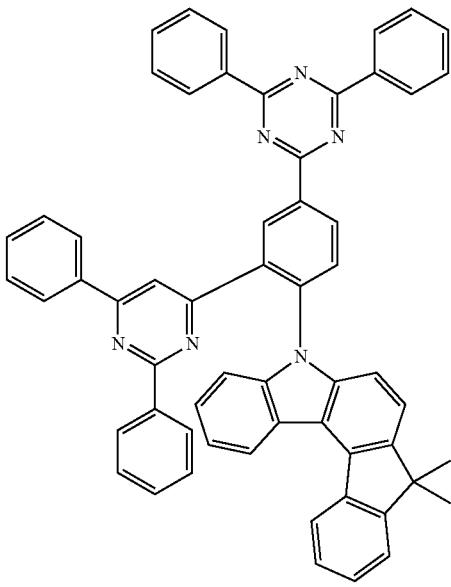

57
-continued
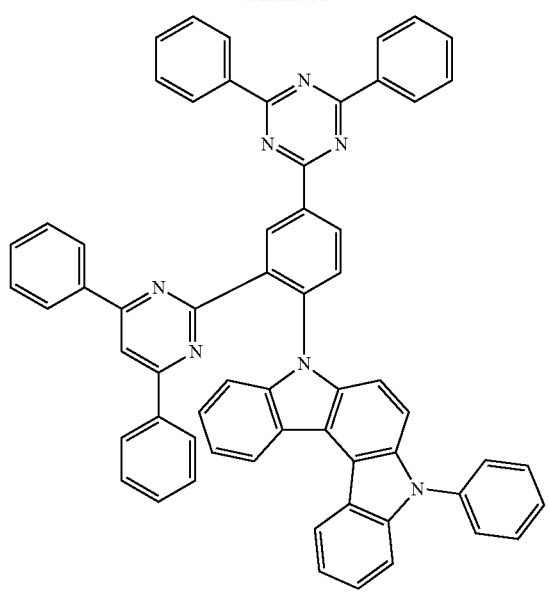
58
-continued
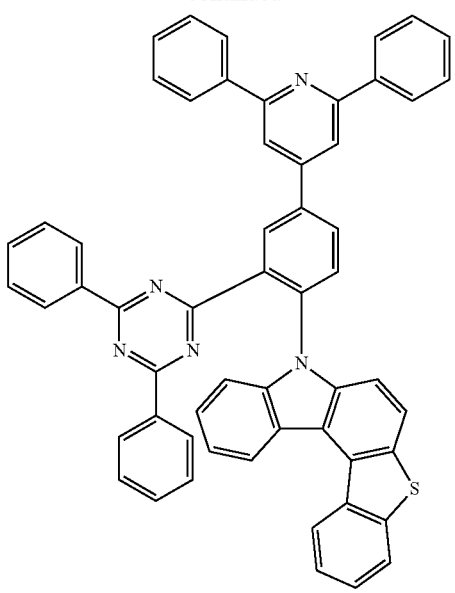
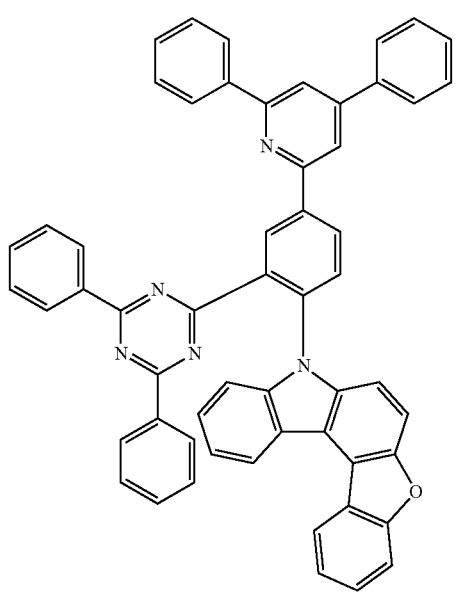
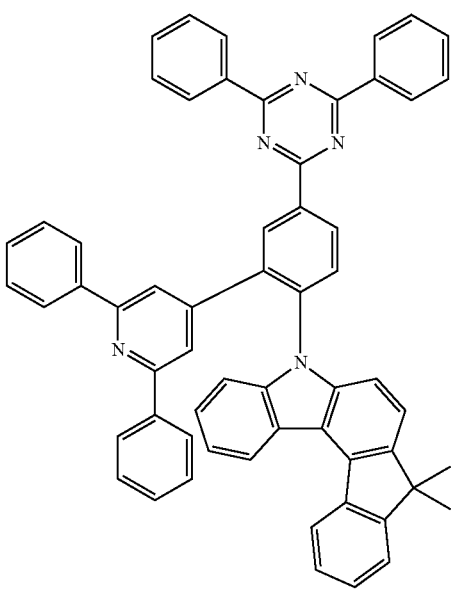

59
-continued
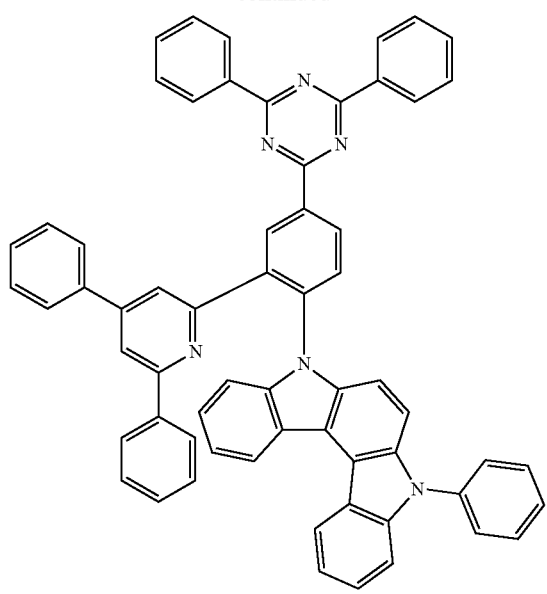
60
-continued
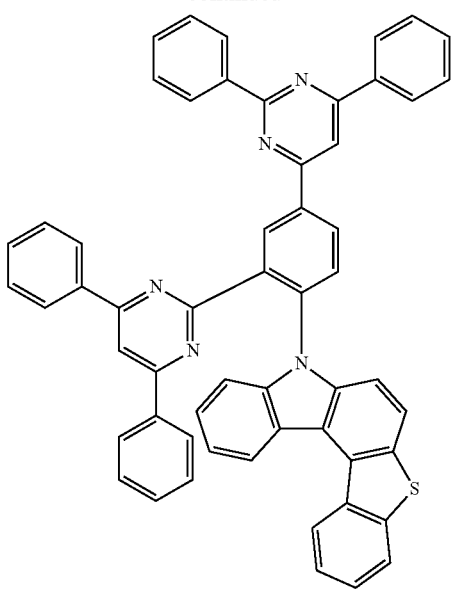
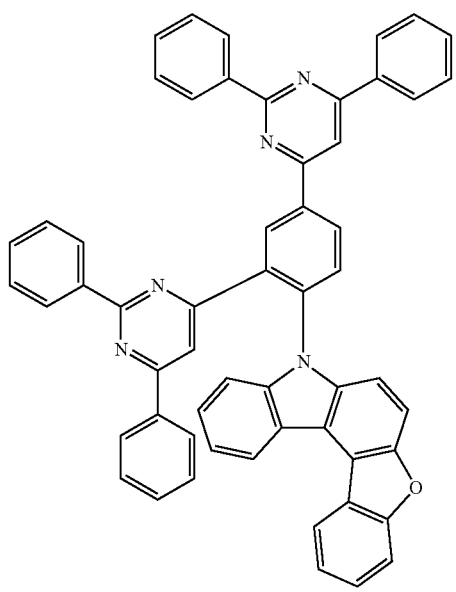
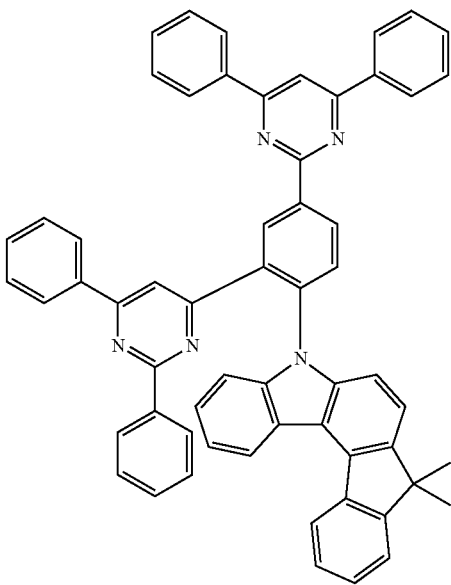

61
-continued
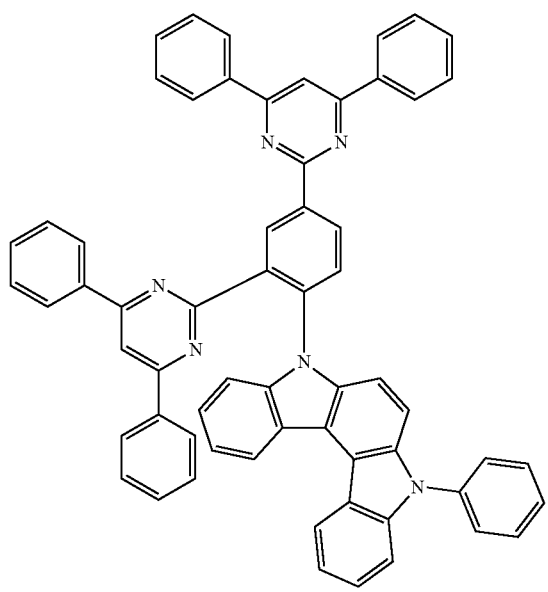
62
-continued
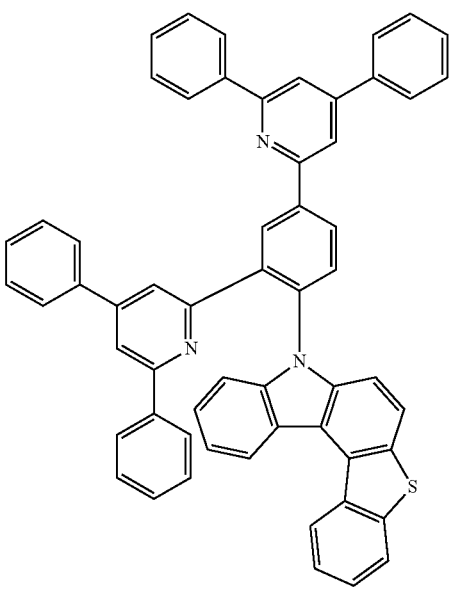
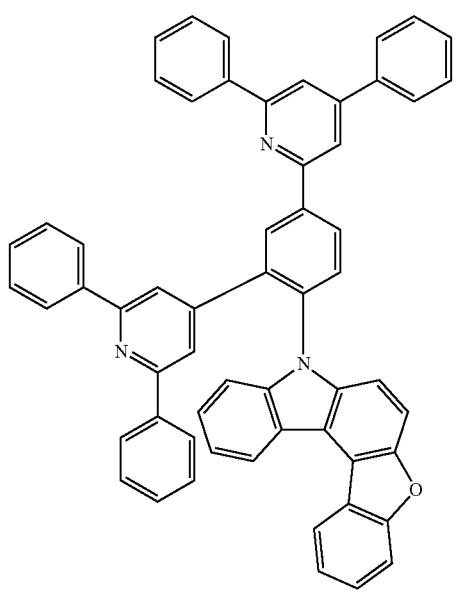
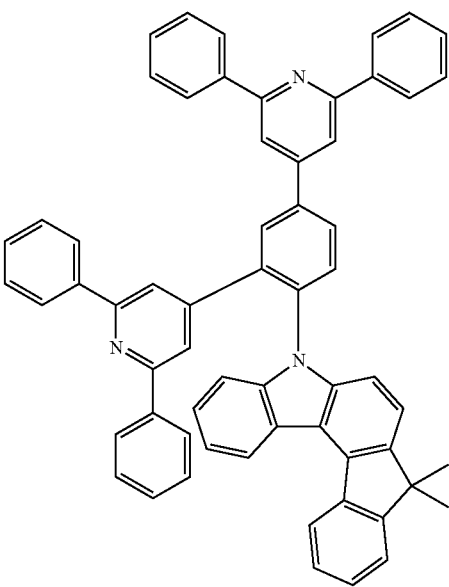

63
-continued
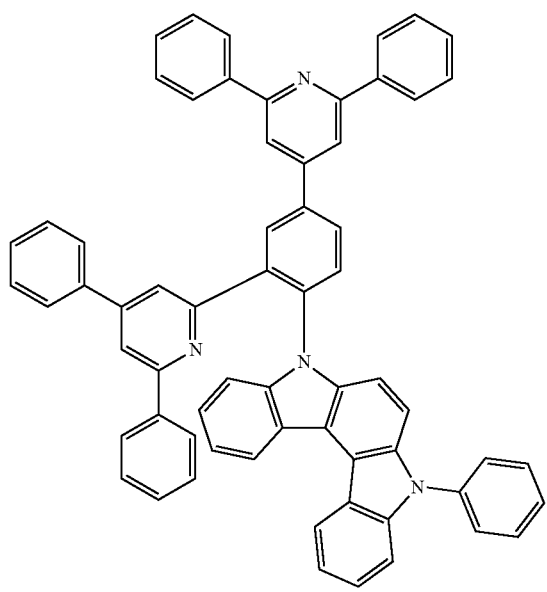
64
-continued
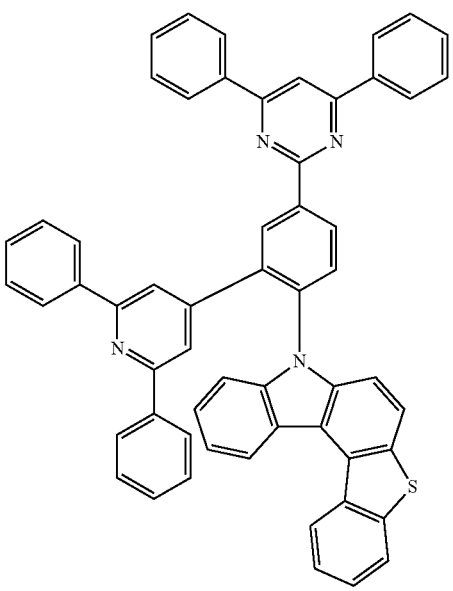
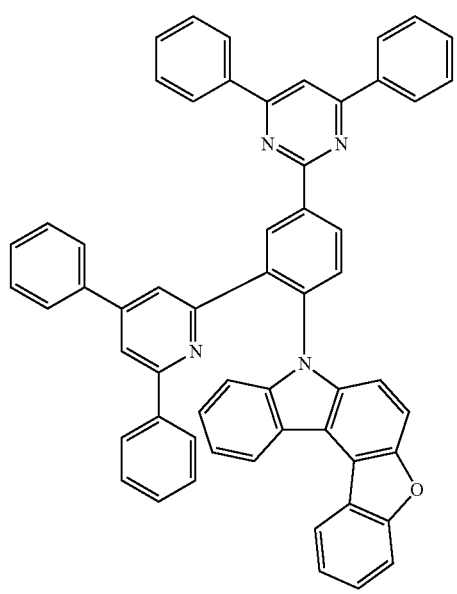
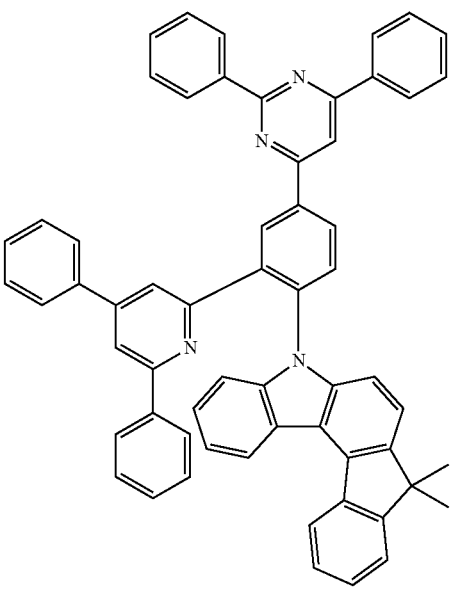

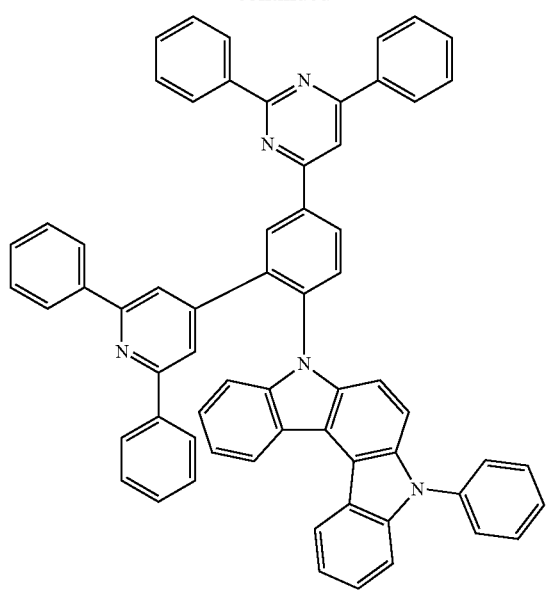
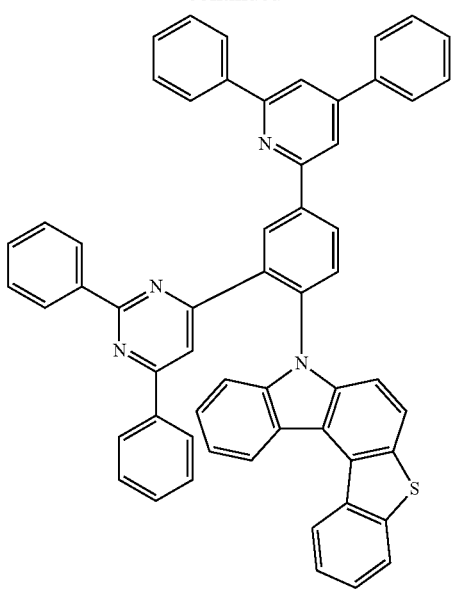
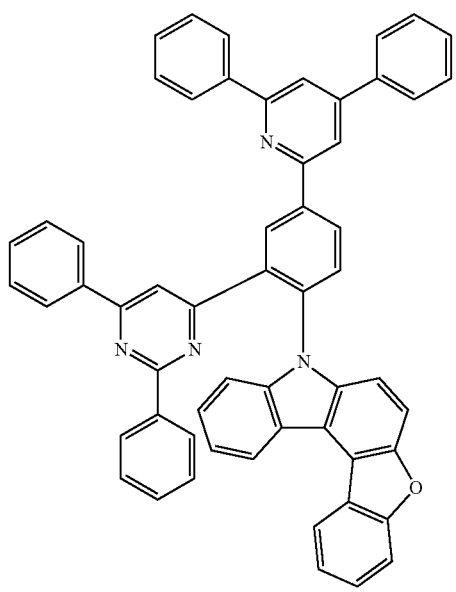
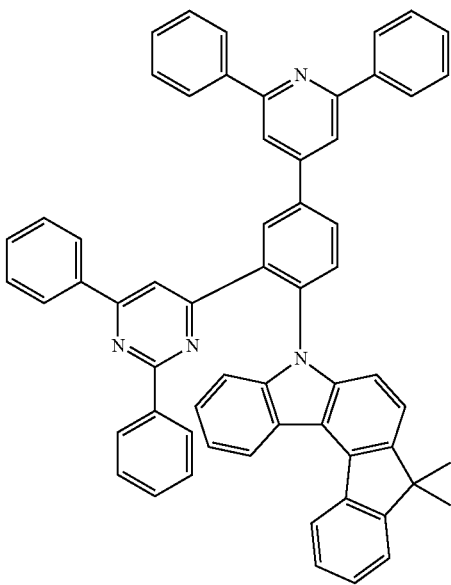

67
-continued
68
-continued
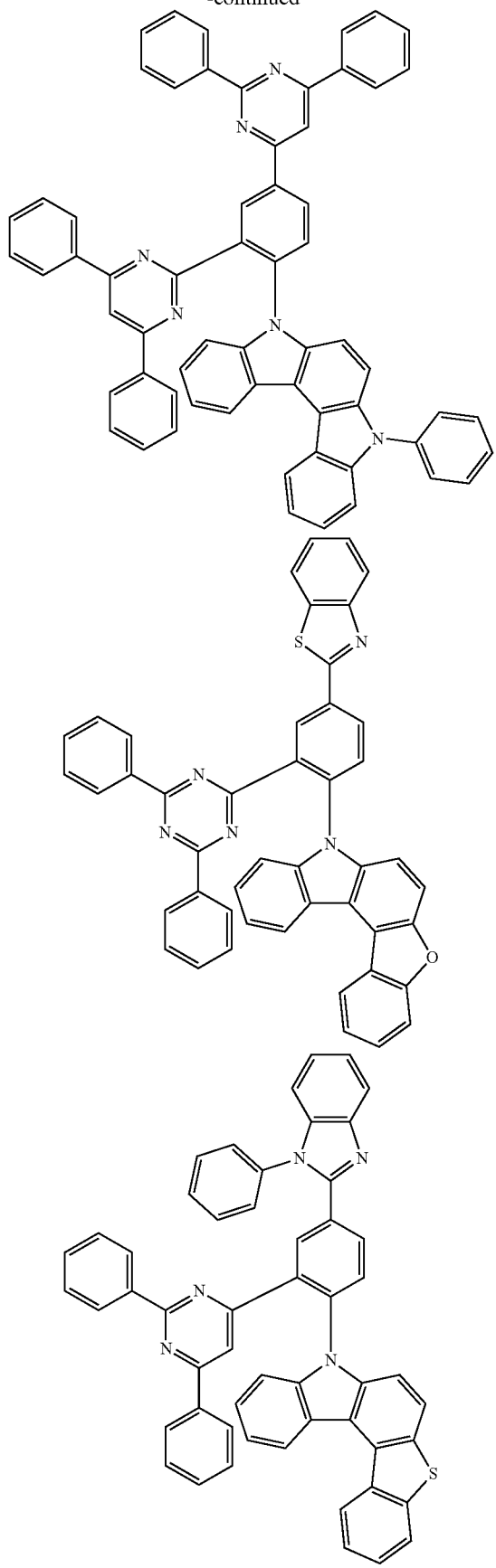

69
-continued
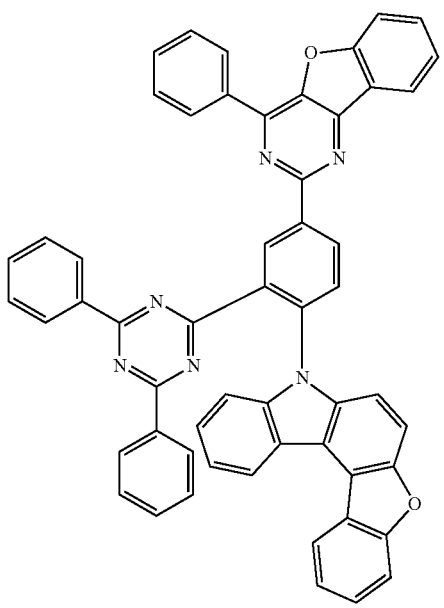
70
-continued
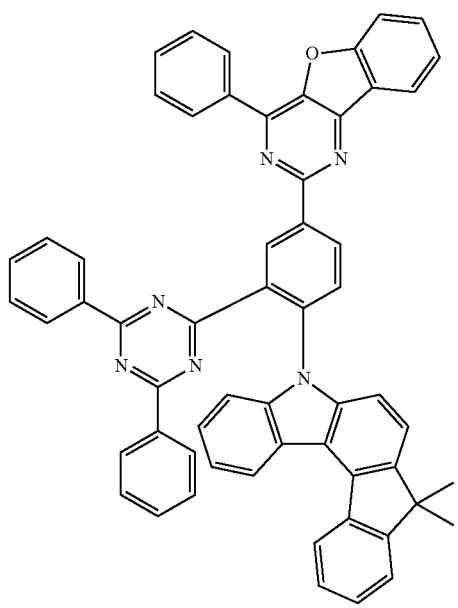
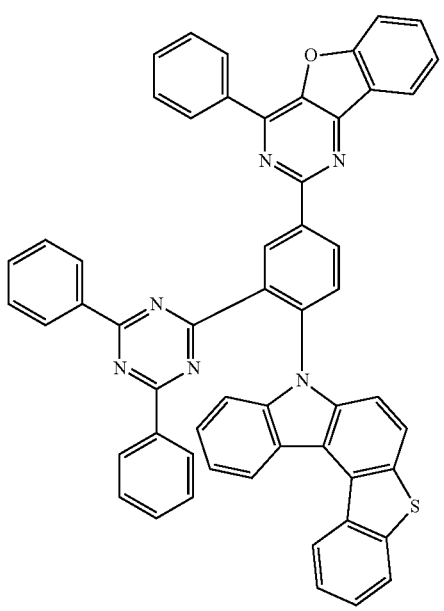
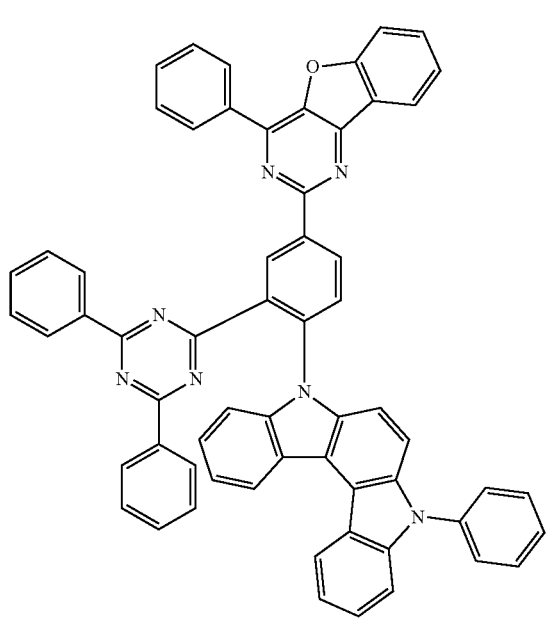

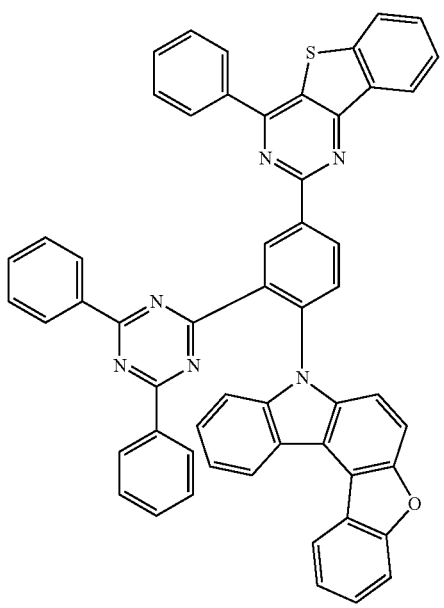
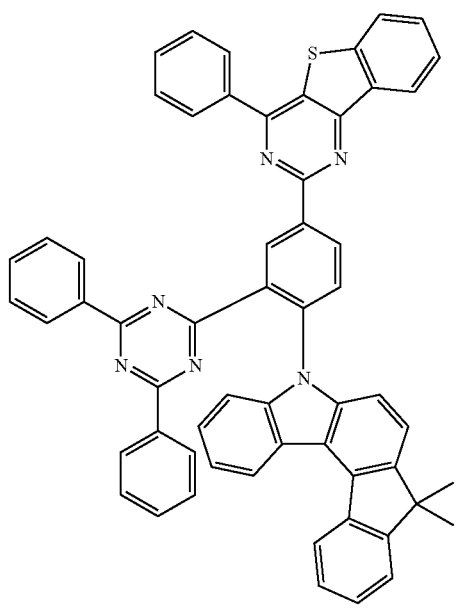
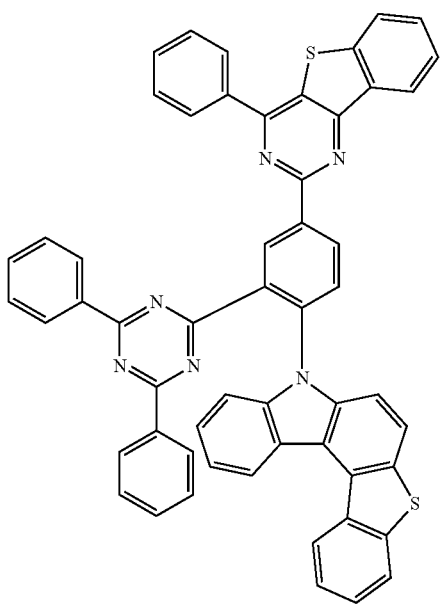
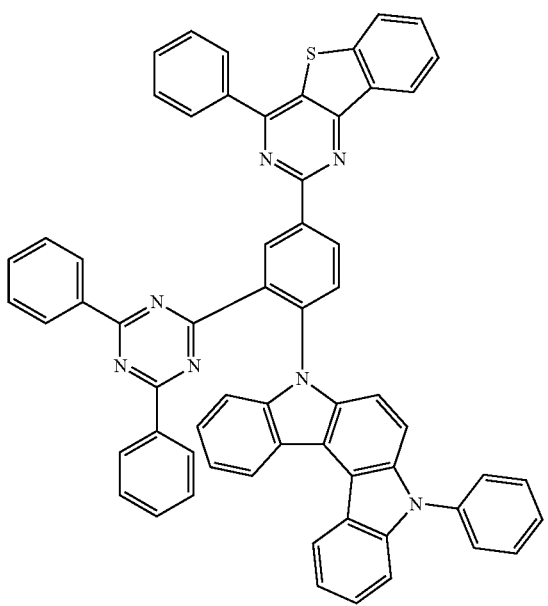

73
-continued
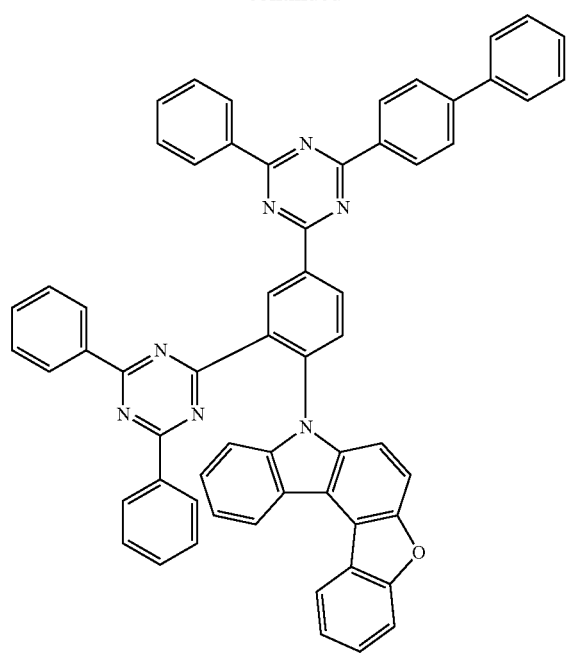
74
-continued
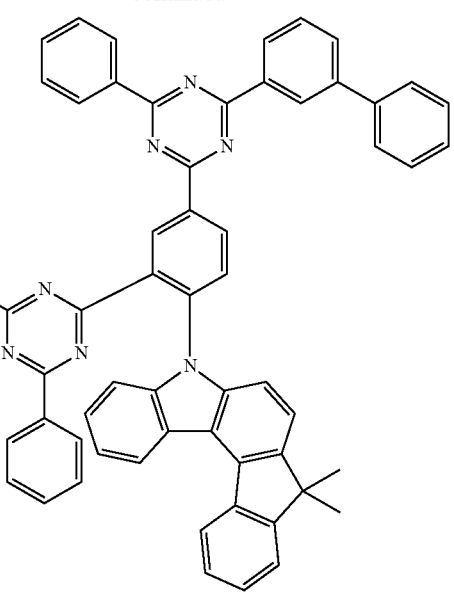
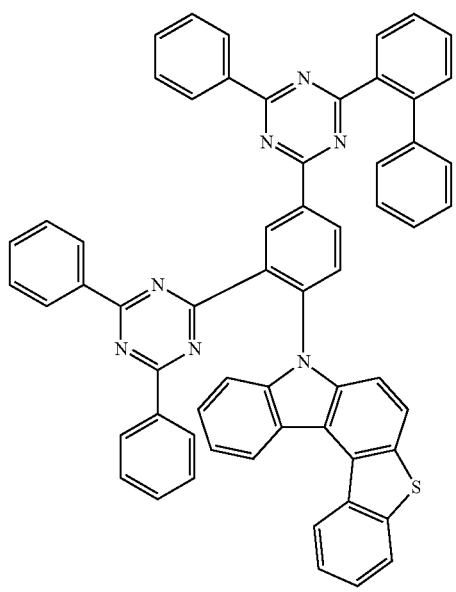
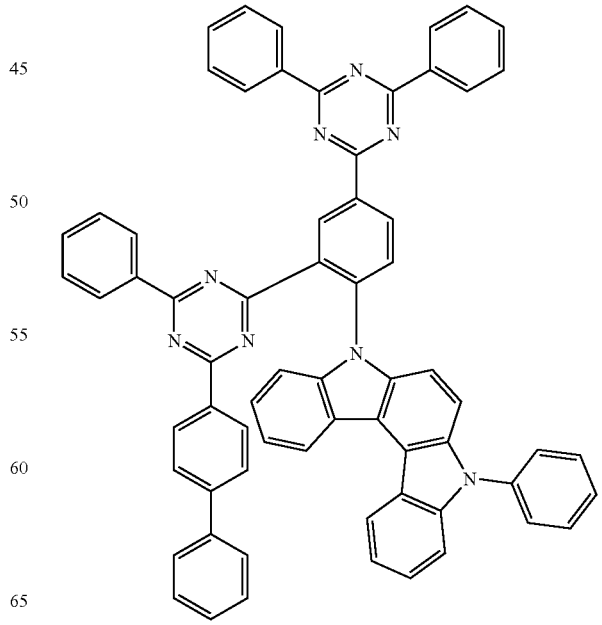

75
-continued
76
-continued
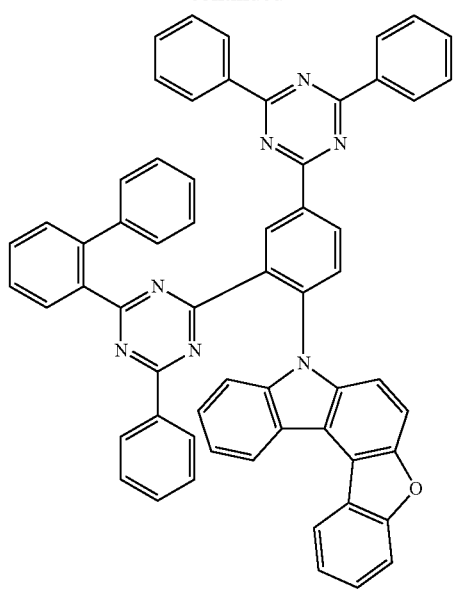
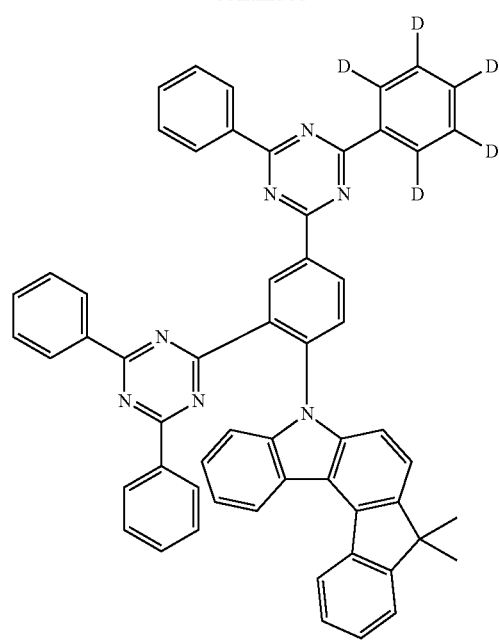

77
-continued
78
-continued
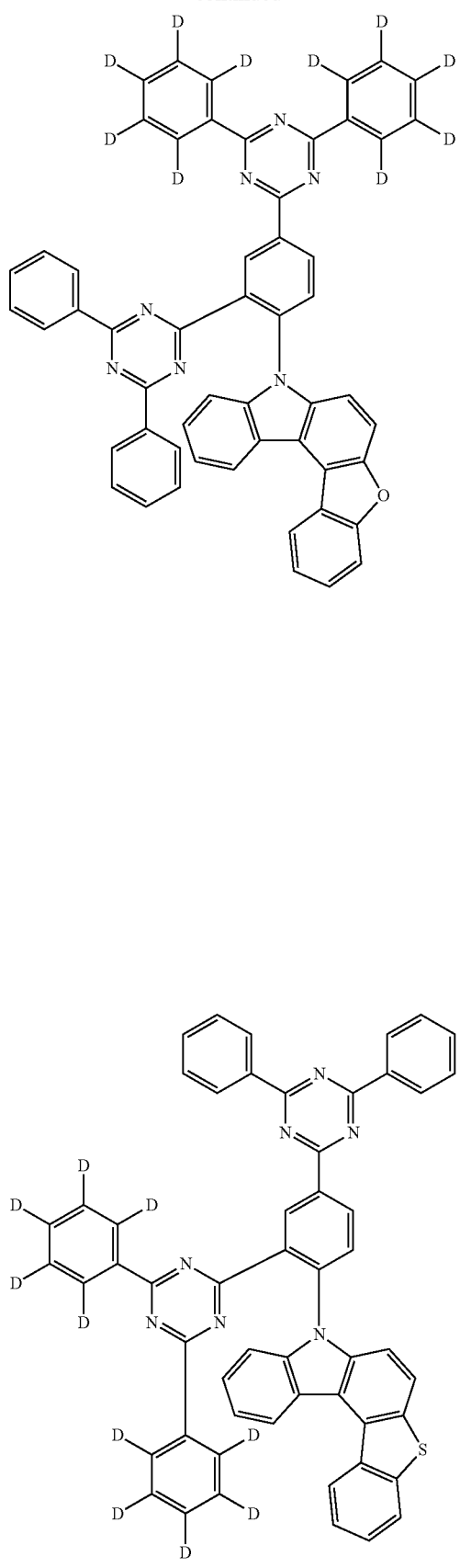
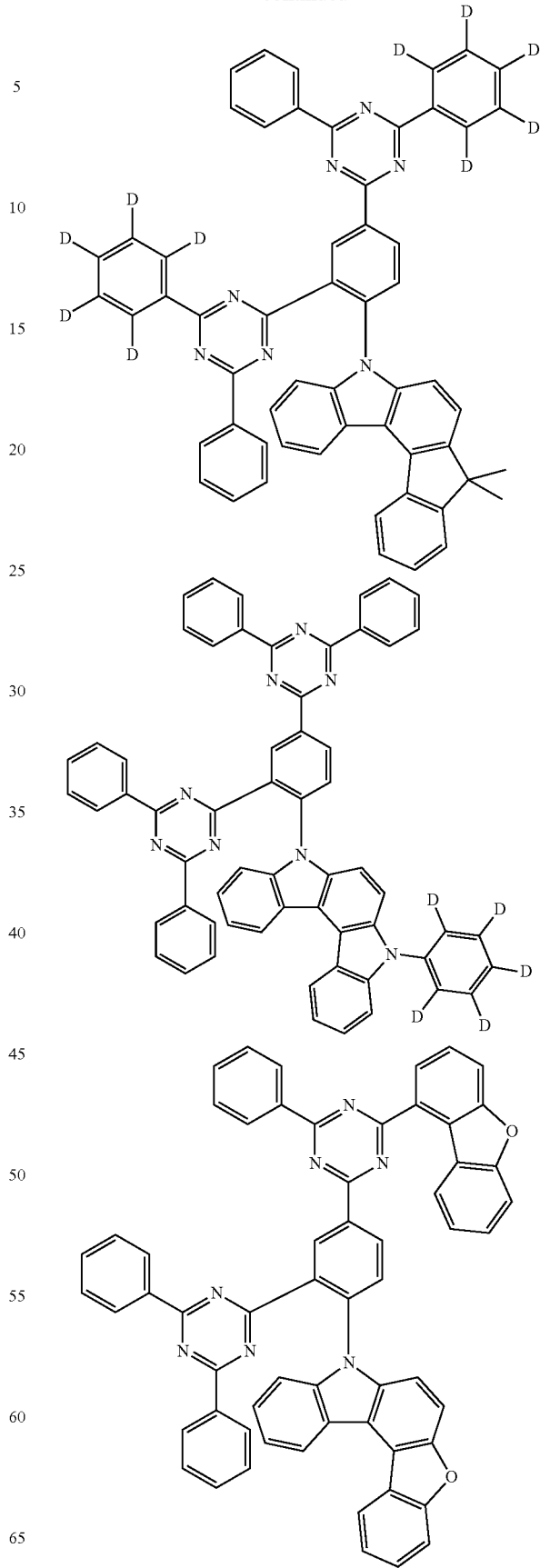

79
-continued
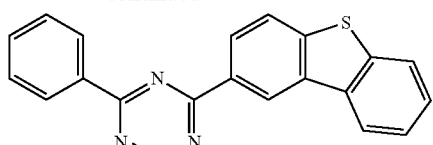
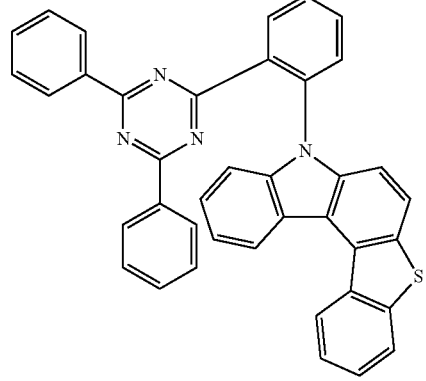
80
-continued
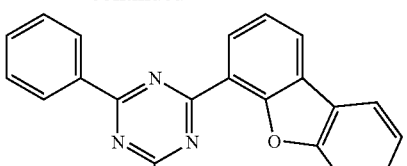
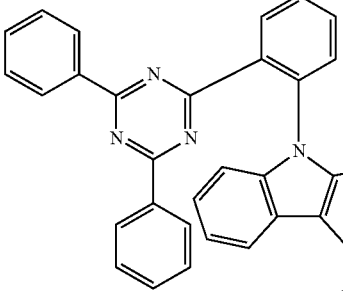
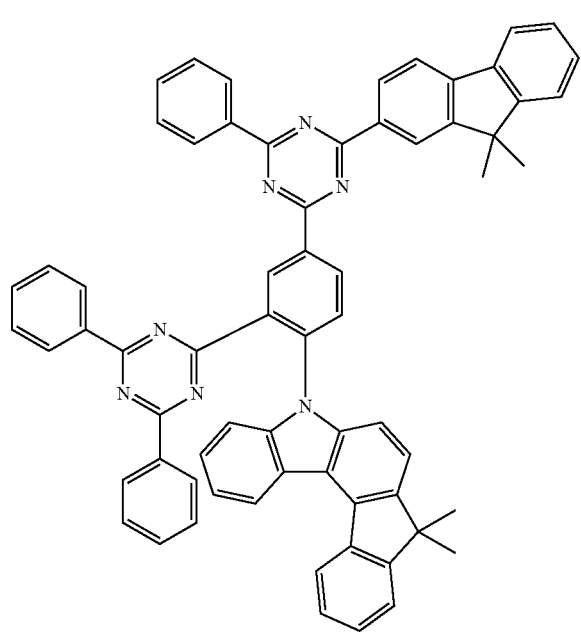
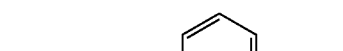

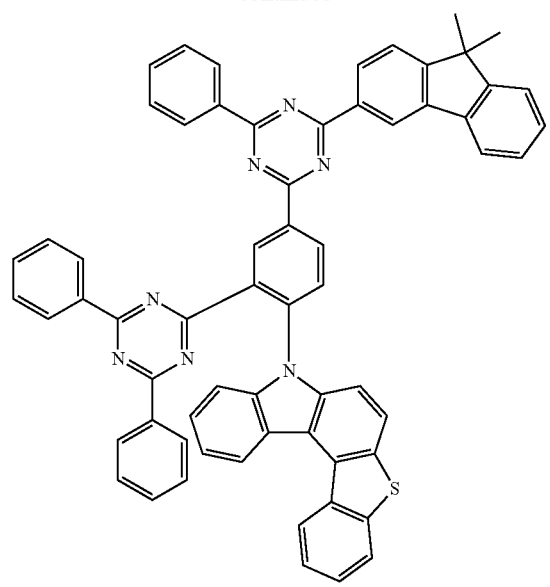
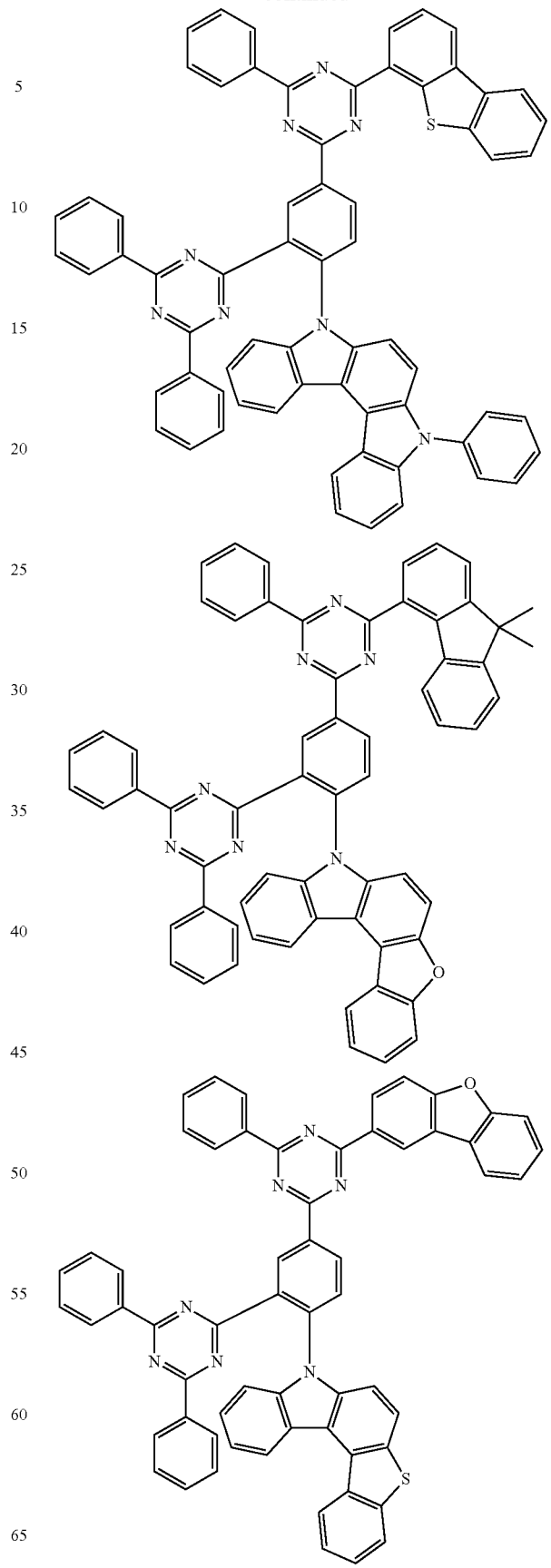

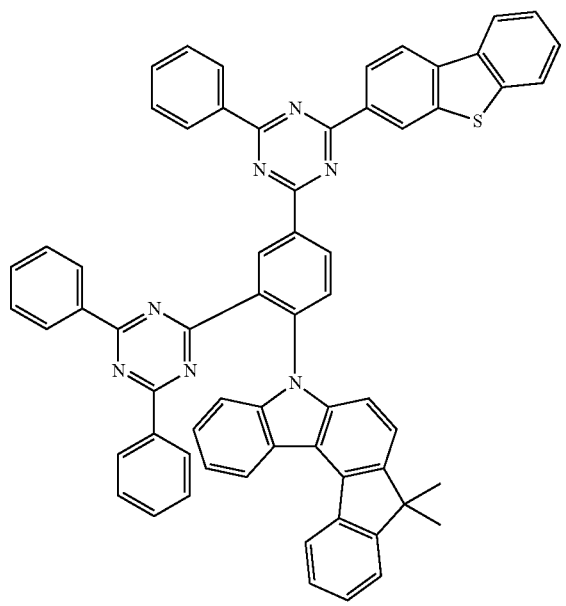
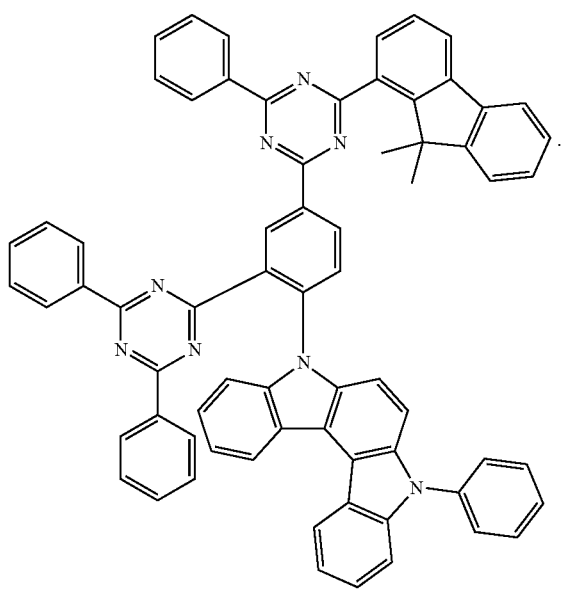
Meanwhile, the compound of Chemical Formula 1 can be prepared by the preparation method shown in the following Reaction Schemes 1 to 3.
Reaction Scheme 1
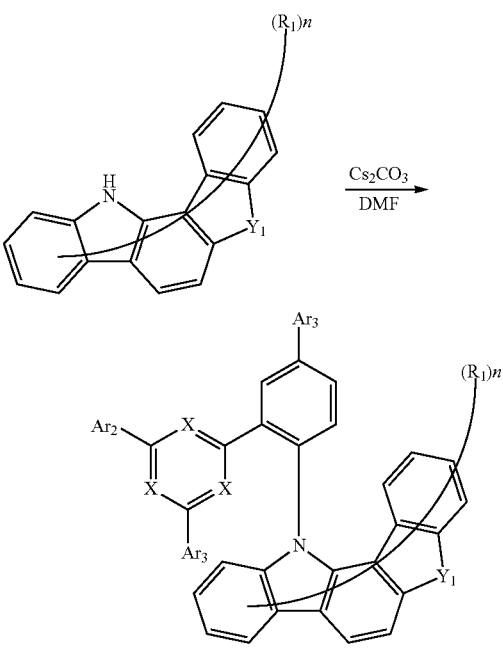
Reaction Scheme 2
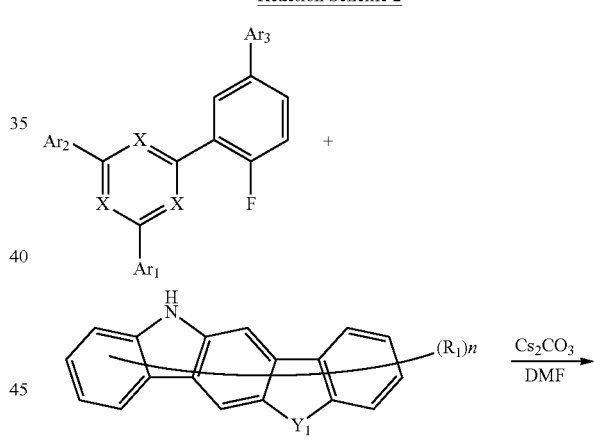
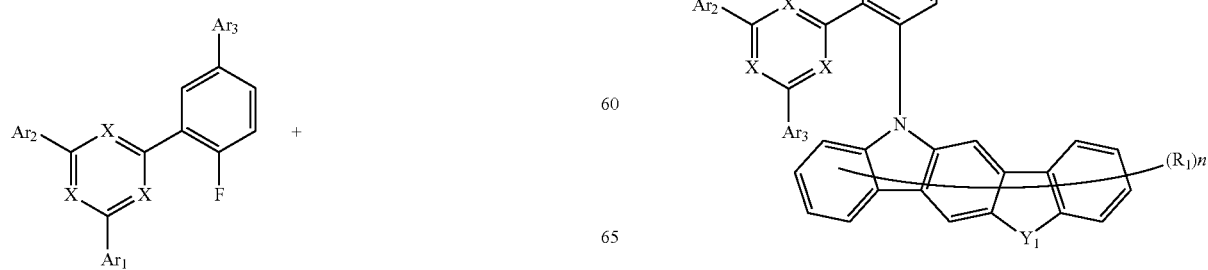

Reaction Scheme 3

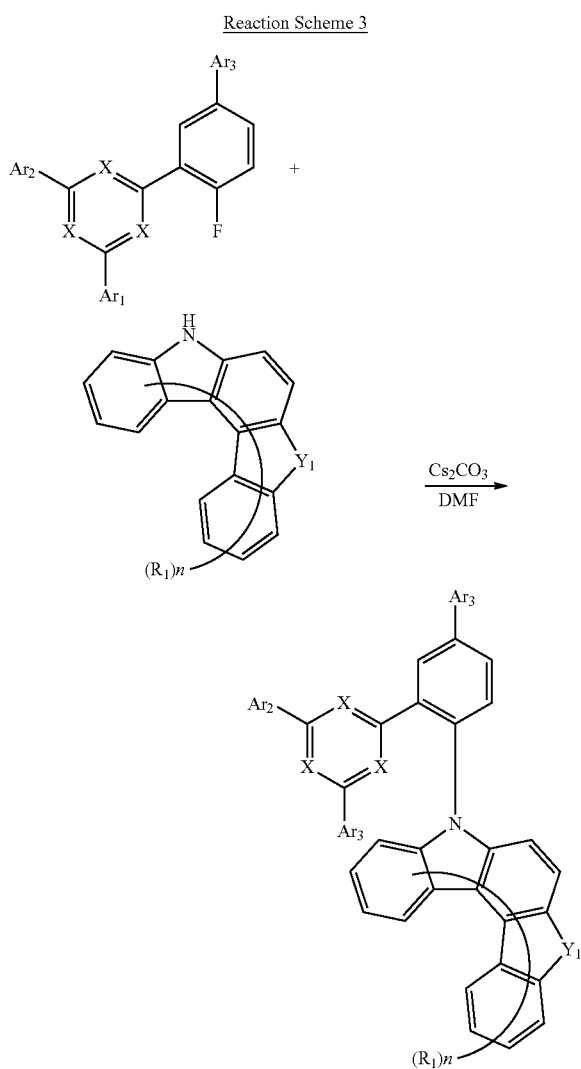

In Reaction Schemes 1 to 3, the definitions of the substituents are the same as defined above, and the above preparation methods can be further embodied in Synthesis Examples described hereinafter.

Another embodiment of the invention provides an organic light emitting device including a compound of Chemical Formula 1 described above. As an example, there is provided an organic light emitting device including a first electrode; a second electrode that is provided opposite to the first electrode; and one or more organic material layers that are provided between the first electrode and the second electrode, wherein one or more layers of the organic material layers include the compound of Chemical Formula 1.

The organic material layer of the organic light emitting device of the present disclosure can have a single-layer structure, or it can have a multilayered structure in which two or more organic material layers are stacked. For example, the organic light emitting device of the present disclosure can have a structure comprising a hole injection layer, a hole transport layer, a light emitting layer, an electron transport layer, an electron injection layer and the like as the organic material layer. However, the structure of the organic light emitting device is not limited thereto, and it can include a smaller number of organic layers.

Further, the organic material layer can include a hole injection layer, a hole transport layer, a layer for simultaneously performing hole injection and transport, or an electron blocking layer, wherein the hole injection layer, the hole transport layer, the layer for simultaneously performing hole injection and transport, and the electron blocking layer can include the compound of Chemical Formula 1.

Further, the organic material layer can include a light emitting layer, wherein the light emitting layer can include the compound of Chemical Formula 1. In this case, the compound of Chemical Formula 1 can be used as a host material in the light emitting layer, and more specifically, the compound of Chemical Formula 1 can be used as a host used in the light emitting layer of a green organic light emitting device.

Further, the organic material layer can include a hole blocking layer, an electron transport layer, an electron injection layer, or a layer for simultaneously performing electron transport and electron injection, wherein the hole blocking layer, the electron transport layer, the electron injection layer, or the layer for simultaneously performing electron transport and electron injection can include the compound of Chemical Formula 1.

Figure 3:
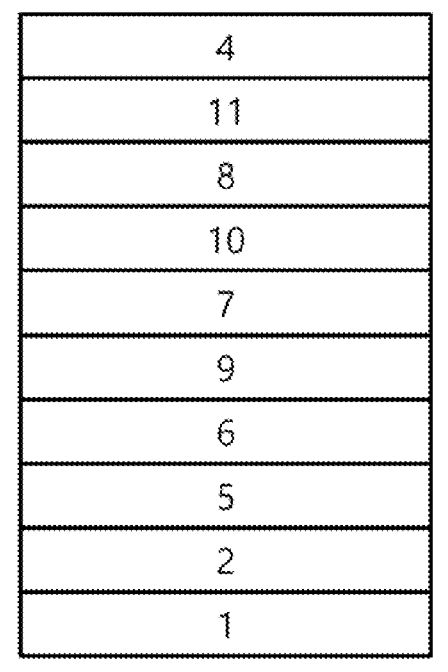

Further, the organic light emitting device according to the present disclosure can be a normal type organic light emitting device in which an anode, one or more organic material layers, and a cathode are sequentially stacked on a substrate. Further, the organic light emitting device according to the present disclosure can be an inverted type organic light emitting device in which a cathode, one or more organic material layers, and an anode are sequentially stacked on a substrate. For example, the structure of the organic light emitting device according to an embodiment of the present disclosure is illustrated in FIGS. 1 to 3.

FIG. 1 shows an example of an organic light emitting device comprising a substrate 1, an anode 2, a light emitting layer 3, and a cathode 4. In such a structure, the compound of Chemical Formula 1 can be included in the light emitting layer.

FIG. 2 shows an example of an organic light emitting device comprising a substrate 1, an anode 2, a hole injection layer 5, a hole transport layer 6, a light emitting layer 7, an electron transport layer 8, and a cathode 4. In such a structure, the compound of Chemical Formula 1 can be included in one or more layers of the hole injection layer, the hole transport layer, the light emitting layer, and the electron transport layer.

FIG. 3 shows an example of an organic light emitting device comprising a substrate 1, an anode 2, a hole injection layer 5, a hole transport layer 6, an electron blocking layer 9, a light emitting layer 7, a hole blocking layer 10, an electron transport layer 8, an electron injection layer 11, and a cathode 4. In such a structure, the compound of Chemical Formula 1 can be included in one or more layers of the hole injection layer, the hole transport layer, the electron blocking layer, the light emitting layer, the hole blocking layer, the electron transport layer, and the electron injection layer.

The organic light emitting device according to the present disclosure can be manufactured by materials and methods known in the art, except that one or more layers of the organic material layers include the compound of Chemical Formula 1. In addition, when the organic light emitting device includes a plurality of organic material layers, the organic material can be formed of the same material or different material.

For example, the organic light emitting device according to the present disclosure can be manufactured by sequentially stacking a first electrode, an organic material layer and a second electrode on a substrate. In this case, the organic light emitting device can be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer and the electron transport layer thereon, and then depositing a material that can be used as the cathode thereon. In addition to such a method, the organic light emitting device can be manufactured by sequentially depositing a cathode material, an organic material layer and an anode material on a substrate.

In addition, the compound of Chemical Formula 1 can be formed into an organic material layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic light emitting device can be manufactured by sequentially depositing a cathode material, an organic material layer and an anode material on a substrate (International Publication WO2003/012890). However, the manufacturing method is not limited thereto.

As an example, the first electrode is an anode, and the second electrode is a cathode, or alternatively the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb, conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection material is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to a hole injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrin, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer, and it is suitably a material having large mobility to the holes, which can receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The electron blocking layer is formed on the hole transport layer, preferably provided in contact with the light emitting layer, and severs to adjust the hole mobility, prevent excessive movement of electrons and increase the probability of hole-electron coupling, thereby improving the efficiency of the organic light emitting device. The electron blocking layer includes an electron blocking material, and as such electron blocking material, a material having a stable structure in which electrons may not flow out of the light emitting layer is suitable. Specific examples thereof can include an arylamine-based organic material or the like, but are not limited thereto.

The light emitting material is preferably a material which can receive holes and electrons transported from a hole transport layer and an electron transport layer, respectively, and combine the holes and the electrons to emit light in a visible ray region, and has good quantum efficiency to fluorescence or phosphorescence. Specific examples of the light emitting material include an 8-hydroxy-quinoline aluminum complex ($Alq_3$), a carbazole-based compound, a dimerized styryl compound, BAlq, a 10-hydroxybenzoquinoline-metal compound, a benzoxazole compound, a benzothiazole compound, a benzimidazole-based compound, a poly(p-phenylenevinylene)(PPV)-based polymer, a Spiro compound, polyfluorene, rubrene, and the like, but are not limited thereto.

The light emitting layer can include a host material and a dopant material. The host material can be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

The dopant material includes an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The hole blocking layer is formed on the light emitting layer, and specifically, the hole blocking layer is provided in contact with the light emitting layer, and severs to prevent excessive movement of holes and increase the probability of hole-electron coupling, thereby improving the efficiency of the organic light emitting device. The hole blocking layer includes a hole blocking material, and as such hole blocking material, a material having a stable structure in which holes may not flow out of the light emitting layer is suitable. As the hole blocking material, a compound into which an electron-withdrawing group is introduced, such as azine derivatives including triazine, triazole derivatives, oxadiazole derivatives, phenanthroline derivatives, phosphine oxide derivatives can be used, but is not limited thereto.

The electron transport layer is a layer which receives electrons from an electron injection layer and transports the electrons to a light emitting layer, and an electron transport material is suitably a material which can receive electrons well from a cathode and transfer the electrons to a light emitting layer, and has a large mobility for electrons. Specific examples of the electron transport material include: an Al complex of 8-hydroxyquinoline, a complex including Alq$_3$, an organic radical compound, a hydroxyflavone-metal complex, and the like, but are not limited thereto. The electron transport layer can be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples of the electron injection layer include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

The metal complex compound includes 8-hydroxyquinolinato lithium, bis(8-hydroxyquinolinato)zinc, bis(8-hydroxyquinolinato)copper, bis(8-hydroxy-quinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)-(2-naphtholato)gallium, and the like, but are not limited thereto.

The organic light emitting device according to the present disclosure can be a front side emission type, a back side emission type, or a double side emission type according to the used material.

In addition, the compound of Chemical Formula 1 can be included in an organic solar cell or an organic transistor in addition to an organic light emitting device.

The preparation of the compound of Chemical Formula 1 and the organic light emitting device including the same will be described in detail in the following examples. However, these examples are presented for illustrative purposes only and are not intended to limit the scope of the present disclosure.

Synthesis Example

Synthesis Example 1: Synthesis of Compound

Step 1) Synthesis of Compound 1-a

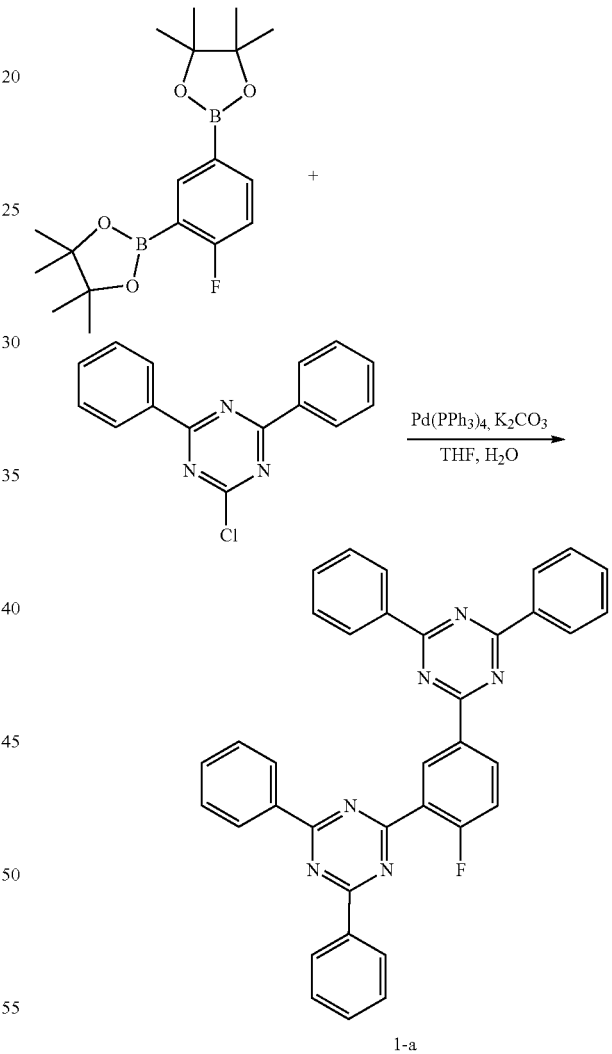

2,2'-(4-Fluoro-1,3-phenylene)bis(4,4,5,5-tetramethyl-1,3,2-dioxaborolane) (15 g, 43.1 mmol) and 2-chloro-4,6-diphenyl-1,3,5-triazine (25.4 g, 94.8 mmol) were added to 300 ml of THF under a nitrogen atmosphere, and the mixture was stirred and refluxed. Then, potassium carbonate (17.9 g, 129.3 mmol) was dissolved in 54 ml of water, added thereto, and sufficiently stirred, and then tetrakis(triphenylphosphine)palladium(0) (1.5 g, 1.3 mmol) was added. After reacting for 11 hours, the reaction mixture was cooled to room temperature, the organic layer and the aqueous layer were separated, and then the organic layer was distilled. This was dissolved in chloroform, and washed twice with water. The organic layer was then separated, anhydrous magnesium sulfate was added, stirred, and filtered, and the filtrate was distilled under reduced pressure. The concentrated compound was purified by silica gel column chromatography to give 15.4 g of Compound 1-a. (yield: 64%, MS: [M+H]+=560)

Step 2) Synthesis of Compound 1 the organic layer and the aqueous layer were separated, and then the organic layer was distilled. This was dissolved in chloroform, and washed twice with water. The organic layer was then separated, anhydrous magnesium sulfate was added, stirred, and filtered, and the filtrate was distilled under reduced pressure. The concentrated compound was purified by silica gel column chromatography and then subjected to sublimation purification to give 9.4 g of Compound 1. (yield: 33%, MS: [M+H]+=797)

Synthesis Example 2: Synthesis of Compound 2

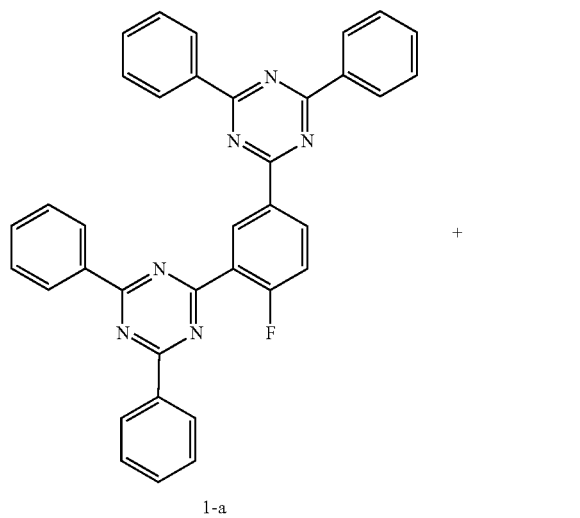

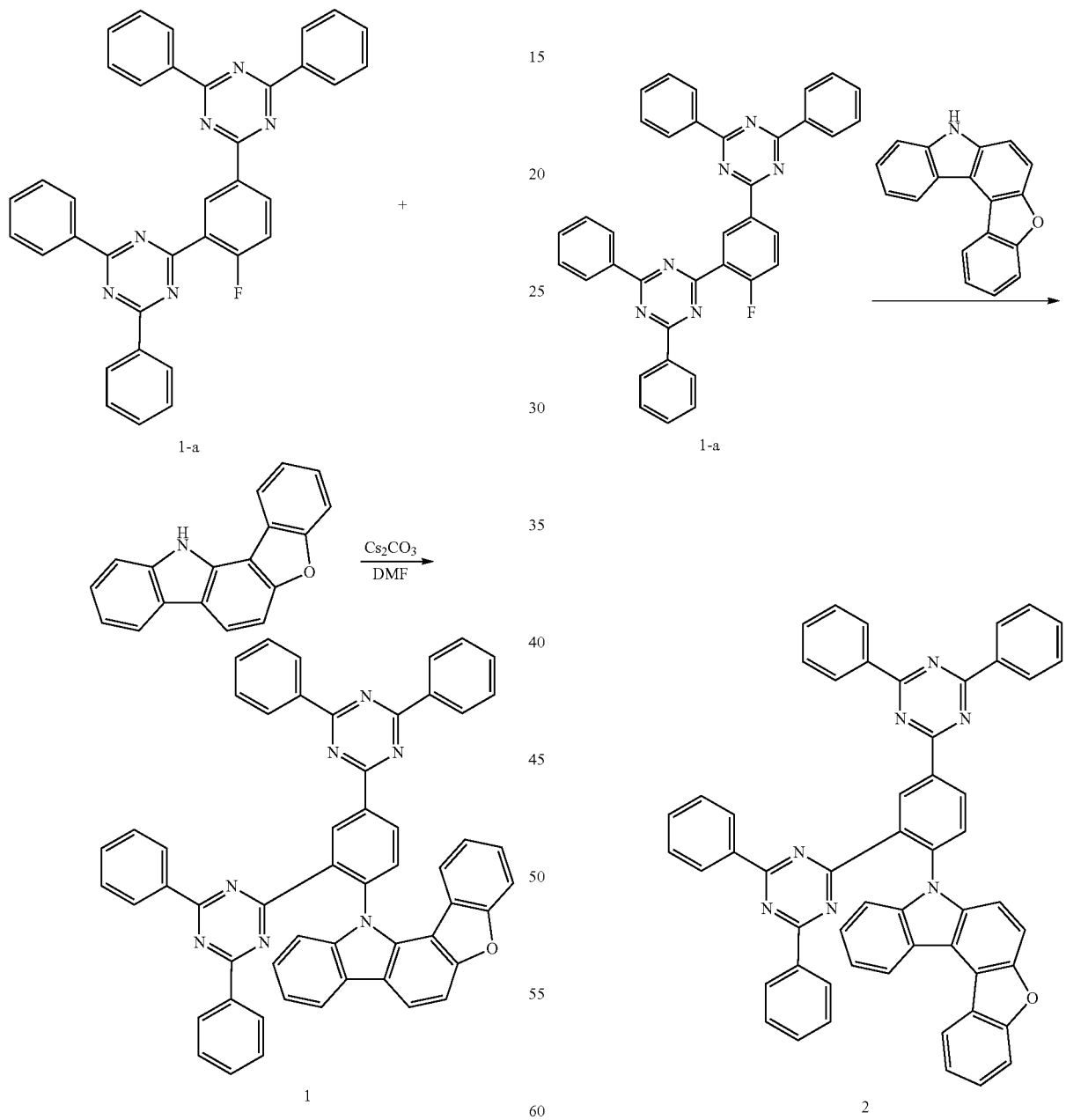

Compound 1-a (20 g, 35.8 mmol) and 12H-benzofuro[3,2-a]carbazole (10.1 g, 39.4 mmol) were added to 400 ml of DMF under a nitrogen atmosphere, and the mixture was stirred under reflux. Then, cesium carbonate (35 g, 107.4 mmol) was added thereto and stirred. After reacting for 4 hours, the reaction mixture was cooled to room temperature, Compound 2 was prepared in the same manner as in the method for preparing Compound 1, except that 8H-benzofuro[2,3-c]carbazole was used instead of 12H-benzofuro[3,2-a]carbazole in step 2 of Synthesis Example 1. (MS[M+H]+=797)

Synthesis Example 3: Synthesis of Compound 3

Synthesis Example 4: Synthesis of Compound 4

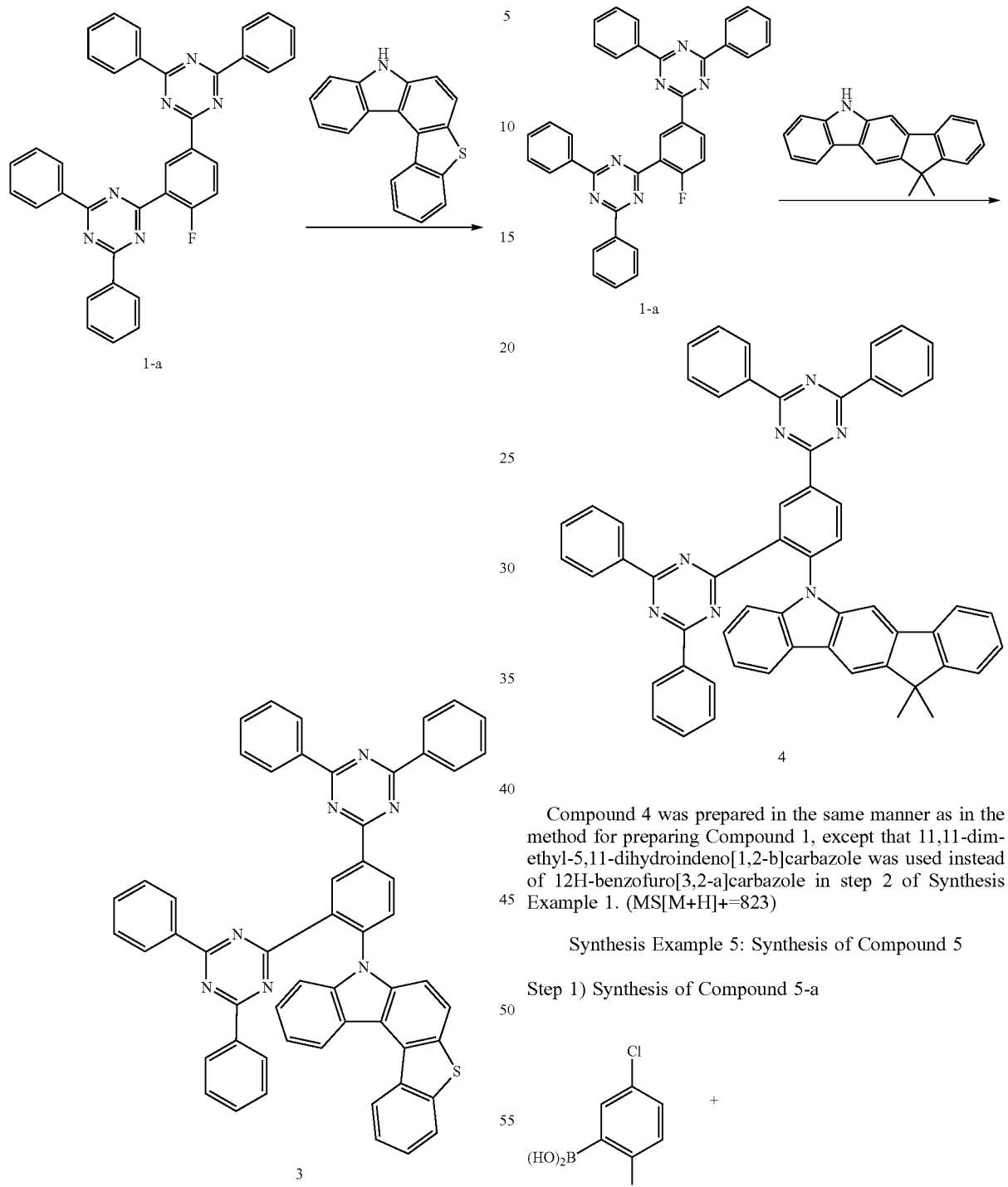

Compound 4 was prepared in the same manner as in the method for preparing Compound 1, except that 11,11-dimethyl-5,11-dihydroindeno[1,2-b]carbazole was used instead of 12H-benzofuro[3,2-a]carbazole in step 2 of Synthesis Example 1. (MS[M+H]+=823)

Synthesis Example 5: Synthesis of Compound 5

Step 1) Synthesis of Compound 5-a

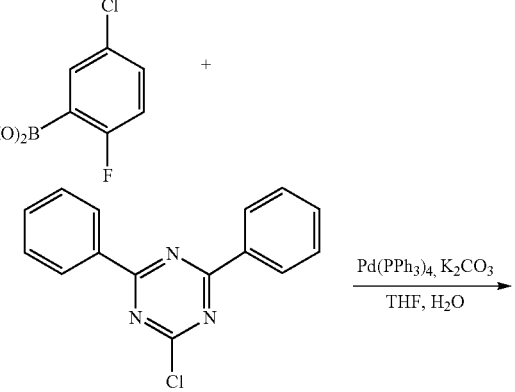

Compound 3 was prepared in the same manner as in the method for preparing Compound 1, except that 8H-benzo[4,5]thieno[2,3-c]carbazole was used instead of 12H-benzofuro[3,2-a]carbazole in step 2 of Synthesis Example 1. (MS[M+H]+=813)

-continued

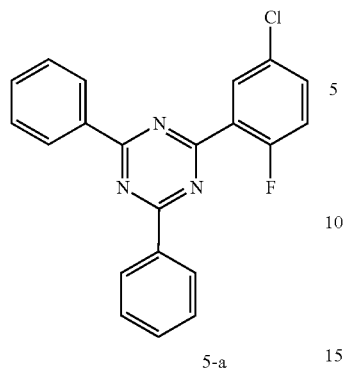

5-a (5-Chloro-2-fluorophenyl)boronic acid (15 g, 86 mmol) and 2-chloro-4,6-diphenyl-1,3,5-triazine (25.3 g, 94.6 mmol) were added to 300 ml of THF under a nitrogen atmosphere, and the mixture was stirred and refluxed. Then, potassium carbonate (35.7 g, 258.1 mmol) was dissolved in 107 ml of water, added thereto, and sufficiently stirred, and then tetrakis(triphenylphosphine)palladium(0) (3 g, 2.6 mmol) was added. After reacting for 12 hours, the reaction mixture was cooled to room temperature, the organic layer and the aqueous layer were separated, and then the organic layer was distilled. This was dissolved in chloroform, and washed twice with water. The organic layer was then separated, anhydrous magnesium sulfate was added, stirred, and filtered, and the filtrate was distilled under reduced pressure. The concentrated compound was purified by silica gel column chromatography to give 10 g of Compound 5-a. (yield: 32%, MS: [M+H]+=363)

Step 2) Synthesis of Compound 5-b

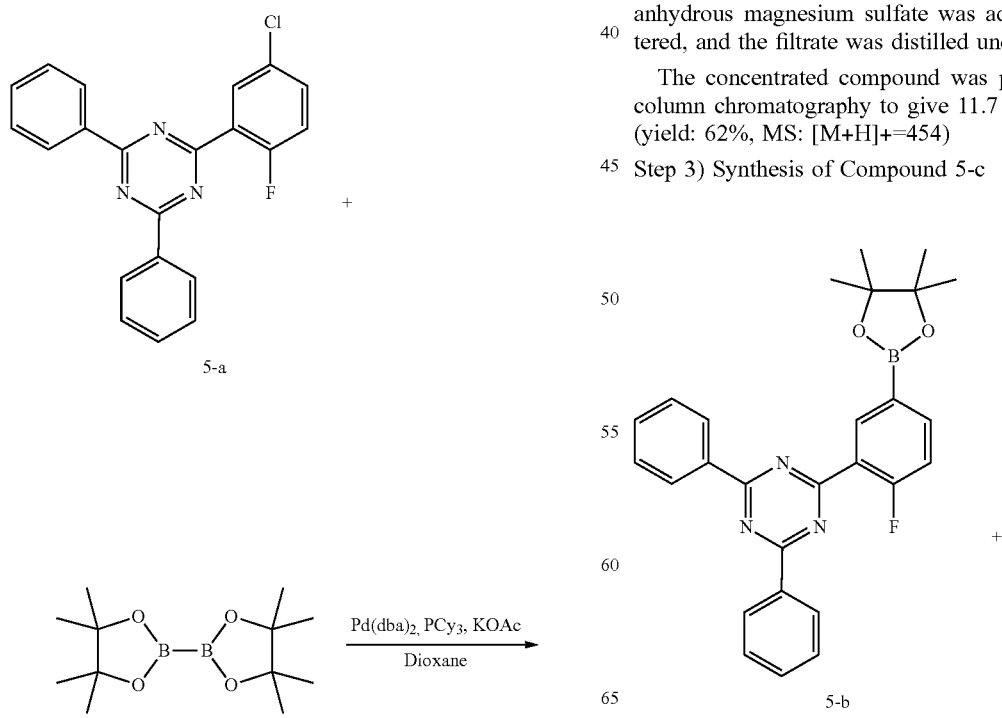

-continued

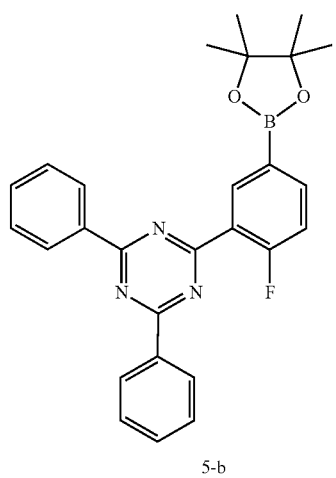

5-b

Compound 5-a (15 g, 41.5 mmol) and bis(pinacolato)diboron (11.6 g, 45.6 mmol) were added to 300 ml of 1,4-dioxane under a nitrogen atmosphere, and the mixture was stirred under reflux. Then, potassium acetate (12.2 g, 124.4 mmol) was added thereto, and sufficiently stirred, and then bis(dibenzylideneacetone)-palladium(0) (0.7 g, 1.2 mmol) and tricyclohexylphosphine (0.7 g, 2.5 mmol) were added. After reacting for 6 hours, the reaction mixture was cooled to room temperature, the organic layer and the aqueous layer were separated, and then the organic layer was distilled. This was dissolved in chloroform, and washed twice with water. The organic layer was then separated, anhydrous magnesium sulfate was added, stirred, and filtered, and the filtrate was distilled under reduced pressure.

The concentrated compound was purified by silica gel column chromatography to give 11.7 g of Compound 5-b. (yield: 62%, MS: [M+H]+=454)

Step 3) Synthesis of Compound 5-c

-continued

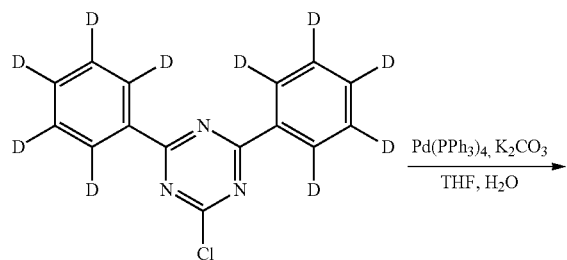 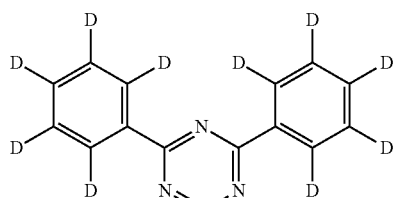

Step 4) Synthesis of Compound 5

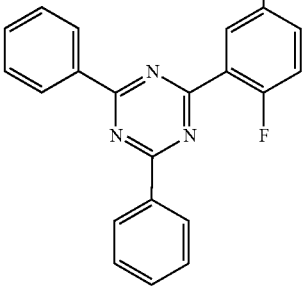

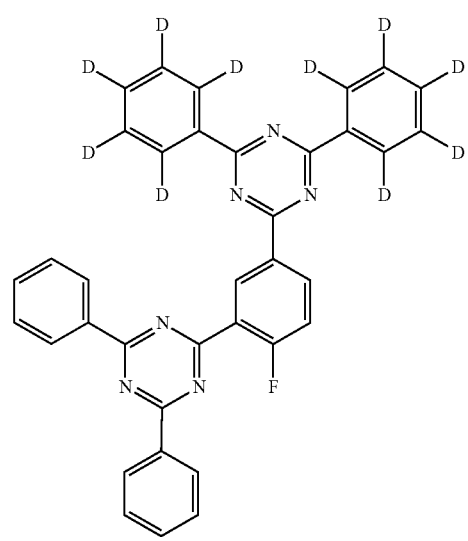

5-c

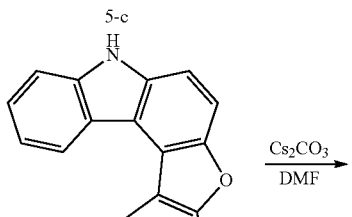

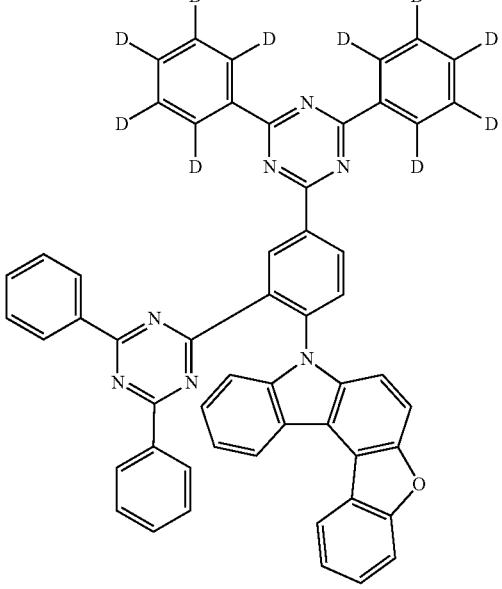

5

Compound 5-b (15 g, 33.1 mmol) and 2-chloro-4,6-bis (phenyl-d5)-1,3,5-triazine (10.1 g, 36.4 mmol) were added to 300 ml of THF under a nitrogen atmosphere, and the mixture was stirred and refluxed. Then, potassium carbonate (13.7 g, 99.3 mmol) was dissolved in 41 ml of water, added thereto and sufficiently stirred, and then tetrakis(triphenylphosphine)palladium(0) (1.1 g, 1 mmol) was added. After reacting for 11 hours, the reaction mixture was cooled to room temperature, the organic layer and the aqueous layer were separated, and then the organic layer was distilled. This was dissolved in chloroform, and washed twice with water. The organic layer was then separated, anhydrous magnesium sulfate was added, stirred, and filtered, and the filtrate was distilled under reduced pressure. The concentrated compound was purified by silica gel column chromatography to give 14.9 g of Compound 5-c. (yield: 79%, MS: [M+H]+=570)

Compound 5-c (20 g, 35.2 mmol) and 8H-benzofuro[2,3-c]carbazole (10 g, 38.7 mmol) were added to 400 ml of DMF under a nitrogen atmosphere, and the mixture was stirred under reflux. Then, cesium carbonate (34.4 g, 105.5 mmol) was added thereto and stirred. After reacting for 5 hours, the reaction mixture was cooled to room temperature, the organic layer and the aqueous layer were separated, and then the organic layer was distilled. This was dissolved in chloroform, and washed twice with water. The organic layer was then separated, anhydrous magnesium sulfate was added, stirred, and filtered, and the filtrate was distilled under reduced pressure. The concentrated compound was purified by silica gel column chromatography and then subjected to sublimation purification to give 8.8 g of Compound 5. (yield: 31%, MS: [M+H]+=807)

Synthesis Example 6: Synthesis of Compound 6

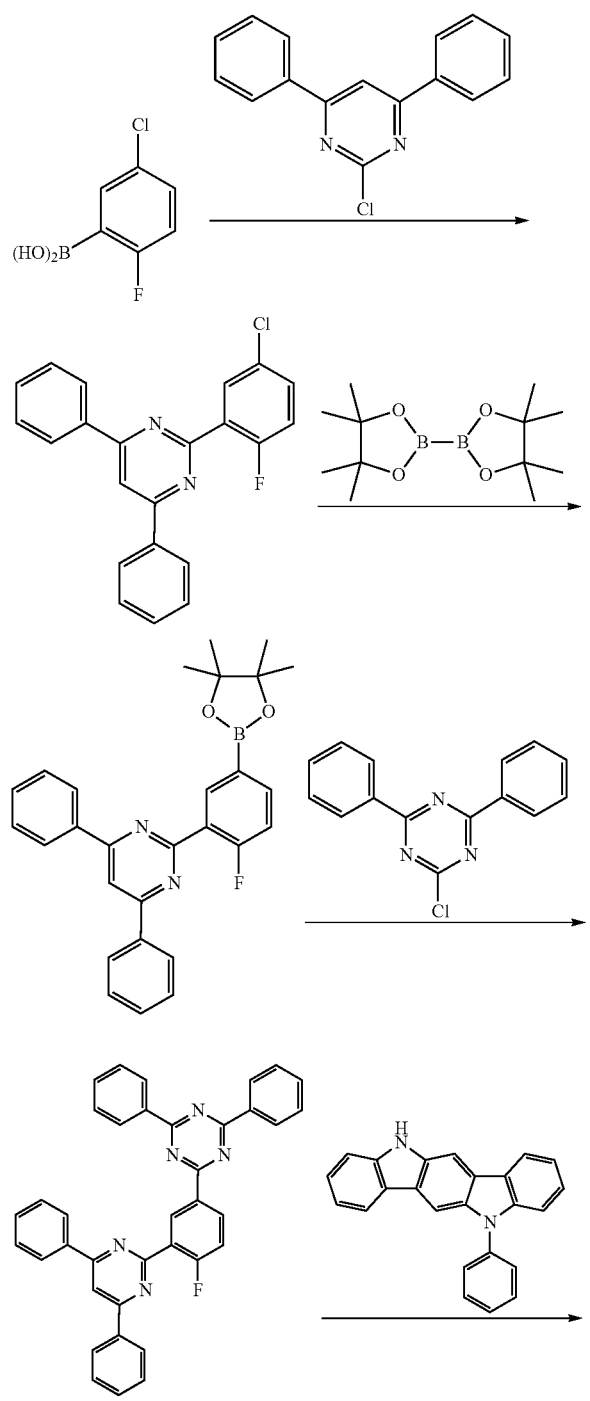

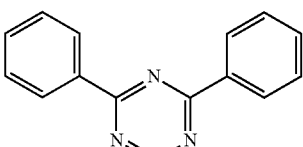

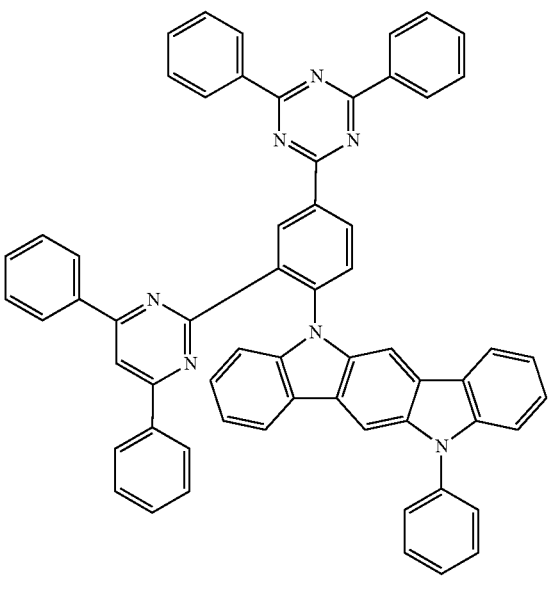

6

Compound 6 was prepared in the same manner as in the method for preparing Compound 5, except that 2-chloro-4,6-diphenylpyrimidine was used instead of 2-chloro-4,6-diphenyl-1,3,5-triazine, 2-chloro-4,6-diphenyl-1,3,5-triazine was used instead of 2-chloro-4,6-bis(phenyl-d5)-1,3,5-triazine, and 5-phenyl-5,11-dihydroindolo[3,2-b]carbazole was used instead of 8H-benzofuro[2,3-c]carbazole in Synthesis Example 5. (MS[M+H]+=871)

Synthesis Example 7: Synthesis of Compound 7

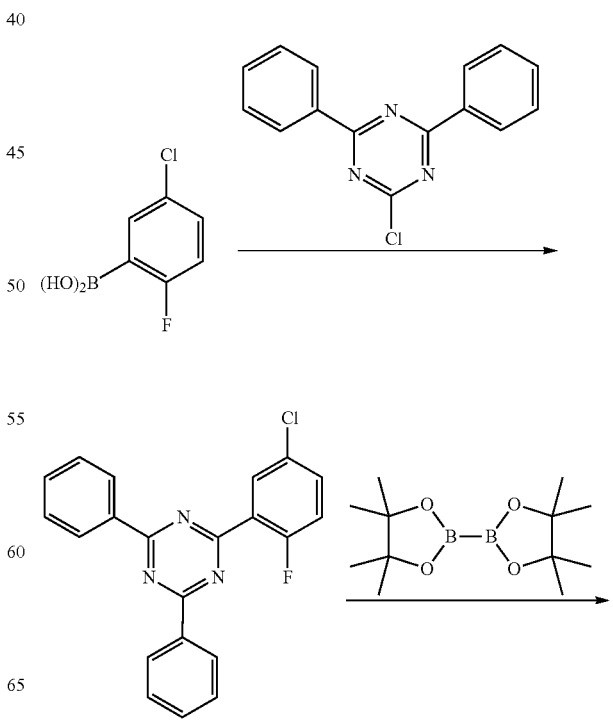

101
-continued
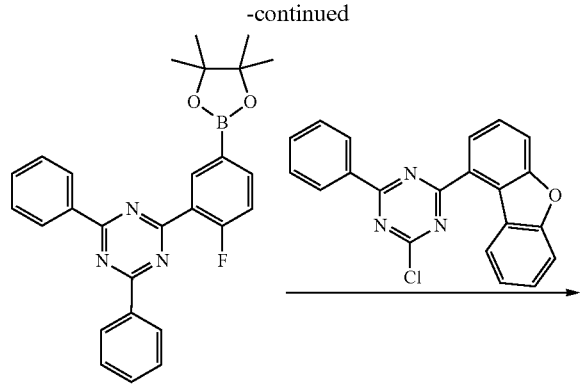
Compound 7 was prepared in the same manner as in the method for preparing Compound 5, except that 2-chloro-4-(dibenzo[b,d]furan-1-yl)-6-phenyl-1,3,5-triazine was used instead of 2-chloro-4,6-bis(phenyl-d5)-1,3,5-triazine, and 11H-benzo[4,5]thieno[3,2-b]carbazole was used instead of 8H-benzofuro[2,3-c]carbazole in Synthesis Example 5. (MS [M+H]+=903)
102
Synthesis Example 8: Synthesis of Compound 8
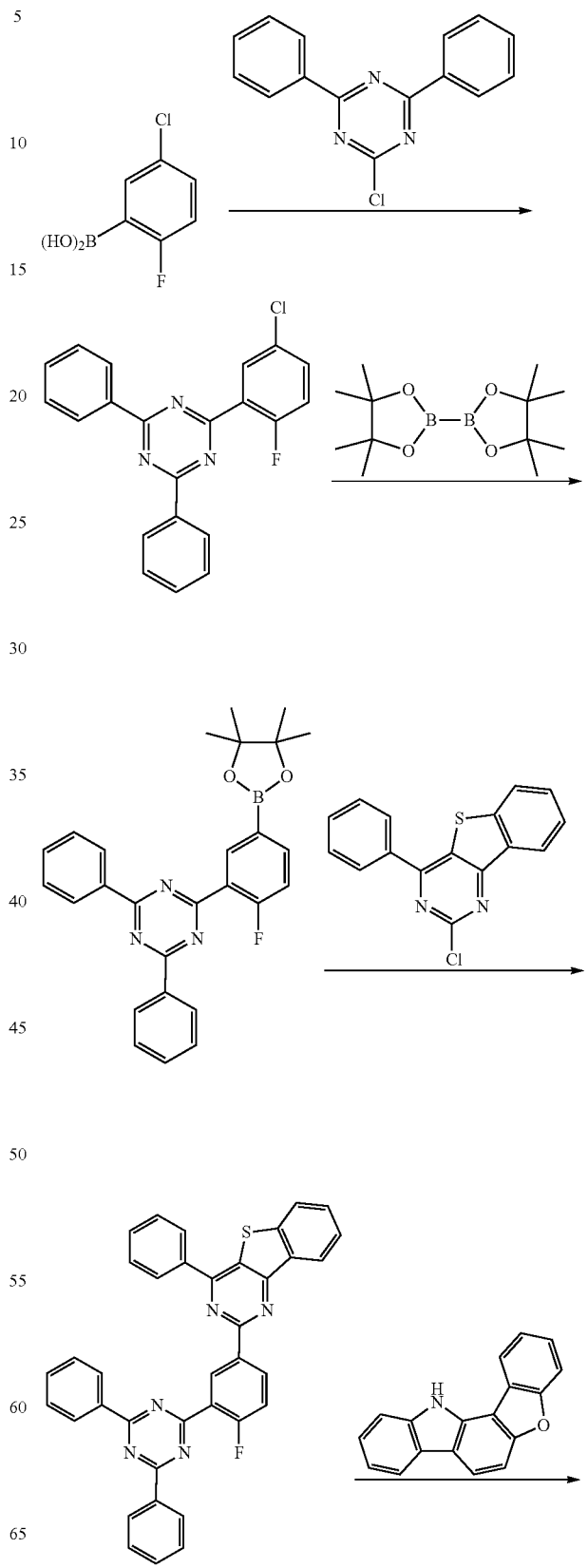

-continued

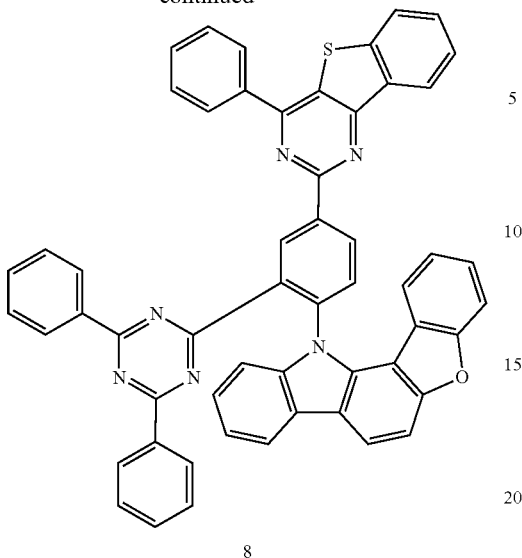

8

Compound 8 was prepared in the same manner as in the method for preparing Compound 5, except that 2-chloro-4-phenylbenzo[4,5]thieno[3,2-d]pyrimidine was used instead of 2-chloro-4,6-bis(phenyl-d5)-1,3,5-triazine, and 12H-benzofuro[3,2-a]carbazole was used instead of 8H-benzofuro[2,3-c]carbazole in Synthesis Example 5. (MS[M+H]+=826)

EXPERIMENTAL EXAMPLES

Experimental Example 1

A glass substrate on which ITO (indium tin oxide) was coated as a thin film to a thickness of 1,400 Å was put into distilled water in which a detergent was dissolved, and ultrasonically cleaned. In this case, a product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, dried, and then transferred to a plasma cleaner. The substrate was cleaned for 5 minutes using oxygen plasma and then transferred to a vacuum depositor.

On the ITO transparent electrode thus prepared, the following Compound HT-A and the following Compound PD were thermally vacuum-deposited in a ratio of 95:5 to a thickness of 100 Å, and then only the following Compound HT-A was deposited to a thickness of 1150 Å to form a hole transport layer. The following Compound HT-B was thermally vacuum-deposited to a thickness of 450 Å on the hole transport layer to form an electronic blocking layer. Then, the Compound 1 previously prepared and the following Compound GD were vacuum-deposited in a ratio of 85:15 to a thickness of 400 Å on the electronic blocking layer to form a light emitting layer. The following Compound ET-A was vacuum-deposited to a thickness of 50 Å on the light emitting layer to form a hole blocking layer. The following Compound ET-B and the following Compound Liq were thermally vacuum-deposited in a ratio of 2:1 to a thickness of 250 Å on the hole blocking layer, and then LiF and magnesium were vacuum-deposited in a ratio of 1:1 to a thickness of 30 Å to form an electron transport and injection layer. Magnesium and silver were deposited in a ratio of 1:4 to a thickness of 160 Å on the electron injection layer to form a cathode, thereby completing the manufacture of an organic light emitting device.

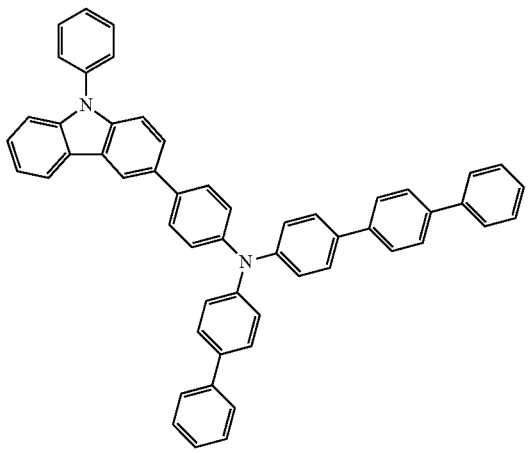

HT-A

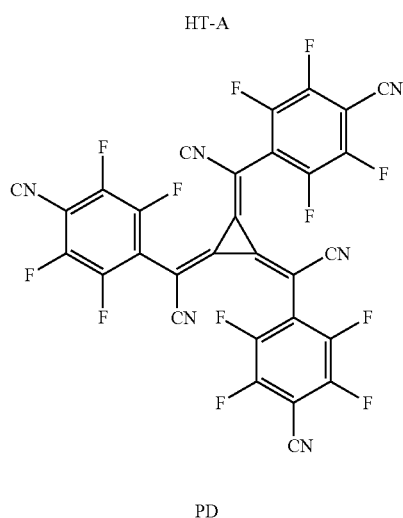

PD

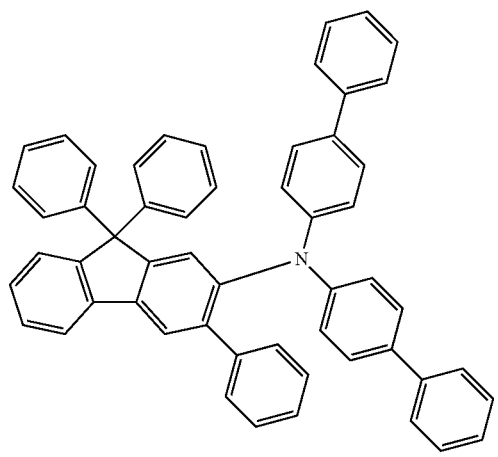

HT-B

-continued

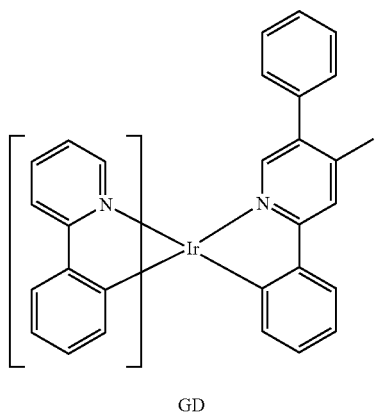

GD

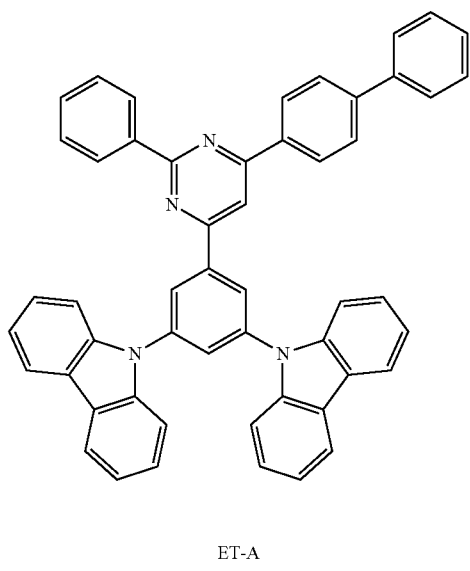

ET-A

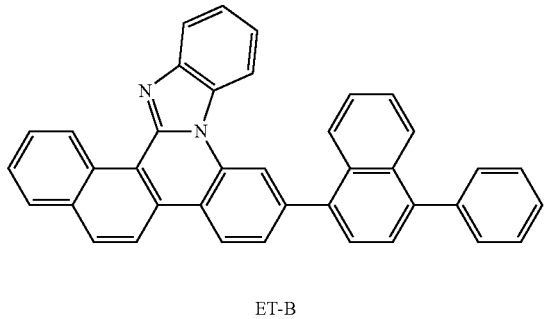

ET-B

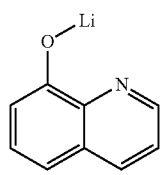

Liq

In the above-mentioned process, the vapor deposition rate of the organic material was maintained at 0.4 to 0.7 Å/sec, the deposition rate of lithium fluoride of the cathode was maintained at 0.3 Å/sec, the deposition rate of silver and magnesium was maintained at 2 Å/sec, and the degree of vacuum during the deposition was maintained at $2 \times 10^{-7}$ to $5 \times 10^{-6}$ torr, thereby manufacturing an organic light emitting device.

Experimental Examples 2 to 8

The organic light emitting devices were manufactured in the same manner as in Experimental Example 1, except that the compounds shown in Table 1 below were used instead of the Compound 1.

Comparative Experimental Examples 1 to 4

The organic light emitting devices were manufactured in the same manner as in Experimental Example 1, except that the compounds shown in Table 1 below were used instead of the Compound 1, In Table 1, the compounds GH-A, GH-B, GH-C and GH-D in Table 1 are as follows.

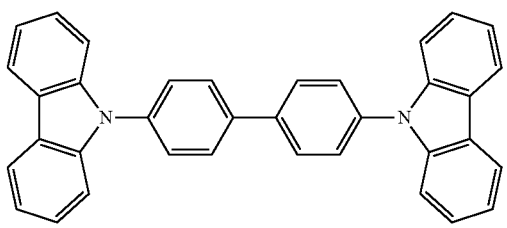

GH-A

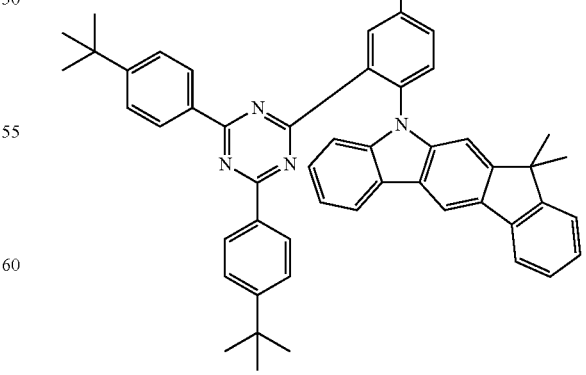

GH-B

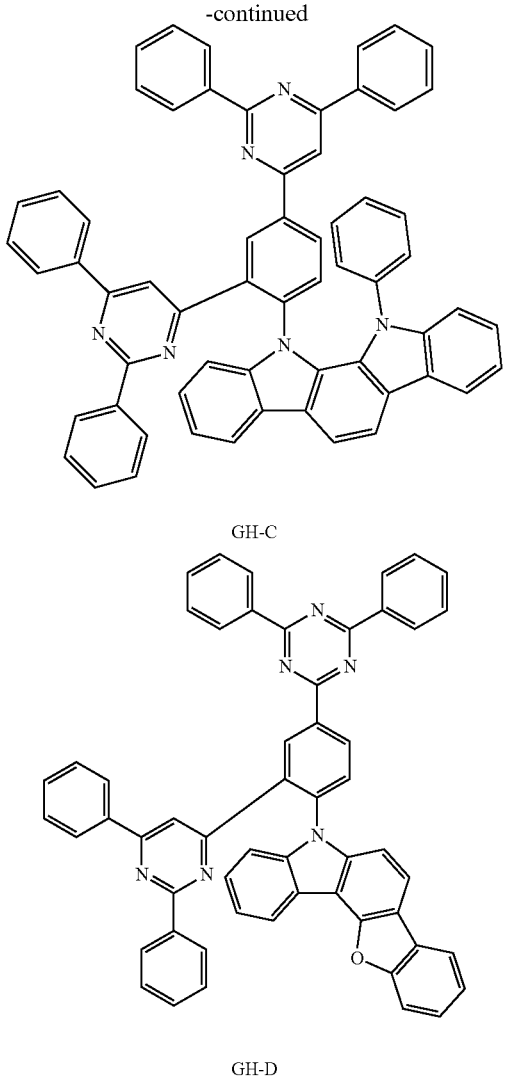

GH-C

GH-D

The voltage, efficiency and lifetime (T95) were measured by applying a current to the organic light emitting devices manufactured in Experimental Examples and Comparative Experimental Examples, and the results are shown in Table 1 below. At this time, the voltage and efficiency were measured by applying a current density of 10 mA/cm². Further, T95 in Table 1 means the time required for the luminance to be reduced to 95% of the initial luminance at a current density of 20 mA/cm².

TABLE 1

|  | Light emitting layer (host) | Voltage (V) | Efficiency (cd/A) | Lifetime (195, hr) |
|---|---|---|---|---|
| Experimental Example 1 | Compound 1 | 5.16 | 37.3 | 72 |
| Experimental Example 2 | Compound 2 | 5.03 | 36.2 | 78 |
| Experimental Example 3 | Compound 3 | 4.95 | 35.7 | 85 |
| Experimental Example 4 | Compound 4 | 5.10 | 36.8 | 74 |
| Experimental Example 5 | Compound 5 | 5.09 | 36.3 | 95 |
| Experimental Example 6 | Compound 6 | 5.11 | 36.7 | 79 |
| Experimental Example 7 | Compound 7 | 4.98 | 35.9 | 86 |
| Experimental Example 8 | Compound 8 | 5.19 | 37.9 | 77 |
| Comparative Experimental Example 1 | GH-A | 6.28 | 28.4 | 43 |
| Comparative Experimental Example 2 | GH-B | 5.18 | 32.1 | 32 |
| Comparative Experimental Example 3 | GH-C | 5.63 | 33.8 | 56 |
| Comparative Experimental Example 4 | GH-D | 5.21 | 30.4 | 52 |

The compound of Chemical Formula 1 can easily undergo intra-charge transfer because the substituent groups of Chemical Formulas 2-1 to 2-3 that act as electron donors in the molecule and the monocyclic nitrogen-containing heterocycles that act as electron acceptors are bonded to each other at the ortho position. In particular, the Chemical Formula 2-1 has a larger area facing the monocyclic nitrogen-containing heterocycle compared to similar substituents, and the Chemical Formulas 2-2 and 2-3 further push electrons because Y is located at the para position of the nitrogen atom to further push electrons, and thus, have strong electron donor characteristics. All of these two characteristics are more advantageous for intra-charge transfer. Due to this, the stability of the molecule is high, which is advantageous for both hole transport and electron transport. In addition, since various nitrogen-containing heterocycles are further substituted in Ar₃, electron transport characteristics can be variously adjusted, which is advantageous in balancing charge associated with the change of the common layer.

Therefore, as shown in Table 1 above, when using the compound of Chemical Formula 1 as a host for the organic light-emitting device, it can be confirmed that it exhibits the characteristics of low voltage, high efficiency, and long lifetime as compared with Comparative Experimental Examples having a similar structure.

EXPLANATION OF SYMBOLS

| 1: substrate | 2: anode |
|---|---|
| 3: light emitting layer | 4: cathode |
| 5: hole injection layer | 6: hole transport layer |
| 7: light emitting layer | 8: electron transport layer |
| 9: electron blocking layer | 10: hole blocking layer |
| 11: electron injection layer | |

The invention claimed is:
1. A compound of Chemical Formula 1:

Chemical Formula 1

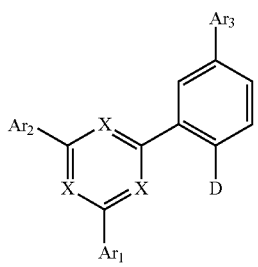

wherein, in Chemical Formula 1:
each X is independently N or CH, provided that at least one of X is N;
Ar$_1$ and Ar$_2$ are each independently a substituted or unsubstituted C$_{6-60}$ aryl or a substituted or unsubstituted C$_{5-60}$ heteroaryl containing any one or more heteroatoms selected from the group consisting of N, O and S;
Ar$_3$ is a substituent group of the following Chemical Formula 3-5:

Chemical Formula 3-5

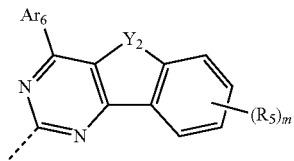

wherein, in Chemical Formula 3-5:
Ar$_6$ is a substituted or unsubstituted C$_{6-60}$ aryl;
Y$_2$ is O or S;
m is independently an integer of 0 to 4; and
each R$_5$ is independently hydrogen, deuterium, a substituted or unsubstituted C$_{1-60}$ alkyl, a substituted or unsubstituted C$_{3-60}$ cycloalkyl, a substituted or unsubstituted C$_{6-60}$ aryl, or a substituted or unsubstituted C$_{5-60}$ heteroaryl containing one or more heteroatoms selected from the group consisting of N, O and S;
D is a substituent group of any one of the following Chemical Formulas 2-1 to 2-3:

Chemical Formula 2-1

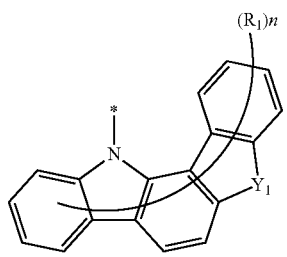

Chemical Formula 2-2

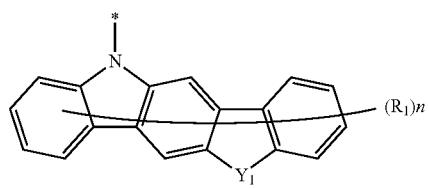

Chemical Formula 2-3

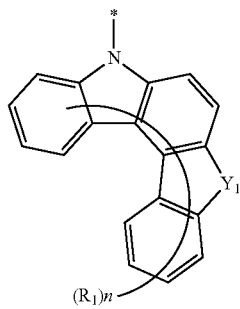

wherein, in Chemical Formulas 2-1 to 2-3:
Y is O, S, NR$_2$, or CR$_3$R$_4$;
each n is independently an integer of 0 to 10;
each R$_1$ is independently hydrogen, deuterium, a substituted or unsubstituted C$_{1-60}$ alkyl, a substituted or unsubstituted C$_{3-60}$ cycloalkyl, a substituted or unsubstituted C$_{6-60}$ aryl, or a substituted or unsubstituted C$_{5-60}$ heteroaryl containing one or more heteroatoms selected from the group consisting of N, O and S; and
R$_2$ to R$_4$ are each independently a substituted or unsubstituted C$_{1-60}$ alkyl or a substituted or unsubstituted C$_{6-60}$ aryl.

2. The compound of claim 1, wherein the Chemical Formula 1 is any one of the following Chemical Formulae 1-1 to 1-3:

Chemical Formula 1-1

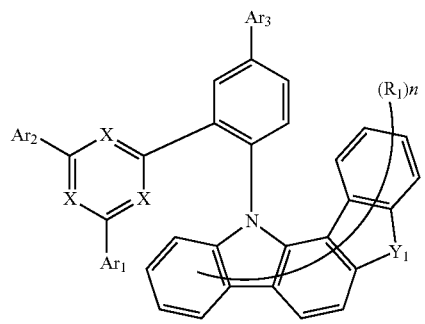

Chemical Formula 1-2

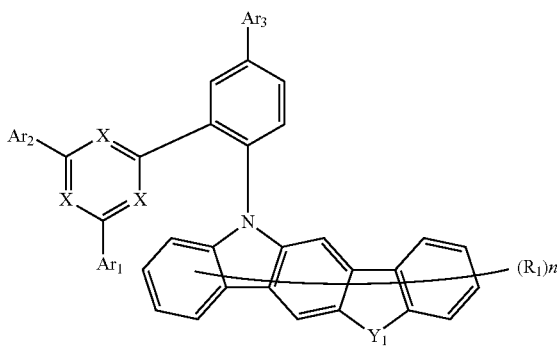

Chemical Formula 1-3

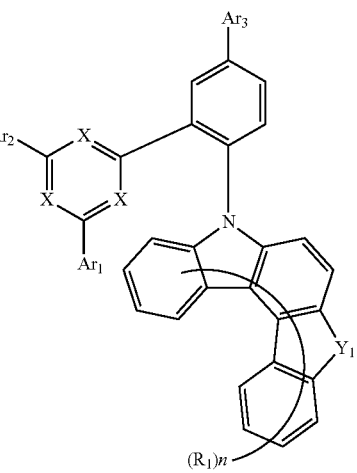

wherein, in Chemical Formulas 1-1 to 1-3:
X, Ar$_1$ to Ar$_3$, Y$_1$, R$_1$ and n are as defined in claim 1 for Chemical Formula 1.

3. The compound of claim 1, wherein $Y_1$ is O, S, $N(C_6H_5)$, $N(C_6D_5)$, or $C(CH_3)_2$.

4. The compound of claim 1, wherein $Ar_1$ and $Ar_2$ are each independently phenyl, biphenyl, naphthyl, or a phenyl group substituted with 1 to 5 deuterium.

5. The compound of claim 1, wherein $Ar_6$ is phenyl, biphenyl, or a phenyl group substituted with 1 to 5 deuterium.

6. The compound of claim 1, wherein the compound of Chemical Formula 1 is any one compound selected from the group consisting of the following compounds:

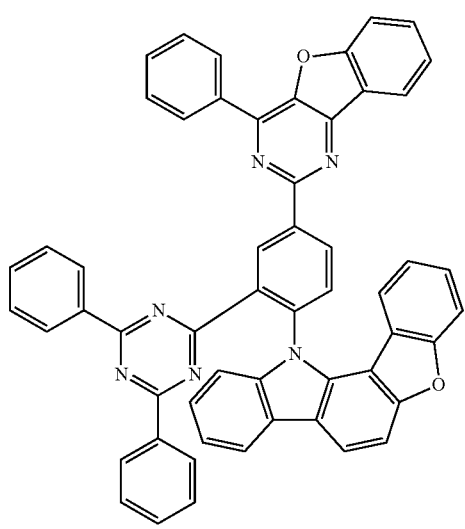

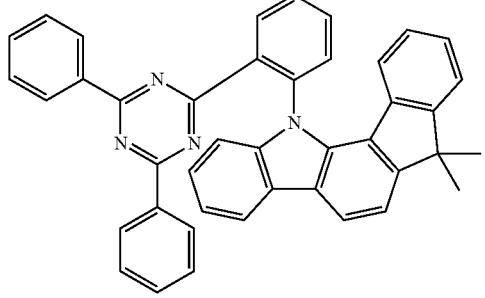

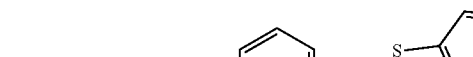

113
-continued
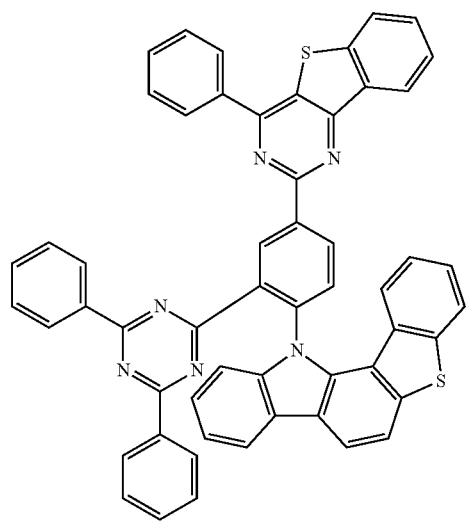
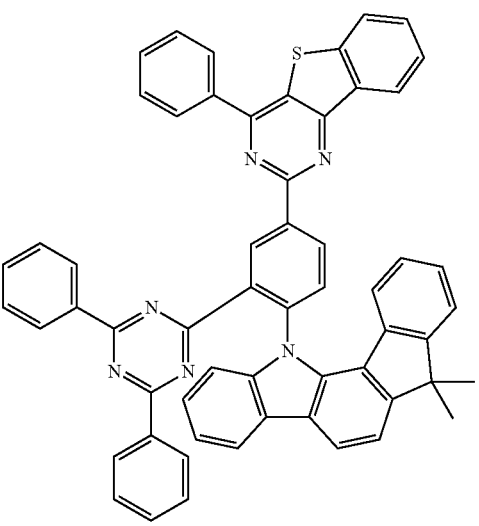
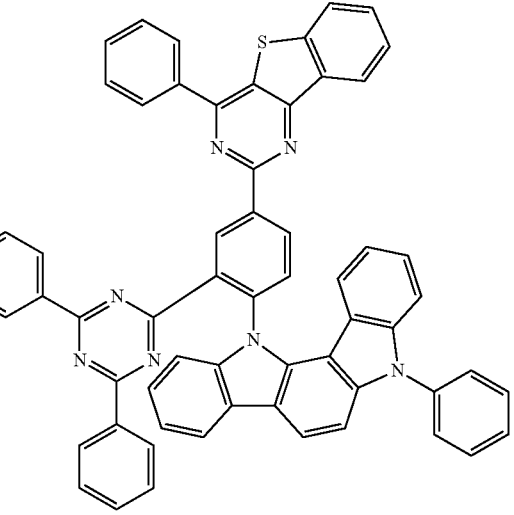
114
-continued
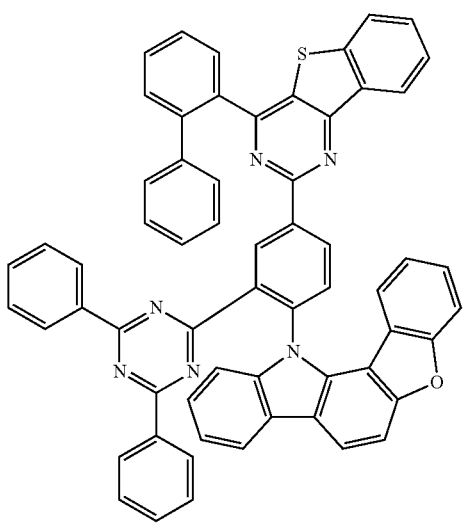
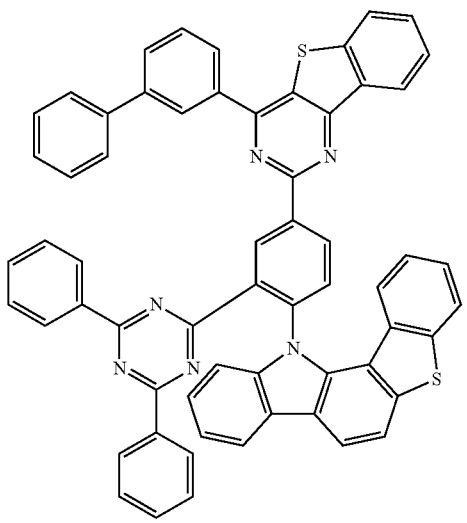
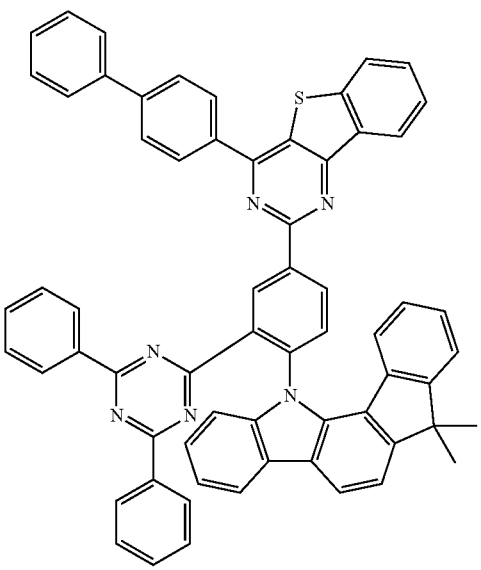

115
-continued
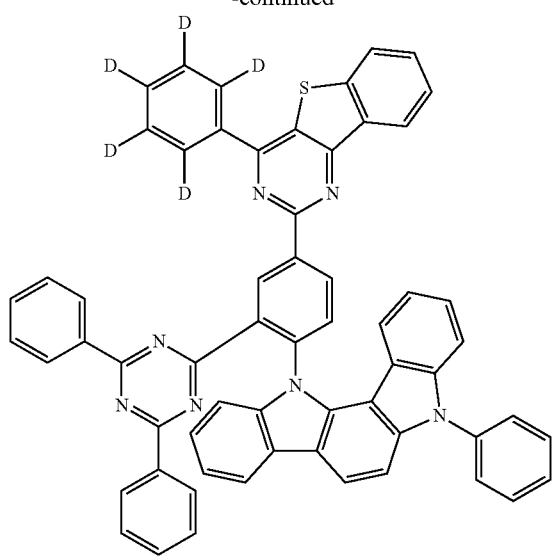
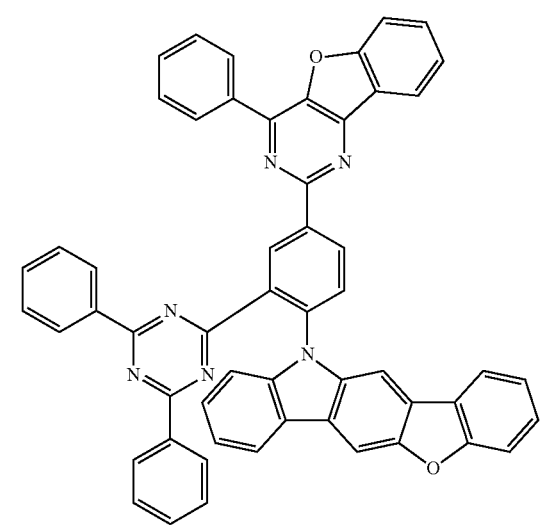
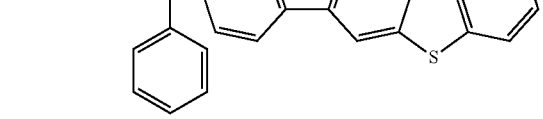
116
-continued
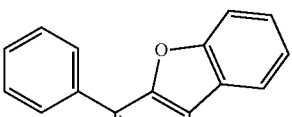
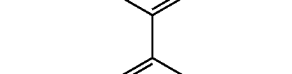
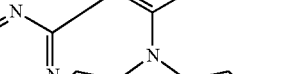

117
-continued
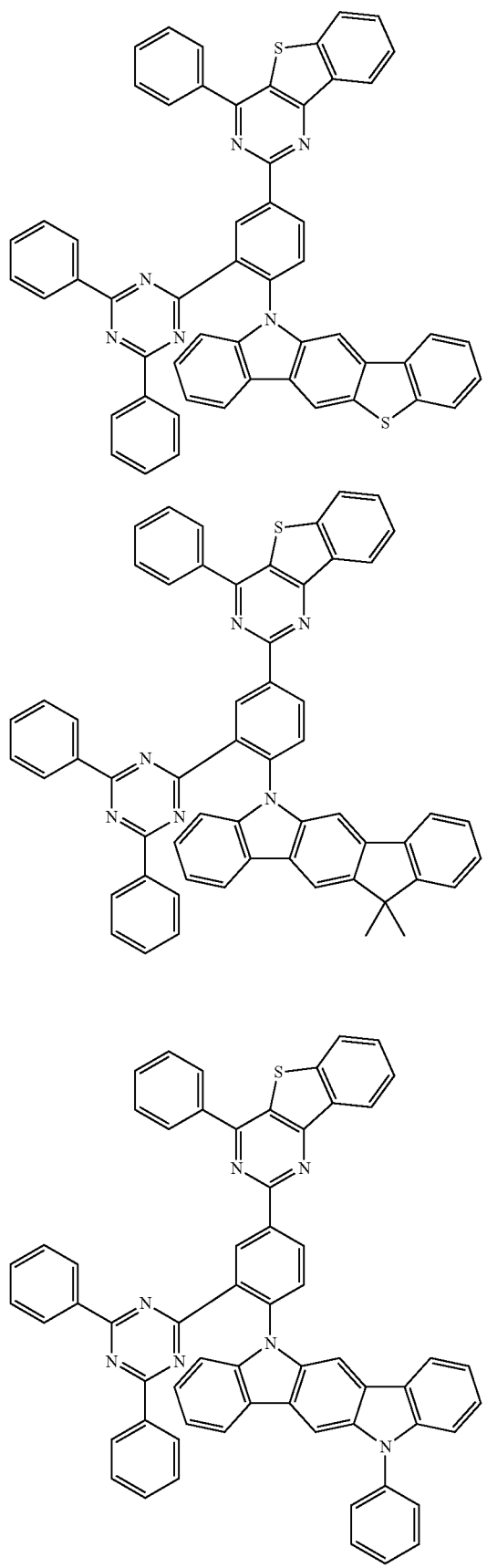
118
-continued
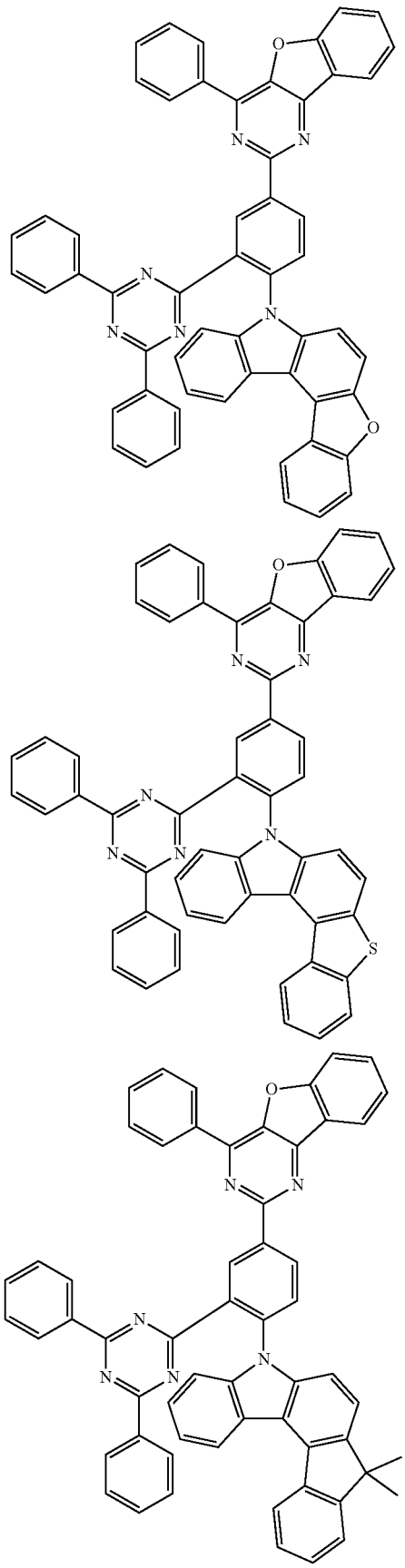

119
-continued

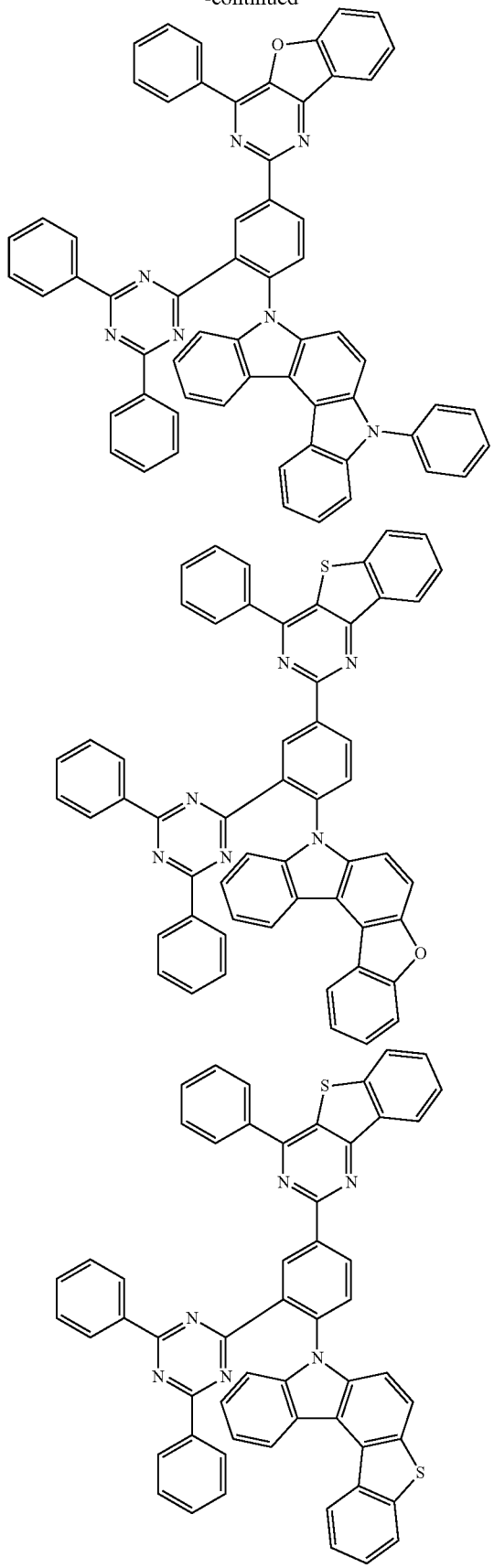

120
-continued

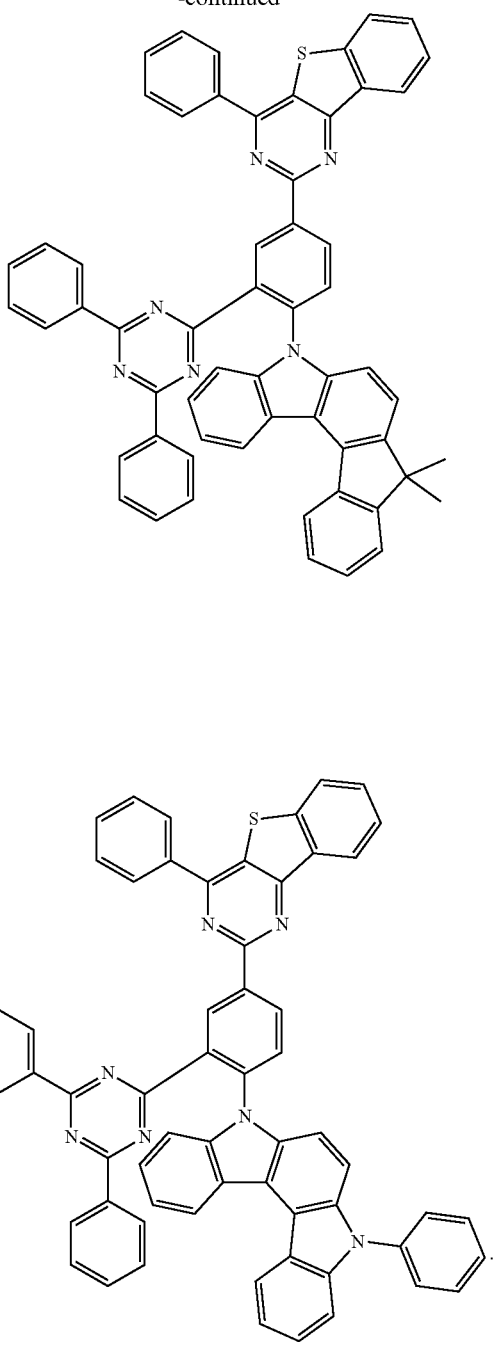

7. An organic light emitting device comprising:
a first electrode;
a second electrode that is provided opposite to the first electrode; and
one or more organic material layers that are provided between the first electrode and the second electrode, wherein one or more layers of the one or more organic material layers comprise the compound of claim 1.

* * * * *